US012588612B2

(12) United States Patent \
Puglisi et al.

(10) Patent No.: US 12,588,612 B2 \
(45) Date of Patent: Mar. 31, 2026

(54) PARTHENOCARPIC WATERMELON PLANTS

(71) Applicant: NUNHEMS B.V., Nunhem (NL)

(72) Inventors: Daniel Puglisi, Sant Agata Bolognese (IT); Alberto Sirizzotti, Sant Agata Bolognese (IT); Courtney Hu, Davis, CA (US); Mona Mazaheri, Davis, CA (US)

(73) Assignee: Nunhems B.V., Nunhem (NL)

( * ) Notice: Subject to any disclaimer, the term of this patent is extended or adjusted under 35 U.S.C. 154(b) by 284 days.

(21) Appl. No.: 18/031,322

(22) PCT Filed: Oct. 4, 2021

(86) PCT No.: PCT/EP2021/077239 \
§ 371 (c)(1), \
(2) Date: Apr. 11, 2023

(87) PCT Pub. No.: WO2022/078792 \
PCT Pub. Date: Apr. 21, 2022

(65) Prior Publication Data

US 2023/0371453 A1     Nov. 23, 2023

Related U.S. Application Data

(60) Provisional application No. 63/117,223, filed on Nov. 23, 2020, provisional application No. 63/111,898, filed on Nov. 10, 2020.

(30) Foreign Application Priority Data

Oct. 12, 2020    (EP) .................................... 20201337

(51) Int. Cl. \
A01H 5/08        (2018.01) \
A01H 6/34        (2018.01)

(52) U.S. Cl. \
CPC ............... A01H 6/342 (2018.05); A01H 5/08 (2013.01)

(58) Field of Classification Search \
None \
See application file for complete search history.

(56) References Cited

U.S. PATENT DOCUMENTS

| | | |
|---|---|---|
| 5,210,015 A | 5/1993 | Gelfand et al. |
| 5,487,972 A | 1/1996 | Gelfand et al. |
| 7,615,620 B2 | 11/2009 | Robinson |

FOREIGN PATENT DOCUMENTS

| | | |
|---|---|---|
| EP | 1726664 B1 | 1/2010 |
| EP | 2959771 A1 | 12/2015 |
| EP | 3332633 A1 | 6/2018 |
| WO | 2012/069539 A1 | 5/2012 |
| WO | 2017/202715 A1 | 11/2017 |
| WO | WO2018/060444 A1 * | 4/2018 ............... A01H 5/08 |
| WO | 2019/238832 A1 | 12/2019 |

OTHER PUBLICATIONS

Helft et al., 2011, LRR Conservation Mapping to Predict Functional Sites within Protein Leucine-Rich Repeat Domains, PLoS One, vol. 6(7), pp. 1-14 (Year: 2011).*

Acciarri, et al., "Genetically modified parthenocarpic eggplants: improved fruit productivity under both greenhouse and open field cultivation", BMC biotechnology, vol. 2, Article No. 4, Apr. 4, 2002, 7 pages.

Allen, et al., "Transcript-specific, single-nucleotide polymorphism discovery and linkage analysis in hexaploid bread wheat (*Triticum aestivum* L.)", Plant biotechnology journal, vol. 9, Issue 9, Jun. 1, 2011, pp. 1086-1099.

Bhatta, et al., "Improving Horticultural Crops via CRISPR/Cas9: Current Successes and Prospects", Plants, vol. 9, Issue 10, Oct. 14, 2020, pp. 1-19.

Database CUGenDB [Online], retrieved from Database accession No. Cla97C05G081250, XP002802251, Jan. 1, 2013, 4 pages.

Erpen-Dalla Corte, et al., "Development of improved fruit, vegetable, and ornamental crops using the CRISPR/Cas9 genome editing technique", Plants, vol. 8, Issue 12, Dec. 13, 2019, pp. 1-22.

European Search Report for EP Patent Application No. 20201337.1, Issued on Mar. 26, 2021, 3 pages.

Guner, et al., "The genes of watermelon", HortScience, vol. 39, Issue 6, Oct. 2004, pp. 1175-1182.

Guo, et al., "The draft genome of watermelon (*Citrullus lanatus*) and resequencing of 20 diverse accessions", Nature Genetics, vol. 45, Issue 1, Nov. 25, 2012, pp. 51-58.

H. Kihara, "Triploid Watermelons", American Society for Horticultural Science, vol. 58, 1951, pp. 217-230.

He, et al., "SNP genotyping: the KASP assay", Crop breeding: methods and protocols, vol. 1145, 2014, pp. 75-86.

International Search Report for PCT Patent Application No. PCT/EP2021/077239, Issued on Jan. 10, 2022, 5 pages.

Lohmann, et al., "Slow Motion is required for within-plant auxin homeostasis and normal timing of lateral organ initiation at the shoot meristem in *Arabidopsis*", The Plant Cell, vol. 22, Issue 2, Feb. 5, 2010, pp. 335-348.

Noh, et al., "Screening different methods of tetraploid induction in watermelon [*Citrullus lanatus* (thunb.) Manst. and Nakai]", Horticulture, Environment, and Biotechnology, vol. 53, Jan. 11, 2013, pp. 521-529.

O. J. Eigsti, "About Our Cover", HortScience, vol. 6, Issue 1, Feb. 1971, 1 page.

Rotino, et al., "Open field trial of genetically modified parthenocarpic tomato: seedlessness and fruit quality", BMC biotechnology, vol. 5, Article No. 32, Dec. 21, 2005, 8 pages.

Ruan, et al., "Molecular regulation of seed and fruit set", Trends in Plant Science, vol. 17, Issue 11, 2012, pp. 1360-1385.

(Continued)

*Primary Examiner* — Amjad Abraham \
*Assistant Examiner* — Christina L Meadows \
(74) *Attorney, Agent, or Firm* — ArentFox Schiff LLP

(57) ABSTRACT

The present invention is directed to seedless fruit producing watermelon, cucumber or melon plants. The present invention also comprises methods for production of said plants and methods for producing seedless watermelon, cucumber or melon fruits.

24 Claims, 8 Drawing Sheets

Figure 1:
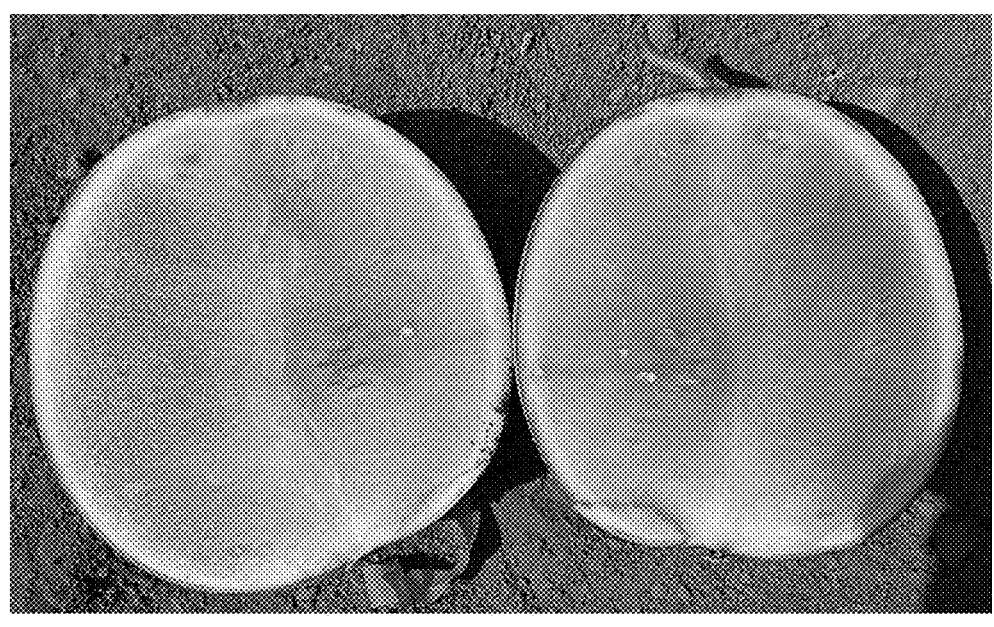

Specification includes a Sequence Listing.

(56)          References Cited

OTHER PUBLICATIONS

Sari, et al., "Comparison of ploidy level screening methods in watermelon: *Citrullus lanatus* (Thunb.) Matsum. and Nakai", Scientia Horticulturae, vol. 82, Issues 3-4, Dec. 23, 1999, p.

Sirizzotti, et al., Unpublished European Patent Application No. 16171462.1, titled "Seedless fruit producing plants", filed on May 26, 2016, 62 pages.

Xu, et al., "Evolution of F-box genes in plants: different modes of sequence divergence and their relationships with functional diversification", Proceedings of the National Academy of Sciences, vol. 106, Issue 3, Jan. 20, 2009, pp. 835-840.

Yin, et al., "The DefH9-iaaM-containing construct efficiently induces parthenocarpy in cucumber", Cellular and Molecular Biology Letters, vol. 11, Issue 2, Jun. 1, 2006, pp. 279-290.

Zhang, et al., "Characteristics of a novel male-female sterile watermelon (*Citrullus lanatus*) mutant", Scientia horticulturae, vol. 140, Jun. 1, 2012, pp. 107-114.

Zhang, et al., "Development of genic male-sterile watermelon lines with delayed-green seedling marker", HortScience, vol. 31, Issue 1, Feb. 1996, pp. 123-126.

Zhang, et al., "Tissue culture-induced heritable genomic variation in rice, and their phenotypic implications", PloS one, vol. 9, Issue 5, May 7, 2014, pp. 1-10.

* cited by examiner

Figure 2

```
wt       1  MTIWCCLCFTVGEEDEREREEELKKEGEMKPMMREEVFENQDDSDRIVRN    50
            |||||||||||||||||||||||||||||||||||||||||||||||||||
wap5.1   1  MTIWCCLCFTVGEEDEREREEELKKEGEMKPMMREEVFENQDDSDRIVRN    50 wt      51  GDDSQGSNPLPIAVDDAPDRHDGDRLRLFEDMVRAMHDGADGGGAHWDDE   100
            |||||||||||||||||||||||||||||||||||||||||||||||||||
wap5.1  51  GDDSQGSNPLPIAVDDAPDRHDGDRLRLFEDMVRAMHDGADGGGAHWDDE   100 wt     101  LRGGGGGAINPWNFSFGILHQSEGGESSSASALSLSSTVETSNEERDRDA   150
            |||||||||||||||||||||||||||||||||||||||||||||||||||
wap5.1 101  LRGGGGGAINPWNFSFGILHQSEGGESSSASALSLSSTVETSNEERDRDA   150 wt     151  NHKRAKVLSKFTESSFATPWPLGAGNPMRDYDFIHGSSSIMSRNEFLYHA   200
            |||||||||||||||||||||||||||||||||||||||||||||||||||
wap5.1 151  NHKRAKVLSKFTESSFATPWPLGAGNPMRDYDFIHGSSSIMSRNEFLYHA   200 wt     201  STSCRVDEDLESSFGRDDGINDNDTCKSEGFEVRMDLTDDLLHMVFSFLD   250
            |||||||||||||||||||||||||||||||||||||||||||||||||||
wap5.1 201  STSCRVDEDLESSFGRDDGINDNDTCKSEGFEVRMDLTDDLLHMVFSFLD   250 wt     251  HINLCRAAIVCRQWQAASAHEDFWRCLNFENRNISMEQFEDMCGRYPNAT   300
            |||||||||||||||||||||||||||||||||||||||||||||||||||
wap5.1 251  HINLCRAAIVCRQWQAASAHEDFWRCLNFENRNISMEQFEDMCGRYPNAT   300 wt     301  EVNISGVPAVHLLAMKAVSSLRHLEVLTLGRGQLADNFFHALTDCHLLKS   350
            |||||||||||||||||||||||||||||||||||||||||||||||||||
wap5.1 301  EVNISGVPAVHLLAMKAVSSLRHLEVLTLGRGQLADNFFHALTDCHLLKS   350 wt     351  LTVNDSTLVNVTQEIPISHDRLRHLHLTKCRVIRISVRCPQLETLSLKRS   400
            |||||||||||||||||||||||||||||||||||||||||||||||||||
wap5.1 351  LTVNDSTLVNVTQEIPISHDRLRHLHLTKCRVIRISVRCPQLETLSLKRS   400 wt     401  NMAQAVLNCPLLRDLDIGSCHKLSDAAIRSAAISCPQLESLDMSNCSCVS   450
            |||||||||||||||||||||||||||||||||||||||||||||||||||
wap5.1 401  NMAQAVLNCPLLRDLDIGSCHKLSDAAIRSAAISCPQLESLDMSNCSCVS   450 wt     451  DETLREISANCPNLQLLNASYCPNISLESVRLTMLTVLKLHSCEGITSAS   500
            |||||||||||||||||||||||||||||||||||||||||||||||||||
wap5.1 451  DETLREISANCPNLQLLNASYCPNISLESVRLTMLTVLKLHSCEGITSAS   500 wt     501  MTAISSSSGLKVLELDNCSLLTSVSLDLPHLQNIRLVHCRKFSDLSLQSV   550
            |||||||||||||||||||||||||||||.|||||||||||||||||||||
wap5.1 501  MTAISSSSGLKVLELDNCSLLTSVSLDFPHLQNIRLVHCRKFSDLSLQSV   550 wt     551  KLSSIMVSNCPSLHRINITSNLLQKLVLKKQESLAKLVLQCPSLQDVDLT   600
            |||||||||||||||||||||||||||||||||||||||||||||||||||
wap5.1 551  KLSSIMVSNCPSLHRINITSNLLQKLVLKKQESLAKLVLQCPSLQDVDLT   600 wt     601  DCESLTNSICEVFSDGGGCPMLKSLVLDNCESLTAVRFCSSSLGSLSLVG   650
            |||||||||||||||||||||||||||||||||||||||||||||||||||
wap5.1 601  DCESLTNSICEVFSDGGGCPMLKSLVLDNCESLTAVRFCSSSLGSLSLVG   650
```

Figure 2 (continued)

```
wt        651 CRAITSLELQCPNLEQVSLDGCDHLERASFSPVGLRSLNLGICPKLNELK  700
              |||||||||||||||||||||||||||||||||||||||||||||||||
wap5.1    651 CRAITSLELQCPNLEQVSLDGCDHLERASFSPVGLRSLNLGICPKLNELK  700 wt        701 LEAPRMDLLELKGCGGLSEAAINCPRLTSLDASFCGQLKDECLSATTASC  750
              |||||||||||||||||||||||||||||||||||||||||||||||||
wap5.1    701 LEAPRMDLLELKGCGGLSEAAINCPRLTSLDASFCGQLKDECLSATTASC  750 wt        751 PQIESLILMSCPSVGSEGLYSLRCLLKLVVLDLSYTFLMSLQPVFESCIQ  800
              |||||||||||||||||||||||||||||||||||||||||||||||||
wap5.1    751 PQIESLILMSCPSVGSEGLYSLRCLLKLVVLDLSYTFLMSLQPVFESCIQ  800 wt        801 LKVLKLQACKYLTDSSLEPLYKEDALPALQELDLSYGTLCQSAIEELLAC  850
              |||||||||||||||||||||||||||||||||||||||||||||||||
wap5.1    801 LKVLKLQACKYLTDSSLEPLYKEDALPALQELDLSYGTLCQSAIEELLAC  850 wt        851 CTHLTHVSLNGCVNMHDLNWGCSIGQLSLSSIPIPLGQATLDEIEEPVAQ  900
              |||||||||||||||||||||||||||||||||||||||||||||||||
wap5.1    851 CTHLTHVSLNGCVNMHDLNWGCSIGQLSLSSIPIPLGQATLDEIEEPVAQ  900 wt        901 PNRLLQNLNCVGCQNIRKVLIPPAARCFHLSSLNLSLSSNLKEVDVSCYN  950
              |||||||||||||||||||||||||||||||||||||||||||||||||
wap5.1    901 PNRLLQNLNCVGCQNIRKVLIPPAARCFHLSSLNLSLSSNLKEVDVSCYN  950 wt        951 LCFLNLSNCCSLEVLKLDCPRLTSLFLQSCNIEEEVVVAAVSRCSMLETL 1000
              |||||||||||||||||||||||||||||||||||||||||||||||||
wap5.1    951 LCFLNLSNCCSLEVLKLDCPRLTSLFLQSCNIEEEVVVAAVSRCSMLETL 1000 wt       1001 DVRLCPKISSISMVQLRIACPSLKRIFSTLSPT       1033
              ||||||||||||||||||||||||||||||||||
wap5.1   1001 DVRLCPKISSISMVQLRIACPSLKRIFSTLSPT       1033
```

Figure 4

```
wap5.1     MTIWCCLCFTVG----EEDEREREEELKK-EGEMKPMMREEVFENQDDSDRIVRNGDDSQ
melon      MTIWCCLCFTVGEEEEEEEDEPEREEEVKKEEGEMKPMMREEVFENQDDSDRIVRNGDDSQ
cucumber   MTIWCCLCFTVG-EEEEEDERAREEEVKKEEGEMKPMMREEVFENQDDSDRIVRNGDDSQ
           *********       *  .  ************************** wap5.1     GSNPLPIAVDDAPDRHDGDRLRLFEDMVRAMHDGADGGG-AHWDDELRGG--GGGAINPW
melon      GSNPLASAVDDVPERHGSDQLRLFEDMVRAMHDGGDGGAHCHWDDELRGGGAGGGVINPW
cucumber   GSNPLASAVDDVPERHDGDRLRLFEDMVRAMHDGGDGG--AHWDDELRGAGAGGGAINPW
           ***. **.*;**..*.************.* .*****. *.**** wap5.1     NFSFGILHQSEGGESSSASALSLSSTVETSNEERDRDANHKRAKVLSKFTESSFATPWPL
melon      NLSFGIMHQSEGGESSSASALPLSSMAETSIEERDRDAHHKRAKVHSKFIESSFATPWPL
cucumber   NLSFGIMHQSEGGESSSASALPLSSMVETSMEERDRDAHHKRAKVHSKFIESSFATPWPL
           *;**;********.*  .* ***;** * ********** wap5.1     GAGNPMRDYDFIHGSSSIMSRNEFLYHASTSCRV--DEDLESSFGRDDGINDNDTCKSEG
melon      GAGNPMREFDFIHGSSSIMSRNEFLYHASTSSRIDADKDLESSFGRDDGINENDTCKSEG
cucumber   GAGNPMREYDFIHGSPSIMSRNEFLYHASTSSRFDADKDLESSFGRDDGINENDTCKSEG
           ****;;** .************* .*.  *;**********;***** wap5.1     FEVRMDLTDDLLHMVFSFLDHINLCRAAIVCRQWQAASAHEDFWRCLNFENRNISMEQFE
melon      FEVRMDLTDDLLHMVFSFLDHINLCRAAIVCRQWQAASAHEDFWRCLNFENRNISMEQFE
cucumber   FEVRMDLTDDLLHMVFSFLDHINLCRAAIVCRQWQAASAHEDFWRCLNFENKNISMEQFE
           ****;**************************************;*.******* wap5.1     DMCGRYPNATEVNISGVPAVHLLAMKAVSSLRHLEVLTLGRGQLADNFFHALTDCHLLKS
melon      DMCGRYPNATEVNISGVPAVHLLAMKAVSSLRNLEVLTLGRGQLADNFFHALADCHLLKS
cucumber   DMCGRYPNATEVNISGVPAVHLLAMKAVSSLRNLEVLTLGRGQLADNFFHALADCHLLKS
           ****************************;;***************;;***** wap5.1     LTVNDSTLVNVTQEIPISHDRLRHLHLTKCRVIRISVRCPQLETLSLKRSNMAQAVLNCP
melon      LTVNDSTLVNVTQEIPISHDRLRHLHLTKCRVIRISVRCPQLETLSLKRSNMAQAVLNCP
cucumber   LTVNDSTLVNVTQEIPISHDGLRHLHLTKCRVIRISVRCPQLETLSLKRSNMAQAVLNCP
           ****************** ************************************* wap5.1     LLRDLDIGSCHKLSDAAIRSAAISCPQLESLDMSNCSCVSDETLREISANCPNLQLLNAS
melon      LLRDLDIGSCHKLSDAAIRSAAISCPQLESLDMSNCSCVSDETLREISGSCPNLQLLNAS
cucumber   LLRDLDIGSCHKLSDAAIRSAAISCPQLESLDMSNCSCVSDETLREISGSCPNLQLLNAS
           *********************************************.;.******* wap5.1     YCPNISLESVRLTMLTVLKLHSCEGITSASMTAISSSSGLKVLELDNCSLLTSVSLDLPH
melon      YCPNISLESVRLTMLTVLKLHSCEGITSASMTAISNSSSLKVLELDNCSLLTSVCLDLPH
cucumber   YCPNISLESVRLTMLTVLKLHSCEGITSASMTAISNSSSLKVLELDNCSLLTSVCLDLPD
           **********************************;**.***********.***** .****

wap5.1     LQNIRLVHCRKFSDLSLQSVKLSSIMVSNCPSLHRINITSNLLQKLVLKKQESLAKLVLQ
melon      LQNIRLVHCRKFSDLSLQSVKLSSIMVSNCPSLHRINITSNLLQKLVLKKQESLAKLVLQ
cucumber   LQNIRLVHCRKFSDLSLQSIKLSSIMVSNCPSLHRINITSNLLQKLVLKKQESLAKLILQ
           ******************;************************************;**

wap5.1     CPSLQDVDLTDCESLTNSICEVFSDGGGCPMLKSLVLDNCESLTAVRFCSSSLGSLSLVG
melon      CPSLQDVDLTDCESLTNSICEVFSDGGGCPMLKSLVLDNCESLTAVRFCSSSLGSLSLVG
cucumber   CPSLQDVDLTDCESLTNSLCEVFSDGGGCPMLKSLVLDNCESLTAVRFCSSSLGSLSLVG
           ****************** ;****************************************
```

Figure 4 (continued)

```
wap5.1     CRAITSLELQCPNLEQVSLDGCDHLERASFSPVGLRSLNLGICPKLNELKLEAPRMDLLE
melon      CRAITSLELQCPNLEQVSLDGCDHLERASFSPVGLRSLNLGICPKLNELKLEAPRMDLLE
cucumber   CRAITSLELQCPNLEKVSLDGCDRLERASFSPVGLRSLNLGICPKLNELKLEAPHMDLLE
           ***********:**.***************************.*** wap5.1     LKGCGGLSEAAINCPRLTSLDASFCGQLKDECLSATTASCPQIESLILMSCPSVGSEGLY
melon      LKGCGGLSEAAINCPRLTSLDASFCGQLKDECLSATTASCPQIESLILMSCPSVGSEGLY
cucumber   LKGCGGLSEAAINCPRLTSLDASFCSQLKDECLSATTASCPQIESLILMSCPSVGSEGLY
           ***********************.********************************* wap5.1     SLRCLLKLVVLDLSYTFLMSLQPVFESCIQLKVLKLQACKYLTDSSLEPLYKEDALPALQ
melon      SLRCLLKLVVLDLSYTFLMNLQPVFESCIQLKVLKLQACKYLTDSSLEPLYKEGALPALQ
cucumber   SLQCLLKLVVLDLSYTFLLNLQPVFESCIQLKVLKLQACKYLTDSSLEPLYKEGALPALQ
           .***********:.**************************.*.****** wap5.1     ELDLSYGTLCQSAIEELLACCTHLTHVSLNGCVNMHDLNWGCSIGQLSLSSIPIPLGQAT
melon      ELDLSYGTLCQSAIEELLACCTHLTHVSLNGCVNMHDLNWGCSIGQLSLSVIPIPLGQAT
cucumber   ELDLSYGTLCQSAIEELLACCTHLTHVSLNGCVNMHDLNWGCSIGQLSLSGIPIPLGQAT
           ************************************************  ****** wap5.1     LDEIEEPVAQPNRLLQNLNCVGCQNIRKVLIPPAARCFHLSSLNLSLSSNLKEVDVSCYN
melon      FDEIEEPVAQPNRLLQNLNCVGCPNIRKVLIPPAARCFHLSSLNLSLSSNLKEVDVSCYN
cucumber   FDEIEEPIAQPNRLLQNLNCVGCQNIRKVLIPPAARCFHLSSLNLSLSSNLKEVDVSCYN
           :****:*********** ********************************** wap5.1     LCFLNLSNCCSLEVLKLDCPRLTSLFLQSCNIEEEVVVAAVSRCSMLETLDVRLCPKISS
melon      LCFLNLSNCCSLEVLKLDCPRLTSLFLQSCNIEEEVVVAAVSKCSMLETLDVRFCPKISS
cucumber   LCVLNLSNCCSLEVLKLDCPRLTNLFLQSCNIEEEVVVAAVSKCSMLETLDVRFCPKISS
           .***************.***************.*****:**** wap5.1     ISMVQLRIACPSLKRIFSTLSPT
melon      ISMVQLRIACPSLKRIFSSLSPT
cucumber   ISMVQLRIACPSLKRIFSSLSPT
           ******************:****
```

PARTHENOCARPIC WATERMELON PLANTS

CROSS-REFERENCE TO RELATED APPLICATIONS

This application is a National Stage Entry of PCT/EP2021/077239, filed Oct. 4, 2021, which claims priority to European Application No. 20201337.1, filed Oct. 12, 2020, U.S. Provisional Application No. 63/111,898, filed Nov. 10, 2020, and U.S. Provisional Application No. 63/117,223, filed Nov. 23, 2020, the disclosures of each of which are hereby incorporated by reference in their entireties.

FIELD

The present invention is directed to parthenocarpic watermelon plants, producing seedless fruits without pollination of the female flowers, due to the presence of a mutant allele of a recessive gene referred to as WAP5.1. When the mutant allele is in homozygous form, the unpollinated flowers produce seedless fruits. However, when the flowers are pollinated, normal seeded fruits are produced. This trait is referred to as facultative parthenocarpy. The present invention also comprises methods for production of said plants and the use of the mutant allele, referred to as wap5.1, for the production of seedless watermelon fruits.

BACKGROUND

Most commercial seedless fruits have been developed from plants whose fruits normally contain numerous relatively large hard seeds distributed throughout the flesh of the fruit. Seedless fruits are e.g. known for watermelon, tomato, cucumber, eggplant, grapes, banana, citrus fruits, such as orange, lemon and lime. As consumption of seedless fruits is generally easier and more convenient, they are considered valuable.

Fruit development normally begins when one or more egg cells in the ovular compartment of the flower are fertilized by sperm nuclei from pollen.

Seedless fruits can result from two different phenomena. In some cases fruit develops without fertilization of the ovule by pollen, a phenomenon known as parthenocarpy. In other cases seedless fruits occur after pollination when seed (embryo and/or endosperm) growth is inhibited or the seed dies early, while the remainder of the fruit continues to grow (stenospermocarpy). In contrast to parthenocarpy, stenospermocarpy requires pollination for initiation of fruit growth.

Seedless orange fruits are an example for parthenocarpy. Some orange varieties (e.g. Navel) do not produce viable pollen. They however can be cross-pollinated with pollen from other varieties. In case only the male sterile variety is grown in an orchard, there will be no pollination and parthenocarp seedless fruits will be produced. Propagation of the respective orange trees is commonly done by cuttings followed by grafting to another rootstock.

Seedless bananas are triploid. Although pollination in some cases can be normal the vast majority of fruits is seedless. This is explained by the uneven sets of chromosomes (3×) leading to improper division of chromosomes during meiosis and as a consequence to the production of non-viable pollen. Without fertilization, triploid bananas are also able to set and develop seedless fruits. Even when pollination takes place, at most one in three hundred fruits comprises a few seeds. This may be due to the triploid pollen being non-viable, for the reasons explained. Therefore, banana plants can in general be seen to be parthenocarpic. Banana plants are commonly propagated asexually from side shoots or suckers at the base of the main stalk, which can be removed and replanted to continue the cultivar. Growers also propagate bananas by means of tissue culture, in particular for producing disease free material.

Seedless cucumber, seedless squash and seedless eggplant are examples for crops which can produce seedless fruits without pollination (parthenocarpy), e.g. under conditions where pollination is impaired (e.g. low temperatures). Nevertheless, commercial quality fruit can be produced under these conditions. All these crops however can produce seed bearing fruits upon pollination. Therefore, these crops are facultative parthenocarpic. Propagation of the crops can be done by self- or cross pollination, in vitro propagation, and grafting.

From tomato mutants it is also known that they can produce seedless fruits under conditions where normal pollination/fertilization is impaired (e.g. under circumstances of low temperature). Thus, these mutants are also facultative parthenocarpic. Mutants known for showing this phenotype are pat, pat-2 and the pat-3/pat-4 system. The genes underlying these mutations are not known and the pat-3/pat-4 system seems to depend on multiple loci.

Parthenocarpy has also been introduced into several plant species by means of genetic modification. Expression of a bacterial tryptophan monooxygenase (iaaM) conferring auxin synthesis under control of the ovule and placenta specific DefH9 promoter did induce parthenocarpy in cucumbers (Yin et al., 2006, Clular & molecular Biotech. Letters 11, 279-290), eggplant (Acciarri et al., 2002, BMC Biotech. 2(4)), tomato (Rotino et al., 2005, BMC Biotech. 5(32)) and tobacco.

These transgenic plants demonstrate the importance of plant hormones in seed and fruit development. That seed and fruit development are besides other factors strongly under control of several plant hormones is well known in the art. Parthenocarpy, including the logical consequence of fruit's seedlessness, can also be induced e.g. by exogenous application of plant hormones, in particular auxin or gibberellin (Ruan et al., Trends in Plant Sci. 17(11), 1360-1385).

Seedless watermelons produced currently by breeders are examples for stenospermocarp crops. Normal watermelon plants are diploid (2n). Seedless fruit producing watermelons are hybrids produced by crossing a male diploid (2n) watermelon plant with a female tetraploid (4n) watermelon plant. The resulting F1 hybrid seeds are triploid (3n). Induction of fruit setting of the triploid F1 hybrid plants requires pollination. As the triploid (3n) F1 hybrid plants do not produce fertile pollen, so called pollinator or polliniser plants have to be planted in the same field. The pollinator plants are diploid (2n). Generally a ratio of pollinator to hybrid plants of around 1 to 3 must be planted in a given scheme for providing sufficient pollen for pollinating all the F1 hybrid plants. The cross-pollination between the diploid (2n) pollinator and the flowers of the female triploid (3n) hybrid plant induces fruit set and leads to the production of seedless triploid fruits on the triploid hybrid plant. The diploid (2n) and tetraploid (4n) parents of the F1 hybrid each produce seed bearing fruits and can both be propagated independently from each other by self-pollination.

Seedless grapes can be produced from plants being either parthenocarp or stenospermocarp. The variety Black Corinth is parthenocarp, whereas Sultanina is stenospermocarp. Vine plants are in general propagated by cuttings and successive grafting to another rootstock.

Irregularities in meiosis can be a factor leading to plants producing seedless fruit. An example for plants producing seedless fruits is given in Zhang et al. (2012, Scientia Horticulture 140, 107-114), disclosing seedless watermelons. A male and female sterile (MFS) mutant was obtained from the progeny of a F1-hybrid after irradiation of its seeds with gamma-rays. Pollen from the MFS mutant was not viable at all. Seedless fruits are produced by the MFS plants, when pollinated with pollen from male fertile plants. The MFS watermelon plant therefore can be classified as being stenospermocarpic. Ovules were also nearly entirely nonviable, as almost no seeds were produced upon cross-pollination of MFS mutants with pollen from different male fertile plants. Incomplete synapsis and abnormal separation of chromatids during meiosis were observed in the MFS mutant and seen to be the cause of male and female sterility. The genes responsible for the effects present in the MFS mutant have not been identified but it seems likely that the phenotype in the MFS mutant is due to a single recessive gene.

From above discussion it is evident, that the factors determining if plants produce seedless fruits are multiple in nature and can reside in several, e.g. morphologic, physiologic and/or genetic causes.

For producing seedless fruits in stenospermocarpic crops, such as triploid (3n) watermelon plants, a female flower part of a plant must be pollinated. The stenospermocarpic crops grown today are male sterile. As a consequence, besides the female plant, a different male fertile plant (pollinator or polliniser) has to be grown in addition in the same field. As the area used for the pollinator plants is at the expense of the area which is available for the seedless fruit producing female plants, the yield per area under cultivation is reduced. In general, the pollinator plants are normal plants which can also be self-pollinated. Fruits produced by pollinator plants however do produce seeds. In watermelon, the pollinator plants are normally diploid (2n), which upon self-pollination produce seeded fruits, which may in some instances also be harvested and sold separately (see WO2012069539). For commercial reasons these seeded fruits from the pollinator plants must not be mixed with the seedless fruits. Therefore, it has to be ensured, that seedless fruits and seeded fruits are separated upon or after harvest, which may make machine harvesting difficult or impossible or require a further processing step after harvesting. Those additional precautions to be taken increase the input costs in seedless fruit production. In addition, pollinator plants are developed so that they flower and produce sufficient viable pollen at the same time the female plant flowers and its stigma can accept pollen for the induction of fruit set. Thus, the pollinator plant has to fit with the female plant producing seedless fruit in respect to flowering and fertilisation time. If flowering time of the pollinator pant and the respective female plant is not sufficiently synchronised, pollination will not take place or only take place in an insufficient amount of cases. As a result fewer fruits are produced by the stenospermocarpic female plant. Furthermore, it is well known in the art that climate conditions, like rain, heat etc., may influence pollen production of a polliniser plant differently than stigma fertility time of the genotypic different female plant. Therefore, climate conditions can also lead to asynchrony of fertility time of pollinator and female plant with the effect of lowering the yield.

The present inventors have found that mutating a single recessive gene in cultivated watermelon, referred herein to as the WAP5.1 gene, results in the watermelon plants developing seedless fruits when the flowers are not pollinated, i.e. parthenocarpy. If the flowers are pollinated, the fruits that develop produce normal viable seeds. This type of parthenocarpy is, therefore, referred to as facultative parthenocarpy, as it is only seen in the absence of pollination. The WAP5.1 gene is, therefore, responsible for facultative parthenocarpy in watermelon. Thus, when the mutant wap5.1 allele is present in homozygous form in a diploid watermelon plant, indicated herein as wap5.1/wap5.1, the plants are facultative parthenocarp and produce seedless fruits from non-pollinated flowers and normal seeded fruits from pollinated flowers.

This gene has great advantages in diploid watermelons, especially if combined with male sterility (MS) to ensure absence of pollination of the female flowers (as the male flowers produced on the plant are sterile) or combined with the emb1 mutant (e.g. in homozygous form, emb1/emb1) to ensure that, in case pollination does occur, the fruits are seedless due to the homozygous presence of the emb1 mutant in the plant. The emb1 mutant is a stenospermocarpy mutant, resulting in seedless fruits being produced upon pollination. Seeds comprising an emb1 mutant allele have been deposited by Nunhems B.V. on 27 Jan. 2016 under accession number NCIMB42532.

The WAP5.1 gene has also great advantages in triploid watermelons having e.g. two or three copies of the mutant allele because there is no need anymore to interplant such triploid watermelon plants with a pollenizer plant (which is normally needed to induce fruit set in normal tripoids, having three copies of the wild type WAP5.1 allele). These parthenocarp triploid plants produce seedless fruits without the need for pollination to induce fruit set. Therefore, basically the stenospermocarp nature of the normal triploid watermelons is changed into parthenocarpy. Yield of seedless triploid fruits is thereby increased greatly, as the pollenizer plants are not required anymore in a field and the entire field can comprise triploid watermelon plants.

In a population of mutagenized M2 diploid watermelon plants grown in insect-proof greenhouses so that no pollination could occur, a plant producing seedless fruits from un-pollinated female flowers (see FIG. 1) was observed when screening more than 20.000 plants. The fruits contained only some traces of teguments of maternal origin, similar to what is seen in known triploid seedless fruits. Genetic analysis showed that the trait segregated as a single recessive gene. The gene was designated WAP5.1, and the mutant allele was designated wap5.1.

Figure 3:
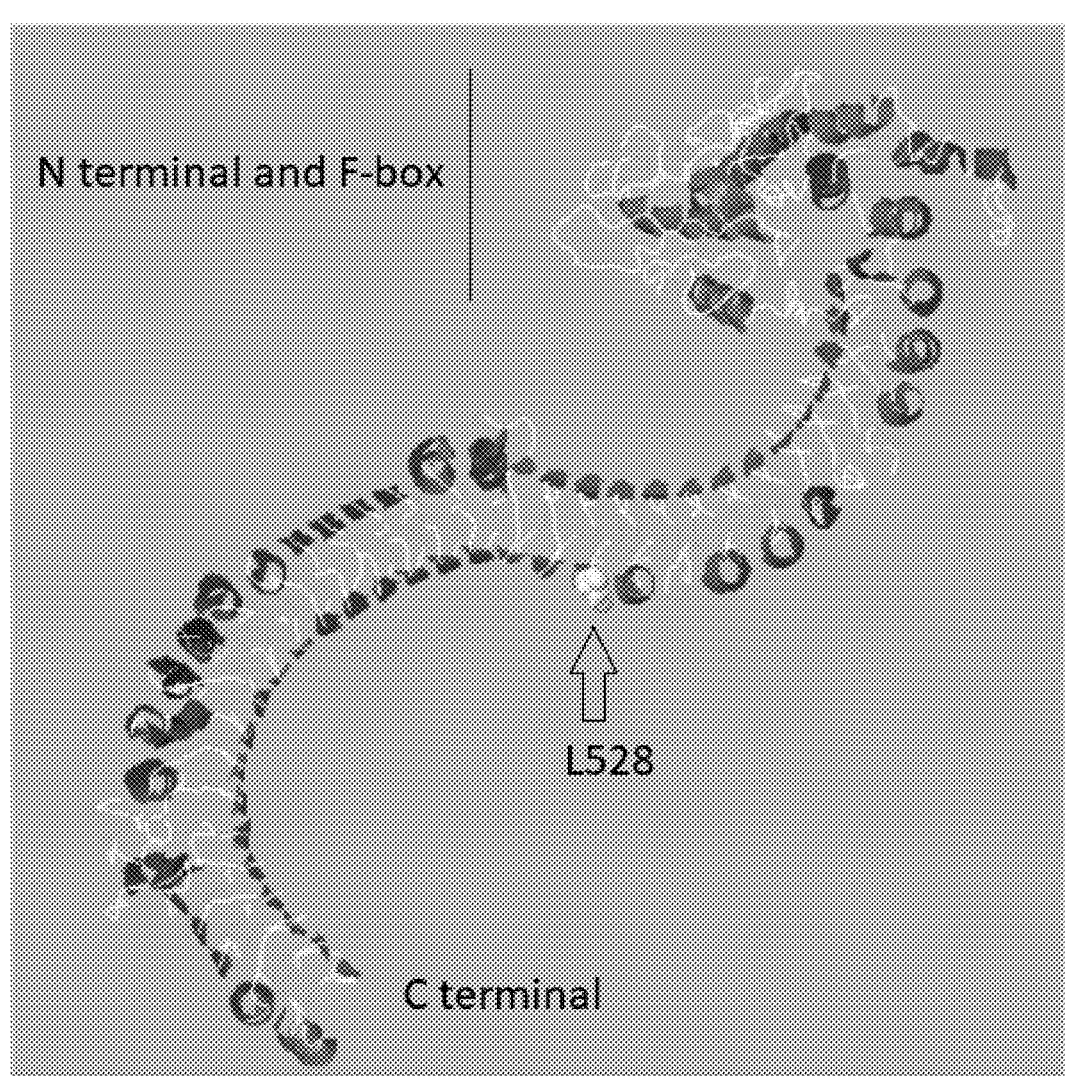
Figure 3:
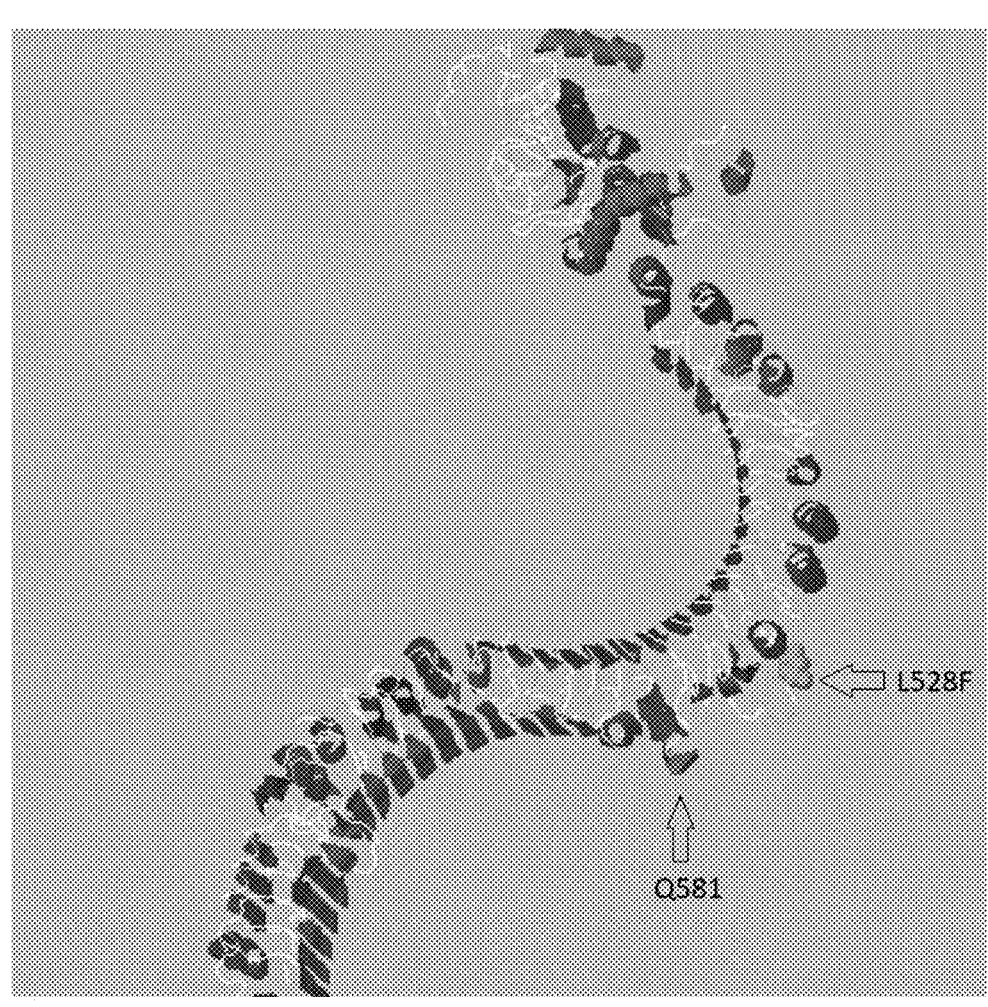

Several F2 mapping populations were generated with different genetic backgrounds from a single plant line, which was able to produce parthenocarpic fruits. Two F2 populations were phenotyped and genotyped, derived from two different backgrounds. A QTL was mapped to a 0.47 Mb region on chromosome 5, which contained two mutations, one of which in an intergenic region and another in a gene, changing a highly conserved amino acid from leucine to phenylalanine (L528F). FIG. 2 shows the amino acid sequences of the wild type and mutant WAP5.1 proteins of SEQ ID NO: 1 and SEQ ID NO: 4, respectively. The solid lined box shows the highly conserved F-box domain and the dashed-line box shows the highly conserved LRR domain (Leucine Rich Repeat domain). FIG. 3A shows the 3-dimensional structure of the wild type WAP5.1 protein, showing the highly ordered structure of the LRR-domain at the C-terminal of the protein. The F-box is at the N-terminal of the protein, and the remaining part of the protein following the F-box (i.e. the LRR-domain) is folded into a kind of tail structure, by helices, beta-bridges and coils. The position of amino acid Leucine L528, which was found to be replaced by Phenylalanine (i.e. L528F mutation) in the mutant wap5.1 protein is indicated in FIG. 3A and is part of a coil region of the LRR-domain. FIG. 3B shows the 3-Dimensional structure of the L528F mutant, wherein the LRR-domain does not fold properly into the tail structure and a whole stretch of amino acids (including e.g. Q581) appears to stick out in loops. The mutant protein, which does not have a proper folding (3-D structure) is thought to either not function in vivo at all, or to have impaired in vivo function compared to the wild type protein, thereby leading to the phenotype of (facultative) parthenocarpy when the mutant is in homozygous form.

In the genome of watermelon the wild type gene is found on chromosome 5, e.g. in the Charleston Grey V2 genome found at cucurbitgenomics.org the WAP5.1 gene is labelled ClCG05G015740.1 and is found on the plus strand starting at nucleotide 27630305 and ending at nucleotide 27637763. It is said to encode an "F-box/LRR repeat" protein, but no in vivo function or phenotype is known. In the watermelon line in which the mutant was generated (referred to as TY-line), there is a single amino acid which is different from the wild type WAP5.1 protein of the Charleston Grey V2 genome. This single amino acid is amino acid number 51, which is a Glycine (G) in the WAP5.1 protein encoded by the gene of the Charleston Grey genome, but an Arginine (R) in the protein encoded by the TY-line. The wild type WAP5.1 protein therefore either has e.g. the sequence of SEQ ID NO: 1 (G51) or of SEQ ID NO: 9 (R51). When referring to a wild type WAP5.1 protein of watermelon herein (or a gene encoding a wild type WAP5.1 protein), therefore, in one aspect the protein of SEQ ID NO: 1 or the protein of SEQ ID NO: 9 is referred to, or a wild type protein comprising at least 95%, 96%, 97%, 98%, 99% identity to SEQ ID NO: 1 or 9. The R51 is also found in other watermelons, such as the variety 97103 (V2, cucurbitgenomics.org). In this genome the gene is called Cla97C05G096710 and is located on chromosome 5 at nucleotide position 25813434 to 25820323 (+strand). The wild type WAP5.1 protein encoded by this gene is 100% identical to the wild type protein of the TY-line, of SEQ ID NO: 9.

The orthologous proteins were obtained from public databases for cucumber and melon, as shown in FIG. 4 (with herein SEQ ID NO: 2 being the cucumber WAP5.1 ortholog and SEQ ID NO: 3 being the melon WAP5.1 ortholog). What can be seen in FIG. 4 is that the F-box domain and the LRR-domain are both highly conserved between these three proteins, and the N-terminal amino acid sequence preceding the F-box is more variable, i.e. less conserved. The F-box domain is 100% identical between the watermelon, melon and cucumber WAP5.1 proteins (see FIG. 4) and the LRR-domain is 96.2% identical between watermelon and cucumber, 98% between watermelon and melon and 97.8% between cucumber and melon (in a pairwise alignment using Emboss-Needle). This is in line with studies of known F-box/LRR domain proteins, see e.g. the review on F-box proteins in plants (Xu et al. 2009, PNAS vol. 106, no. 3, pp 835-840) and a study on the *Arabidopsis* SLOMO F-box/LRR protein (Lohmann et al., 2010, The Plant Cell, Vol. 22: 335-348). Interestingly, Lohmann et al. compared three different SLOMO mutants, slomo-1, slomo-2 and slomo-3, whereby slomo-1 had a single amino acid substitution in the LRR-domain, slomo-2 had a premature STOP-codon preceding in the LRR-domain and slomo-3 had a T-DNA insertion in the first intron, preventing protein production (see e.g. supplement FIG. 2A). While all three mutants are described as having loss of function, it is also mentioned that the single amino acid substitution in the LRR-domain has the strongest phenotype. A single amino acid replacement can, thus, lead to a mutant protein which results in a loss of function or such a reduced function that the phenotype is strongly expressed, probably due to the 3-dimensional structure (such as correct folding and/or interaction with other proteins or substrates) of the LRR-domain being affected.

Further watermelon plants containing mutations in the WAP5.1 protein were generated and identified in a TILLING population and it will be confirmed whether each of these also confer facultative parthenocarpy in watermelon when the mutant allele is in homozygous form. As the incorrect protein folding of the L528F mutant appears responsible for the phenotype, it is reasonable to assume that any mutation leading to incorrect protein folding or incorrect interaction with substrates or other proteins, will lead to a reduced function or loss of function of the protein and thereby to facultative parthenocarpy when the mutant allele is in homozygous form. Clearly, also mutations which lead to truncations e.g. of all or part of the LRR domain will lead to a reduced function or loss of function of the protein and thereby to facultative parthenocarpy when the mutant allele is in homozygous form. Similarly, a mutant wap5.1 allele comprising one or more mutations in a regulatory region of the protein, such as a promoter or enhancer, is expected to result in reduced or no active wild type protein being made, which would thereby equally result in facultative parthenocarpy when the mutant allele is in homozygous form.

In total 9 mutant alleles have been identified so far in watermelon, as shown in Table 1. Whether the resulting mutant protein is predicted to have a changed 3-dimension structure compared to the wild type WAP5.1 protein has been estimated using RaptorX Contact Prediction (also referred to as RaptorX Structure Prediction herein).

TABLE 1

| SNP (single nucleotide polymorphism between the wild type and the mutant coding sequence) | effect on WAP5.1 protein (amino acid substitution or premature STOP codon) | Position in protein | 3-dimensional structure affected as predicted by RaptorX Structure Prediction* |
|---|---|---|---|
| C/T | L528F | In LRR-domain | Yes (see FIG. 3B) |
| C/T | A266V | In F-box domain | Not clear, both A and V are part of a helical structure. Also both A and V are hydrophobic and both have a neutral side chain. In vivo analysis needed. |

TABLE 1-continued

| SNP (single nucleotide polymorphism between the wild type and the mutant coding sequence) | effect on WAP5.1 protein (amino acid substitution or premature STOP codon) | Position in protein | 3-dimensional structure affected as predicted by RaptorX Structure Prediction* |
|---|---|---|---|
| G/A | E287K | Between F-box domain and LRR-domain | |
| C/T | A257V | In F-box domain | Not clear, both A and V are part of a helical structure. Also both A and V are hydrophobic and both have a neutral side chain. In vivo analysis needed. |
| C/T | Q333Stop | In LRR-domain | Yes (truncation) |
| G/A | W274Stop | In F-box domain | Yes (truncation) |
| A/G | D209V | In N-terminal, preceding F-box | Not clear, both D and V are part of a helical structure, but V is hydrophobic, while D is hydrophilic; in vivo analysis needed |
| C/T | P308L | In LRR-domain | To be determined |
| G/A | G330E | In LRR domain | To be determined |

*world wide web at //raptorx.uchicago.edu/ContactMap/

As mentioned, it is expected that at least those mutant proteins which have an amino acid substitution in the highly conserved F-box or in the LRR-domain compared to the wild type protein, or which have a or premature STOP codon which results in the absence of all or part of the F-box or LRR-domain, and/or which are predicted to show a modified 3-dimensional structure/incorrect 3-dimension folding compared to the wild type WAP5.1 protein, will show a phenotype when the mutant allele is in homozygous form (i.e. the plants will show facultative parthenocarpy), i.e. will produce seedless fruits without pollination and seeded fruits when pollinated when the mutant alleles are in homozygous form, e.g. in a diploid plant. Whether this is indeed the case can be tested by generating plants homozygous for the mutant wap5.1 allele, growing them in the absence of pollination, and analysing whether they produce seedless fruits under these circumstances and whether they produce seeded fruits when pollinated. Obviously, other mutant wap5.1 alleles can be generated by e.g. random mutagenesis or targeted mutagenesis in the watermelon, cucumber or melon WAP5.1 gene.

The above mutants, or other mutants in the endogenous WAP5.1 gene of a plant, can be generated by e.g. random mutagenesis or targeted mutagenesis, such as CRISPR-based methods. A review of targeted gene editing is provided e.g. by Erpen-Dalla Corte et al. in Plants 2019, 8, 601 (doi:10.3390/plants8120601) and by Bed Prakash Bhatta and Subas Malla in Plants 2020, 9, 1360; doi:10.3390/plants9101360. Crispr-based editing has also already been carried out in watermelon and other cucurbit crops and can thus be used by the skilled person to edit the endogenous WAP5.1 gene of watermelon, melon or cucumber, or other cucurbit species comprising an orthologous gene.

Regarding mutations in the conserved F-box domain and/or the LRR-domain (or in other parts of the protein), in one aspect especially mutations which lead to amino acid replacements, whereby the properties of the wild type amino acid and the replaced amino acid are different, are one aspect herein, as such different amino acid properties will reduce or abolish the proper folding and/or the normal function of the protein or of the domain. So, for example a replacement of a non-polar amino acid by a polar amino acid (comprising a hydrophilic side chain), or vice versa, or the replacement of an amino acid having a charged side chain with a non-charged or differently charged side-chain. Non-polar amino acids are Alanine (A or Ala), Cysteine (C or Cys), Glycine (G or Gly), Isoleucine (I or Ile), Leucine (L or Leu), Methionine (M or Met), Phenylalanine (F or Phe), Proline (P or Pro), Tryptophan (W or Trp), Valine (V or Val). Polar amino acids are Arginine (R or Arg), Asparagine (N or Asn), Aspartate (D or Asp), Glutamate (E or Glu), Glutamine (Q or Gln), Histidine (H or His), Lysine (K or Lys), Serine (S or Ser), Threonine (T or Thr), Tyrosine (Y or Tyr).

Thus, in one aspect any one (or more) of the 24 non-polar amino acids of the F-box domain is replaced by a polar amino acid and/or any one (or more) of the 17 polar amino acids of the F-box domain is replaced by a non-polar amino acid. The resulting mutant allele can then be tested for it's function by generating a plant homozygous for the mutant allele and analysing the phenotype. If the mutant allele results in the plant becoming facultative parthenocarpic, then the mutant allele is an allele encodes a mutant wap5.1 protein having reduced function or no function in vivo.

In one aspect the watermelon WAP5.1 gene is the gene encoding a WAP5.1 protein, wherein a WAP5.1 protein is the protein of SEQ ID NO: 1 or SEQ ID NO: 9, or a protein comprising at least 94%, 95%, 96%, 97%, 98% or 99% sequence identity to SEQ ID NO: 1 or SEQ ID NO: 9. The watermelon WAP5.1 gene may also be referred to as ClWAP5.1, for *Citrullus lanatus* WAP5.1. The wild type protein of SEQ ID NO: 1 is the protein found in e.g. the Charleston Grey genome, but other cultivated watermelons, such as the line TY used herein or the east Asian variety 97103, the genome of which was also sequenced and is provided on cucurbitgenomics.org as V1 and V2, contain small differences in 1 or 2 amino acids, i.e. the protein is 99.9% or 99.8% identical to that of SEQ ID NO: 1. Therefore, other cultivated watermelons contain a WAP5.1 gene that encodes a wild type (functional) WAP5.1 protein having at least 94%, 95%, 96%, 97%, 98% or 99% or 99.5% or 99.8% or 99.9% sequence identity to SEQ ID NO: 1. An example is the gene which encodes the protein of SEQ ID NO: 9, which differs from the protein of SEQ ID NO: 1 in only a single amino acid:amino acid 51. SEQ ID NO: 1 and SEQ ID NO: 9 are thus 99.9% identical in amino acid sequence and are both functional (wild type) WAP5.1 proteins. Watermelon plants comprising the genes encoding these wild type proteins are not parthenocarpic, i.e. they produce fruits only following pollination.

In another aspect the cucumber WAP5.1 gene is the gene encoding a WAP5.1 protein, wherein a WAP5.1 protein is the protein of SEQ ID NO: 2 or a protein comprising at least 94%, 95%, 96%, 97%, 98%, 99%, 99.5%, 99.8% or 99.9% sequence identity to SEQ ID NO: 2. The cucumber WAP5.1 gene may also be referred to as CsWAP5.1, for *Cucumis sativus* WAP5.1.

In another aspect the melon WAP5.1 gene is the gene encoding a WAP5.1 protein, wherein a WAP5.1 protein is the protein of SEQ ID NO: 3 or a protein comprising at least 94%, 95%, 96%, 97%, 98%, 99%, 99.5%, 99.8% or 99.9% sequence identity to SEQ ID NO: 3. The melon WAP5.1 gene may also be referred to as CmWAP5.1, for *Cucumis melo* WAP5.1.

In one aspect of the invention a plant or plant cell is provided, characterized in that the plant or plant cell has decreased activity of a WAP5.1 protein compared to a corresponding wild type plant cell, wherein the WAP5.1 protein of the wild type plant cell is encoded by nucleic acid molecules selected from the group consisting of:

a) nucleic acid molecules, which encode a protein with the amino acid sequence given under SEQ ID NO: 1 or SEQ ID NO: 9 (watermelon) or SEQ ID NO: 2 (cucumber) or SEQ ID NO: 3 (melon);
   b) nucleic acid molecules, which encode a protein, the sequence of which has an identity of at least 94%, 95%, 96%, 97%, 98%, 99%, 99.5%, 99.8% or 99.9% with the amino acid sequence given under SEQ ID NO: 1 or SEQ ID NO: 9 (watermelon) or SED ID NO: 2 (cucumber) or SEQ ID NO: 3 (melon);
   c) nucleic acid molecules, which encode a protein, the sequence of which has an identity of at least 94%, 95%, 96%, 97%, 98%, 99%, 99.5%, 99.8% or 99.9% with the amino acid sequence given under SEQ ID NO: 1 or SEQ ID NO: 9 (watermelon) or SED ID NO: 2 (cucumber) or SEQ ID NO: 3 (melon) and wherein the protein comprises the amino acid sequence of the F-box domain, i.e. amino acids 237 to 277 of SEQ ID NO: 1 or of SEQ ID NO: 9 (amino acids LTD-DLLHMVFSFLDHINLCRAAIVCRQWQAASA-HEDFWRCL—SEQ ID NO: 13) and comprises an LRR-domain, whereby the LRR-domain is the region from amino acid 291 to 1033 of SEQ ID NO: 1 or of SEQ ID NO: 9 (watermelon), or from amino acid 298 to 1040 of SEQ ID NO: 2 (cucumber), or from amino acid 301 to 1043 (melon).

The decreased activity of the WAP5.1 protein is caused by a mutant wap5.1 allele. Decreased activity may be caused by a knock-down or knock-out of the expression of the mutant wap5.1 allele (e.g. through a mutation in the promoter or other regulatory sequence) or through the mutant wap5.1 allele encoding a loss-of-function or decreased-function WAP5.1 protein (mutant WAP5.1 protein).

In one aspect the mutant wap5.1 allele encodes a mutant WAP5.1 protein having decreased function or loss-of-function compared to the wild type protein, e.g. the mutant WAP5.1 protein comprises one or more amino acids replaced, deleted or inserted compared to the wild type protein. In one aspect the mutant WAP5.1 protein comprises one or more amino acids replaced, deleted or inserted in the conserved "F-box" domain of the protein and/or in the conserved LRR-domain of the protein. In a preferred aspect, at least one amino acid in the conserved "F-box domain" and/or in the "LRR-domain" is replaced by another amino acid or by a STOP codon, resulting in a loss of function or decreased function protein and facultative parthenocarpy when the allele is in homozygous form (when no wild type allele is present in the diploid plant or plant cell). In another aspect one or more amino acids of the conserved "F-box domain" and/or of the "LRR-domain" are missing, e.g. through a mutation causing a premature STOP codon, resulting in a loss of function or decreased function protein and facultative parthenocarpy when the allele is in homozygous form (when no wild type allele is present in the diploid plant or plant cell).

In one aspect the mutant wap5.1 allele encodes a mutant WAP5.1 protein having a 3-dimensional structure/protein folding which is modified compared to the 3-dimensional structure/protein folding compared to the wild type WAP5.1 protein, as can be seen by comparing the 3-dimension structures of the wild type protein and mutant protein using e.g. the RaptorX Contact Prediction tool. Especially amino acid changes (substitutions or deletions) which affect the proper folding of the LRR-domain can be easily seen. The wild type LRR-domain folds into a long tail-like structure as shown in FIG. 3A. Any improper folding becomes easily visible, as e.g. shown in FIG. 3B. Also, absence of all or part of the LRR-domain in a truncated WAP5.1 protein is encompassed herein in being a protein having a modified 3-dimensional structure/protein folding compared to the wild type protein. As the LRR-domain is highly structured and conserved, any changes in its structure are predicted to lead to a loss-of function or reduced function of the protein and thereby to the in vivo phenotype (facultative parthenocarpy) when the mutant allele is in homozygous form in a diploid plant.

In one aspect the mutant allele encodes a mutant protein wherein amino acid 528, 266, 287, 257, 333, 274, 209, 308 or 330 of SEQ ID NO: 1 or of SEQ ID NO: 9, or the equivalent amino acid in a sequence comprising at least 94%, 95%, 96%, 97%, 98% or 99% identity to SEQ ID NO: 1 or to SEQ ID NO: 9, or the equivalent amino acid in SEQ ID NO: 2 or 3, is deleted or is replaced by a different amino acid or by a Stop codon. The equivalent amino acid can be identified by pairwise alignment (e.g. using the program Needle) with e.g. SEQ ID NO: 1 or SEQ ID NO: 9, see e.g. FIG. 4, wherein the mentioned watermelon amino acids and the equivalent cucumber and melon amino acids are shown in bold.

In one aspect L528 of the watermelon protein (or the equivalent amino acid in a sequence comprising at least 94% 95%, 96%, 97%, 98% or 99% identity to SEQ ID NO: 1 or to SEQ ID NO: 9, or the equivalent amino acid in SEQ ID NO: 2 or 3), is replaced by F, and/or A266 of the watermelon protein (or the equivalent amino acid in a sequence comprising at least 94% or 95% identity to SEQ ID NO: 1, or the equivalent amino acid in SEQ ID NO: 2 or 3) is replaced by V, and/or E287 of the watermelon protein (or the equivalent amino acid in a sequence comprising at least 94% 95%, 96%, 97%, 98% or 99% identity to SEQ ID NO: 1 or to SEQ ID NO: 9, or the equivalent amino acid in SEQ ID NO: 2 or 3) is replaced by K, and/or A257 of the watermelon protein (or the equivalent amino acid in a sequence comprising at least 94%95%, 96%, 97%, 98% or 99% identity to SEQ ID NO: 1 or to SEQ ID NO: 9, or the equivalent amino acid in SEQ ID NO: 2 or 3) is replaced by V, and/or Q333 of the watermelon protein (or the equivalent amino acid in a sequence comprising at least 94% 95%, 96%, 97%, 98% or 99% identity to SEQ ID NO: 1 or to SEQ ID NO: 9, or the equivalent amino acid in SEQ ID NO: 2 or 3) is replaced by a stop codon, and/or W274 of the watermelon protein (or the equivalent amino acid in a sequence comprising at least 94%95%, 96%, 97%, 98% or 99% identity to SEQ ID NO: 1 or to SEQ ID NO: 9, or the equivalent amino acid in SEQ ID NO: 2 or 3) is replaced by a STOP codon, and/or D209 of the watermelon protein (or the equivalent amino acid in a sequence comprising at least 94% 95%, 96%, 97%, 98% or 99% identity to SEQ ID NO: 1 or to SEQ ID NO: 9, or the equivalent amino acid in SEQ ID NO: 2 or 3) is replaced by V, and/or P308 of the watermelon protein (or the equivalent amino acid in a sequence comprising at least 94%95%, 96%, 97%, 98% or 99% identity to SEQ ID NO: 1 or to SEQ ID NO: 9, or the equivalent amino acid in SEQ ID NO: 2 or 3) is replaced by L, and/or G330 of the watermelon protein (or the equivalent amino acid in a sequence comprising at least 94% 95%, 96%, 97%, 98% or 99% identity to SEQ ID NO: 1 or to SEQ ID NO: 9, or the equivalent amino acid in SEQ ID NO: 2 or 3) is replaced by E.

SUMMARY

A cultivated watermelon, cucumber or melon plant or plant part is provided comprising at least one copy of a mutant allele of a gene named WAP5.1, said mutant allele conferring facultative parthenocarpy when the mutant allele is in homozygous form.

In one aspect the gene is located on chromosome 5 of the watermelon genome, especially the gene is located in a region starting at base pair 27630305 and ending at base pair 27637763 of chromosome 5, e.g. of the Charleston Grey chromosome or in a region starting at base pair 25813434 and ending at base pair 25820323 of chromosome 5, e.g. of the watermelon 97103 V2 chromosome.

In one embodiment the plant or plant part comprising the mutant allele of the WAP5.1 gene is diploid, tetraploid, triploid or polyploid. Preferably the mutant allele is present in two copies in a diploid plant or plant part, in four copies in a tetraploid plant or plant part or in one, two or three copies in a triploid plant or plant part.

Optionally the plant or plant part which comprises the mutant allele of the WAP5.1 gene further comprises a gene conferring male sterility or a gene conferring stenospermo-carpy, such as the gene described in WO2017202715 and/or in WO2019238832.

Optionally the plant or plant part which comprises the mutant allele of the WAP5.1 gene further comprises a gene conferring parthenocarpy, e.g. the gene described in WO2018/060444.

The plant part comprising the mutant allele of the WAP5.1 gene may be a cell, a flower, a leaf, a stem, a cutting, an ovule, pollen, a root, a rootstock, a scion, a fruit, a proto-plast, an embryo, an anther.

Also encompassed is a vegetatively propagated water-melon, cucumber or melon plant propagated from such a plant part comprising at least one mutant allele of the WAP5.1 gene.

Likewise a seed from which a plant of the invention can be grown is provided.

Further, a seedless fruit produced by a plant according to the invention is provided.

A method of producing seedless watermelon, cucumber or melon fruits is provided, said method comprising growing a diploid plant comprising two copies of a mutant allele of a WAP5.1 gene and harvesting the fruits produced by said plants. In particular the fruits develop without pollination of the female flowers, while seeded fruits are produced upon pollination of the flowers.

A method of producing seedless watermelon fruits is provided, said method comprising growing a triploid plant comprising one, two or three copies of a mutant allele of a WAP5.1 gene and harvesting the fruits produced by said plants. In particular the fruits develop without pollination of the female flowers, i.e. no pollen is required to induce fruit development.

A method for growing watermelon plants is provided, comprising growing a triploid watermelon plant comprising one, two or three copies of a mutant allele of a WAP5.1 gene, especially in a field without pollenizer plants, and optionally harvesting the seedless watermelon fruits from said plants.

A method for production of a facultative parthenocarpic cultivated watermelon, cucumber or melon plant is provided comprising the steps of:

a) introducing mutations in a population of watermelon, cucumber or melon plants; or providing a population of mutant plants (e.g. a TILLING population, e.g. M2, M3, M4 or further generation);

b) selecting a plant producing seedless fruits without pollination of the female flowers and producing a seeded fruit after pollination of the female flowers;

c) optionally verifying if the plant selected under b) comprises a mutant allele of a WAP5.1 gene; and d) optionally growing the plants obtained under c).

A method for production of a facultative parthenocarpic cultivated watermelon, cucumber or melon plant is provided comprising the steps of:

a) introducing mutations in a watermelon, cucumber or melon plant; or providing a population of mutant plants (e.g. a TILLING population, e.g. M2, M3, M4 or further generation);

b) selecting a plant comprising a mutant allele of the WAP5.1 gene;

c) optionally selling the selected plant to generate a plant homozygous for the mutant allele of the WAP5.1 gene;

d) optionally growing the plants.

A watermelon, cucumber or melon plant or fruit produced by the method is encompassed herein.

Use of a facultative parthenocarpic watermelon, cucumber or melon plant for producing seedless watermelon, cucumber or melon fruits, preferably without pollination of the female flowers of the plant is also an aspect of the invention.

Use of a mutant wap5.1 allele of a WAP5.1 gene as described herein for producing facultative parthenocarpic watermelon, cucumber or melon plants is also an aspect of the invention.

A method for production of a cultivated watermelon, cucumber or melon plant producing seedless fruits in the absence of pollination and seeded fruits in the presence of pollination is provided comprising the steps of:

a) introducing random or targeted mutations into one or more watermelon, cucumber or melon plants, plant parts or seeds; or providing a population of mutant plants or seeds (e.g. a TILLING population, e.g. M2, M3, M4 or further generation), b) selecting a plant comprises a mutant allele of a wap5.1 gene, e.g. a mutant allele which produces significantly reduced or no wild type WAP5.1 protein (e.g. a knock-out allele) or which encodes a protein which comprises one or more amino acids deleted, replaced, inserted or duplicated compared to the wild type protein, c) optionally removing any transgenic construct (e.g. CRISPR construct) from the plant, and/or d) optionally generating a plant homozygous for the mutant allele and analyzing whether seedless fruits develop in the absence of pollination and seeded fruits develop in the presence of pollination.

A method for selecting or identifying watermelon, cucumber or melon plants, seeds or plant parts is provided comprising the steps of:

a) analyzing whether the genomic DNA of the plant or plant part comprises a mutant allele and/or comprises a wild type allele of the WAP5.1 gene in their genome and optionally b) selecting a plant or plant part comprising one or two copies of a mutant allele of the wap5.1 gene in the genome, wherein the wild type allele of the watermelon WAP5.1 gene encodes the protein of SEQ ID NO: 1 or of SEQ ID NO: 9 (or a wild type protein comprising at least 95%, 96%, 97%, 98%, 99% identity to SEQ ID NO: 1 or SEQ ID NO:9), the wild type allele of the cucumber WAP5.1 gene encodes the protein of SEQ ID NO: 2 (or a wild type protein comprising at least 95%, 96%, 97%, 98%, 99% identity to SEQ ID NO: 2) and the wild type allele of the melon WAP5.1 gene encodes the protein of SEQ ID NO: 3 (or a wild type protein comprising at least 95%, 96%, 97%, 98%, 99% identity to SEQ ID NO: 3).

Step a) can be carried out in various ways, using e.g. PCR based methods, sequencing based methods, nucleic acid hybridization based methods, gene expression levels, etc. In one aspect for example a KASP assay may be used.

A method for screening (e.g. genotyping) genomic DNA of watermelon, cucumber or melon plants, seeds or plant parts is provided comprising the steps of:

a) providing a sample (or a plurality of samples) of genomic DNA of a watermelon, melon or cucumber plant or of a plurality of plants (e.g. a F2 population, inbred lines, a backcross population, a breeding population, hybrid plants, etc.), b) providing a pair of PCR primers or an oligonucleotide probe, which primers or (oligonucleotide) probe comprise at least 10, 11, 12, 13, 14, 15, 16, 17, 18, 19, 20, 21, 22 or more consecutive nucleotides of the genomic WAP5.1 allele of the watermelon, cucumber or melon WAP5.1 gene and can hybridize to the genomic allele and/or amplify part of the genomic allele in a PCR assay, and c) carrying out a PCR assay using the primer pair or a hybridization assay using the probe of step b) on the sample(s) of step a), and optionally d) selecting a plant or plant part or seed comprising one or two copies of an allele (e.g. a wild type allele and/or a mutant allele) of the watermelon, cucumber or melon WAP5.1 gene in the genome, wherein the wild type allele of the watermelon WAP5.1 gene encodes the protein of SEQ ID NO: 1 or of SEQ ID NO: 9 (or a wild type protein comprising at least 95%, 96%, 97%, 98%, 99% identity to SEQ ID NO: 1 or SEQ ID NO:9), the wild type allele of the cucumber WAP5.1 gene encodes the protein of SEQ ID NO: 2 (or a wild type protein comprising at least 95%, 96%, 97%, 98%, 99% identity to SEQ ID NO: 2) and the wild type allele of the melon WAP5.1 gene encodes the protein of SEQ ID NO: 3 (or a wild type protein comprising at least 95%, 96%, 97%, 98%, 99% identity to SEQ ID NO: 3).

In step b) a PCR primer pair is at least one forward primer, complementary to one of the DNA strands of the WAP5.1 allele and one reverse primer complementary to the other DNA strand of the WAP5.1 allele, which primer pair hybridizes to the denatured genomic DNA and amplifies part of the WAP5.1 allele in a PCR reaction. Primers can be designed to amplify the wild type or any mutant WAP5.1 allele using primer design tools. In one aspect two forward primers are used, one designed to amplify the wild type allele and one designed to amplify a mutant allele of the WAP5.1 gene, and one common reverse primer. These three primers can be used in a KASP-assay to genotype the samples of step a). Thus, in one aspect the assay in step c) is a KASP-assay, but also other genotyping assays can be used, such as those described in world wide web at biosearchtech.com/sectors/agrigenomics/agrigenomics-pcr-qpcr-technologies.

In one aspect the assay discriminates between a wild type and a mutant allele of the WAP5.1 gene, e.g. between the wild type WAP5.1 allele and a mutant allele of Table 1, or another mutant allele.

For analyzing the genomic DNA at least crude genomic DNA extraction may be necessary. The presence of a mutant allele or a wild type allele in the genomic DNA can be detected directly or indirectly. Directly may for example be by nucleic acid hybridization of e.g. oligonucleotide probes. Indirectly may for example be by nucleic acid amplification using e.g. PCR primers which comprise e.g. a tail sequence attached to the primer and during PCR the allele-specific primer binds to the template DNA and elongates, thereby attaching the tail sequence to the newly synthesized strand and in subsequent PCR rounds a FRET cassette (fluorescent resonant energy transfer cassette) binds to the tail and emits fluorescence. The fluorescent signal can then be detected. This is used e.g. in the KASP-assay.

The mutant allele may differ from the wild type allele in various aspects, e.g. in the promoter sequence or in the protein coding sequence or in the intron/exon splice sites. The mutant allele may have a reduced gene expression or no gene expression or it may result in the production of a protein comprising one or more amino acids deleted, replaced, or inserted or duplicated compared to the wild type protein.

In one aspect the mutant allele is an allele encoding a mutant protein as described in Table 1.

In one aspect the plant or plant part is watermelon and the mutant allele encodes the protein of SEQ ID NO: 4 or of SEQ ID NO: 10.

Also methods of generating and/or selecting plants or plant parts comprising at least one mutant allele of the watermelon WAP5.1 gene, or of the cucumber WAP5.1 gene or of the melon WAP5.1 gene in their genome is provided.

In one aspect also a method for detecting the presence of a wild type allele and/or of a mutant allele of the watermelon WAP5.1 gene, or of the cucumber WAP5.1 gene or of the melon WAP5.1 gene in the genome is provided.

In one aspect a method for detecting whether a watermelon plant or plant part or seed comprises at least one copy of the wild type allele, e.g. encoding the protein of SEQ ID NO: 1 or 9, and/or comprises at least one copy of a mutant allele, e.g. encoding the protein of SEQ ID NO: 4 or 10, or a mutant protein as shown in Table 1, is provided and optionally selecting a plant, plant part or seed comprising at least one copy of a mutant wap5.1 allele.

Also a KASP-assay (Kbioscience Kompetitive Allele specific PCR-genotyping Assay) is provided comprising two allele specific forward primers, e.g. a FAM primer and a VIC primer and a Common reverse primer. Obviously, other allele specific primers can be developed to detect and/or discriminate between the wild type allele and any other mutant allele comprising e.g. one or more amino acids replaced, duplicated, deleted or inserted with respect to the wild type protein.

Likewise isolated sequences or molecules of the (wild type or mutant) genomic sequence, the cDNA or mRNA sequence, protein sequences, as well as oligonucleotide primers or probes for detecting a wild type or mutant allele of the watermelon WAP5.1 gene, or of the cucumber WAP5.1 gene or of the melon WAP5.1 gene are encompassed herein.

Also a method for generating a PCR amplification product and/or a oligonucleotide hybridization product of (a part of the) genomic DNA of watermelon, cucumber or melon plants, seeds or plant parts is provided comprising the steps of:

a) providing a sample (or a plurality of samples) of genomic DNA of a watermelon, melon or cucumber plant or of a plurality of plants (e.g. a F2 population, inbred lines, a backcross population, a breeding population, hybrid plants, etc.), b) providing at least a pair of PCR primers or at least one oligonucleotide probe, which primers or (oligonucleotide) probe comprise at least 10, 11, 12, 13, 14, 15, 16, 17, 18, 19, 20, 21, 22 or more consecutive nucleotides of the genomic WAP5.1 allele of the watermelon, cucumber or melon WAP5.1 gene and can hybridize to the genomic allele and/or amplify part of the genomic allele in a PCR assay, and c) carrying out a PCR assay using the primer pair or a hybridization assay using the probe of step b) on the sample(s) of step a) to generate a PCR amplification product and/or an oligonucleotide hybridization product, and optionally d) selecting a plant or plant part or seed comprising one or two copies of an allele (e.g. a wild type allele and/or a mutant allele) of the WAP5.1 gene in the genome, wherein the wild type allele of the watermelon WAP5.1 gene encodes the protein of SEQ ID NO: 1 or of SEQ ID NO: 9 (or a wild type protein comprising at least 95%, 96%, 97%, 98%, 99% identity to SEQ ID NO: 1 or SEQ ID NO:9), the wild type allele of the cucumber WAP5.1 gene encodes the protein of SEQ ID NO: 2 (or a wild type protein comprising at least 95%, %%, 97%, 98%, 99% identity to SEQ ID NO: 2) and the wild type allele of the melon WAP5.1 gene encodes the protein of SEQ ID NO: 3 (or a wild type protein comprising at least 95%, %%, 97%, 98%, 99% identity to SEQ ID NO: 3).

Further a method for amplifying and/or hybridizing (a part of the) genomic DNA of watermelon, cucumber or melon plants, seeds or plant parts is provided comprising the steps of:

a) providing a sample (or a plurality of samples) of genomic DNA of a watermelon, melon or cucumber plant or of a plurality of plants (e.g. a F2 population, inbred lines, a backcross population, a breeding population, hybrid plants, etc.), b) providing at least a pair of PCR primers or at least one oligonucleotide probe, which primers or (oligonucleotide) probe comprise at least 10, 11, 12, 13, 14, 15, 16, 17, 18, 19, 20, 21, 22 or more consecutive nucleotides of the genomic WAP5.1 allele of the watermelon, cucumber or melon WAP5.1 gene and can hybridize to the genomic allele and/or amplify part of the genomic allele in a PCR assay, and c) carrying out a PCR assay using the primer pair or a hybridization assay using the probe of step b) on the sample(s) of step a) to generate a PCR amplification product and/or a oligonucleotide hybridization product, and optionally d) selecting a plant or plant part or seed comprising one or two copies of an allele (e.g. a wild type allele and/or a mutant allele) of the watermelon, cucumber or melon WAP5.1 gene in the genome, wherein the wild type allele of the watermelon WAP5.1 gene encodes the protein of SEQ ID NO: 1 or of SEQ ID NO: 9 (or a wild type protein comprising at least 95%, 96%, 97%, 98%, 99% identity to SEQ ID NO: 1 or SEQ ID NO:9), the wild type allele of the cucumber WAP5.1 gene encodes the protein of SEQ ID NO: 2 (or a wild type protein comprising at least 95%, %%, 97%, 98%, 99% identity to SEQ ID NO: 2) and the wild type allele of the melon WAP5.1 gene encodes the protein of SEQ ID NO: 3 (or a wild type protein comprising at least 95%, %%, 97%, 98%, 99% identity to SEQ ID NO: 3).

Also a genotyping kit comprising primers and/or probes and reaction components to amplify and/or hybridize part of the genomic DNA of the WAP5.1 gene is provided.

Primers and probes are preferably labelled or modified by e.g. a tail sequence or label, to be able to detect the amplification or hybridization reaction products.

General Definition

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells plants, etc. Similarly, "a fruit" or "a plant" also refers to a plurality of fruits and plants.

As used herein, the term "plant" includes the whole plant or any parts or derivatives thereof, preferably having the same genetic makeup as the plant from which it is obtained, such as plant organs (e.g. harvested or non-harvested fruits, leaves, flowers, anthers, etc.), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants, such as plant cuttings, embryos, pollen, anthers, ovules, fruits (e.g. harvested tissues or organs), flowers, leaves, seeds, clonally propagated plants, roots, stems, root tips, grafts (scions and/or root stocks) and the like. Also any developmental stage is included, such as seedlings, cuttings prior or after rooting, etc. When "seeds of a plant" are referred to, these either refer to seeds from which the plant can be grown or to seeds produced on the plant, after self-fertilization or cross-fertilization.

As used herein, the term "variety" or "cultivar" means a plant grouping within a single botanical taxon of the lowest known rank, which can be defined by the expression of the characteristics resulting from a given genotype or combination of genotypes.

The term "allele(s)" means any of one or more alternative forms of a gene at a particular locus, e.g. the WAP5.1 locus (where the WAP5.1 gene is located; the alleles of the gene may be wild type alleles designated WAP5.1, or mutant alleles designated wap5.1), all of which alleles relate to one trait or characteristic at a specific locus (e.g. facultative parthenocarpy). In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous), e.g. two identical copies of the mutant wap5.1 allele (i.e. wap5.1/wap5.1) or one copy of the mutant wap5.1 allele and one copy of the wild type allele (i.e. wap5.1/WAP5.1). Likewise a triploid plant is referred to as homozygous for the gene if it has three identical alleles of a gene (e.g. three copies of the mutant wap5.1 allele, i.e. wap5.1/wap5.1wap5.1) and a tetraploid plant is referred to as homozygous for the gene if it has four identical alleles of the gene, e.g. four copies of the mutant wap5.1 allele (i.e. wap5.1/wap5.1/wap5.1/wap5.1).

"WAP5.1 gene" is a single, recessive gene identified in cultivated watermelon on chromosome 5, which when mutated results in parthenocarpy, especially facultative parthenocarpy. WAP5.1 is the wild type (WT), functional allele as present in non-parthenocarpic cultivated watermelon plants and wap5.1 is the mutant allele resulting in parthenocarpy if the allele is in homozygous form in a diploid (wap5.1/wap5.1), triploid (wap5.1/wap5.1/wap5.1), tetraploid (wap5.1/wap5.1/wap5.1/wap5.1), or other polyploidy, e.g. octaploid, etc. In one aspect the WAP5.1 gene is the gene encoding a protein of SEQ ID NO: 1 or SEQ ID NO: 9, or encoding a protein comprising at least 94%, 95%, 96%, 97%, 98%, 99%, 99.5%, 99.8% or 99.9% sequence identity to SEQ ID NO: 1 or to SEQ ID NO: 9 (watermelon), when aligned pairwise. This includes in one aspect orthologs of WAP5.1 in cucumber (SEQ ID NO: 2) and melon (SEQ ID NO: 3).

"Parthenocarpy" or "parthenocarpic" is generally understood in the art and also to be understood in connection with the present invention to describe the development of fruits without fertilization of the female ovule. A pollination process is not needed for producing fruits which fruits however as a consequence of the lack of pollination are seedless. Thus, parthenocarpy means herein that fruits are formed on the plant without pollination of the female flowers. Likewise a "parthenocarpic plant" or a "plant comprising a mutant gene (or mutant allele of a gene) conferring parthenocarpy when in homozygous form" means that the plant produces seedless fruits without pollination of the female flowers.

"Facultative parthenocarpy" is understood to mean that the parthenocarpy trait is not seen when the flower of the facultative parthenocarpic plant is pollinated, in which case normal fertilization and normal fruit development takes place. As normal fertilization takes place, the fruits are seeded.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

The term "gene" means a (genomic) DNA sequence comprising a region (transcribed region), which is transcribed into a messenger RNA molecule (mRNA) in a cell, and an operably linked regulatory region (e.g. a promoter). An example is the WAP5.1 gene of the invention. Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Mutant wap5.1 allele" or "wap5.1 allele" refers herein to a mutant allele of the WAP5.1 gene on chromosome 5 in watermelon, which causes the plant to be facultative parthenocarpic when the mutant allele is in homozygous form. The mutation in the mutant allele can be any mutation or combination of mutations, including deletions, truncations, insertions, point mutations, non-sense mutations, mis-sense mutations or non-synonymous mutations, splice-site mutations, frame shift mutations and/or mutations in one or more regulatory sequences such as promoter sequence, or enhancer or silencer sequences. In one aspect the mutant wap5.1 allele is a mutant allele of the WAP5.1 gene whereby the WAP5.1 gene is the gene encoding a protein of SEQ ID NO: 1 or SEQ ID NO: 9, or encoding a protein comprising at least 94%, 95%, 96%, 97%, 98%, 99%, 99.5%, 99.8% or 99.9% sequence identity to SEQ ID NO: 1 or to SEQ ID NO: 9 (when aligned pairwise). This includes in one aspect mutant alleles of orthologs of the WAP5.1 gene in cucumber (SEQ ID NO: 2) and melon (SEQ ID NO: 3) present in cucumber or melon plants or plant cells.

"Wild type WAP5.1 allele" or "WAP5.1 allele" refers herein to the functional allele of the WAP5.1 gene, which causes the plant to have a normal fruit set, requiring normal pollination and fertilization to set fruits. The wild type WAP5.1 allele is found in any commercial variety of watermelon (e.g. Nunhems variety Premium F1, Montreal F1, and others). In one aspect the wild type WAP5.1 allele is a wild type allele of the WAP5.1 gene whereby the WAP5.1 gene is the gene encoding a protein of SEQ ID NO: 1 or of SEQ ID NO: 9 or encoding a protein comprising at least 94%, 95%, 96%, 97%, 98%, 99%, 99.5%, 99.8% or 99.9% sequence identity to SEQ ID NO: 1 or to SEQ ID NO: 9 (when aligned pairwise). This includes in one aspect orthologs of the WAP5.1 gene in cucumber (SEQ ID NO: 2) and melon (SEQ ID NO: 3) present in cucumber or melon plants or plant cells.

The term "locus" (loci plural) means a specific place or places or a site on a chromosome where for example a gene or genetic marker is found. The WAP5.1 locus is, thus, the location in the genome of watermelon, where the mutant allele and/or the wild type allele of the WAP5.1 gene is found. The WAP5.1 locus is a locus on cultivated watermelon chromosome 5 (using the chromosome assignment of the published watermelon genome found at world wide web at cucurbitgenomics.org under "Watermelon: Genome", "Charleston Grey" or "watermelon 97103", i.e. wap5.1 was generated in the cultivated watermelon genome by mutagenesis and the mutant wap5.1 allele was mapped to a defined region of chromosome 5 of cultivated watermelon.

"Induced mutant" alleles are mutant alleles in which the mutation(s) is/are/have been induced by human intervention, e.g. by mutagenesis via physical or chemical mutagenesis methods or via e.g. tissue culture (as described in e.g. Zhang et al, Plos 9(5) e96879), including also targeted gene editing techniques (such as Crispr based techniques, TALENS, etc.).

"Diploid plant" refers to a plant, vegetative plant part(s), or seed from which a diploid plant can be grown, having two sets of chromosome, designated herein as 2n.

A "DH plant" or "doubled-haploid plant" is a diploid plant produced by doubling the haploid genome of the diploid plant using e.g. in vitro techniques. A DH plant is, therefore, homozygous at all loci.

"Triploid plant" refers to a plant, vegetative plant part(s), or seed from which a triploid plant can be grown, having three sets of chromosomes, designated herein as 3n.

"Tetraploid plant" refers to a plant, vegetative plant part(s), or seed from which a tetraploid plant can be grown, having four sets of chromosomes, designated herein as 4n.

"Polyploid plant" refers to plants having a higher ploidy than diploid, i.e. triploid (3n), tetraploid (4n), hexaploid (6n), octaploid (8n), etc.

"Pollenizer plant" or "pollenizer" refers to the (inbred or hybrid) diploid plant, or parts thereof (e.g. its pollen or scion), suitable as pollenizer for inducing fruit set on triploid plants. A pollenizer plant is, thus, able to lead to good fruit set (and good triploid fruit yield) of normal triploid plants (comprising three copies of the wild type WAP5.1 allele), by producing an appropriate amount of pollen at the appropriate day-time and for an appropriate period of time.

"Hybrid triploid plant" or "F1 triploid" or "triploid hybrid" is a triploid plant grown from hybrid, triploid seed obtained from cross fertilizing a male diploid parent with a female tetraploid parent. The male parent is used for inducing fruit set and seed production on a tetraploid female parent, resulting in fruits containing F1 hybrid triploid seeds. Both the male parent and the female parent used to produce F1 triploid seeds are inbred so that each parent line is nearly homozygous and stable.

Figure 5:
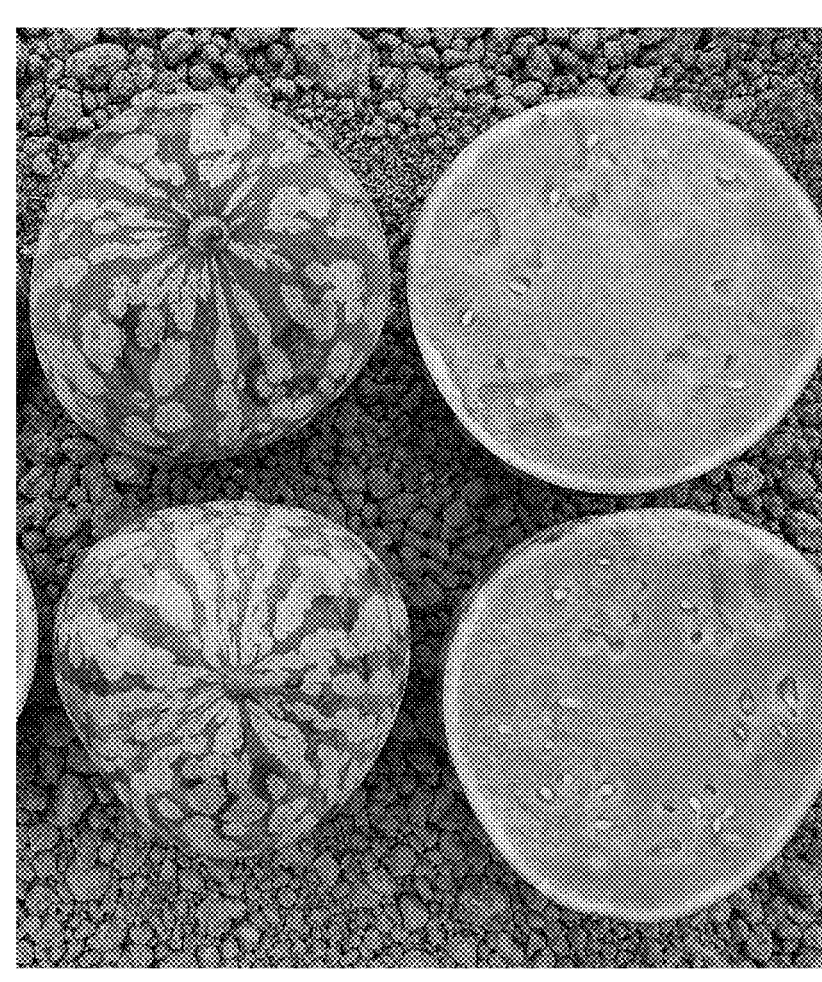

"Seedless fruit" are fruits which contain no viable mature seeds. The fruit may contain one or more small, edible, white ovules, e.g. as seen in FIG. 1 or FIG. 5. Optionally the fruit may contain a few brown or black seeds, but these are not viable. Viable mature seeds are seeds which can be germinated in soil under appropriate conditions and grow into plants.

"Planting" or "planted" refers to seeding (direct sowing) or transplanting seedlings (plantlets) into a field by machine or hand.

"Vegetative propagation" or "clonal propagation" refers to propagation of plants from vegetative tissue, e.g. by in vitro propagation or grafting methods (using scions and rootstocks). In vitro propagation involves in vitro cell or tissue culture and regeneration of a whole plant from the in vitro culture. Grafting involves propagation of an original plant by grafting onto a rootstock. Clones (i.e. genetically identical vegetative propagations) of the original plant can thus be generated by either in vitro culture or grafting.

"Cell culture" or "tissue culture" refers to the in vitro culture of cells or tissues of a plant. "Regeneration" refers to the development of a plant from cell culture or tissue culture or vegetative propagation. "Non-propagating cell" refers to a cell which cannot be regenerated into a whole plant.

"Recessive" refers to an allele which expresses its phenotype (e.g. parthenocarpy or facultative parthenocarpy) when no dominant allele is present in the diploid genome, i.e. when it is homozygous in a diploid. The mutant wap5.1 allele results in a (facultative) parthenocarp plant when present in two copies in a diploid plant, optionally in four copies in a tetraploid plant or in two or three copies in a triploid plant or in the respective number of copies in another polyploidy. The dominant allele is herein also referred to as the wild type (WT) allele.

"Cultivated watermelon" or "*Citrullus lanatus*" refers herein to *Citrullus lanatus* ssp. *vulgaris*, or *Citrullus lanatus* (Thunb.) Matsum. & Nakai subsp. *vulgaris* (Schrad.), and having good agronomic characteristics, especially producing marketable fruits of good fruit quality and fruit uniformity. Cultivated cucumber and cultivated melon refer to *Cucumis sativus* and *Cucumis melo* plants having good agronomic characteristics, especially producing marketable fruits of good fruit quality and fruit uniformity.

"Wild watermelon" refers herein to *Citrullus lanatus* ssp. *lanatus* and *Citrullus lanatus* ssp. *mucosospermus*, producing fruits of poor quality and poor uniformity.

"SNP marker" refers to a Single Nucleotide Polymorphism between e.g. a mutant wap5.1 allele and a wild type WAP5.1 allele. For example SEQ ID NO: 8 provides a sequence comprising a SNP at nucleotide 61, whereby the presence of a 'C' (Cytosine) indicates the presence of the wild type WAP5.1 allele and the presence of a 'T' (Thymine) indicates the presence of the mutant allele, which encodes the protein of SEQ ID NO: 4 (L528F mutation). Using a SNP marker assay which can distinguish between the mutant and wild type allele of the WAP5.1 gene (i.e. an allele specific assay) one can screen pants, plant parts or the DNA therefrom for the presence of the mutant allele and/or the wild type allele.

"INDEL marker" refers to an insertion/deletion polymorphism between e.g. a mutant wap5.1 allele and a wild type WAP5.1 allele. Using an INDEL marker assay which can distinguish between the mutant and wild type allele of the gene (i.e. an allele specific assay) one can screen pants, plant parts or the DNA therefrom for the presence of the mutant allele.

"Genotyping" methods are methods whereby the genotype or allelic composition of a plant or plant part or seed can be determined. Bi-allelic genotyping assays, such as KASP-assays, can distinguish between two alleles at a locus.

"Cultivated watermelon genome" and "physical position on the cultivated watermelon genome" and "chromosome 5" refers to the physical genome of cultivated watermelon, the reference genome is found on the world wide web at cucurbitgenomics.org under "Watermelon: Genome", e.g. "Watermelon (Charleston Grey)" and the physical chromosomes and the physical position on the chromosomes.

A "chromosome region comprising the mutant wap5.1 allele" refers to the genomic region of e.g. chromosome 5 of cultivated watermelon which region carries the mutant wap5.1 allele. The presence of the allele can be determined phenotypically and/or by the presence of one or more molecular markers, e.g. SNP markers or other markers, linked to the mutant wap5.1 allele or preferably markers distinguishing different wap5.1 alleles or by the genomic sequence of the allele sequence itself (e.g. sequencing the allele). A marker is "linked to the wap5.1 allele", if it is physically coupled to the allele. An "allele specific marker" is a marker which is specific for a particular allele (e.g. a specific mutant allele) and is thus discriminating between e.g. the mutant allele and the wild type allele.

A pair of "flanking markers" refers to two markers, preferably two SNP markers or two sequences comprising the SNP markers, which are linked to the wap5.1 allele, and/or which are closely linked to the wap5.1 allele, whereby the wap5.1 allele is located in-between the two markers or in-between the two sequences comprising the markers.

"Brix" or "degree Brix" or "° brix" refers to the mean total soluble solids content as measured on several mature fruits using a refractometer. Preferably the mean of at least three fruits, each measured between the centre and the rind of the cut-open fruit, is calculated.

"Marketable" in relation to fruit quality means that the watermelon fruits are suitable for being sold for fresh consumption, having good flavour (no off-flavours), a degree brix of at least 9.0, preferably at least 10.0 or at least 11.0 and preferably also a uniform fruit flesh color, being e.g. white (e.g. variety Cream of Saskatchewan), yellow (e.g. variety Yamato Cream 1), orange (e.g. variety Tendersweet), pink (e.g. variety Sadul), pinkish red (e.g. variety Crimson Sweet), red (e.g. variety Sugar Baby) or dark red (e.g. variety Dixie Lee).

"Uniform fruit flesh color" means that the color throughout the mature fruits, when cut open through the middle (midsection), is evenly distributed throughout the fruit flesh, i.e. not patchy. Thus, a red fruit is red throughout the fruit flesh and does not contain white patches. An example of a fruit with uniform red color is the diploid variety Premium F1 (Nunhems).

"Physical distance" between loci (e.g. between molecular markers and/or between phenotypic markers) on the same chromosome is the actually distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of about 1%. If no recombinants can be found, the RF is zero and the loci are either extremely close together physically or they are identical. The further apart two loci are, the higher the RF.

"Uniformity" or "uniform" relates to the genetic and phenotypic characteristics of a plant line or variety. Inbred lines are genetically highly uniform as they are produced by several generations of inbreeding. Likewise, and the F1 hybrids and the triploid hybrids which are produced from such inbred lines are highly uniform in their genotypic and phenotypic characteristics and performance.

A genetic element, an introgression fragment, or a gene or allele conferring a trait (such as parthenocarpy) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as a non-parthenocarp line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Cultivated watermelons containing the genetic element, locus, introgression fragment, gene or allele (e.g. a mutant wap5.1 allele) can be generated de novo, e.g. by mutagenesis (e.g. chemical mutagenesis, CRISPR-Cas induced, etc.) and then e.g. be crossed into other cultivated watermelons. The same applies for cucumber and melon, i.e. mutant wap5.1 alleles can be generated de novo by mutagenesis.

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 10, 15, 20, 30, 40, 50 or more plants (or plant parts) are measured, preferably in randomized experimental designs with several replicates and suitable control plants grown under the same conditions in the same experiment. "Statistically significant" or "statistically significantly" different or "significantly" different refers to a characteristic of a plant line or variety that, when compared to a suitable control show a statistically significant difference in that characteristic (e.g. the p-value is less than 0.05, $p<0.05$, using ANOVA) from the (mean of the) control.

The term "traditional breeding techniques" encompasses herein crossing, backcrossing, selfing, selection, double haploid production, chromosome doubling, embryo rescue, protoplast fusion, marker assisted selection, mutation breeding etc., all as known to the breeder (i.e. methods other than genetic modification/transformation/transgenic methods), by which, for example, a chromosome 5 comprising a mutant wap5.1 allele can be obtained, identified and/or transferred.

"Backcrossing" refers to a breeding method by which a (single) trait, such as the facultative parthenocarpy trait, can be transferred from one (often an inferior) genetic background (also referred to as "donor") into another (often a superior) genetic background (also referred to as "recurrent parent". An offspring of a cross (e.g. an F1 plant obtained by crossing e.g. the donor with the recurrent parent watermelon, or an F2 plant or F3 plant, etc., obtained from selfing the F1), is "backcrossed" to the parent with e.g. the superior genetic background. After repeated backcrossing, the trait of the one (often inferior) genetic background will have been incorporated into the other (often superior) genetic background.

A molecular marker (or a sequence comprising a molecular marker) within 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less of another marker (or a sequence comprising the molecular marker), or of a locus, refers to a marker which is physically located within the 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less, of the genomic DNA region flanking the marker (i.e. either side of the marker).

"LOD-score" (logarithm (base 10) of odds) refers to a statistical test often used for linkage analysis in animal and plant populations. The LOD score compares the likelihood of obtaining the test data if the two loci (molecular marker loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome. When referring to a "sequence"

herein, it is understood that the molecule having such a sequence is referred to, e.g. the nucleic acid molecule.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimising the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff& Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 92%, 95%, 98%, 99% or more (as determined by Emboss "needle" using default parameters, i.e. gap creation penalty=10, gap extension penalty=0.5, using scoring matrix DNAFULL for nucleic acids and Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 91%, 92%, 93%, 94%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically, stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions.

"M1 generation" or "M1 plants" in context with the present invention shall refer to the first generation that is produced directly from the mutagenic treatment. A plant grown from seeds treated with a mutagen e.g. is a representative of an M1 generation.

"M2 generation" or "M2 plant" shall refer herein to the generation obtained from self-pollination of the M1 generation. A plant grown from seeds obtained from a self-pollinated M1 plant represents a M2 plant. M3, M4, etc. refers to further generations obtained after self-pollination.

"Allelism test" refers to a genetic test whereby it can be tested whether a phenotype, e.g. facultative parthenocarpy, seen in two plant lines or varieties are determined by the same gene or locus or by different genes or loci. For example, the plants to be tested are crossed with each other (preferably after selfing to ensure they are homozygous), the segregation of the phenotypes amongst the F1 or further selfing or backcross progeny is determined. The ratio of segregation indicates if the genes or loci are allelic or if they are different. So for example if the alleles are of the same gene, F1 plants (produced by crossing two homozygous plants) will all (100%) have the same phenotype, while that may not be the case if the alleles are of different genes. Likewise in F2 plants phenotypic segregation will indicate whether the same or different genes are involved.

An "mRNA coding sequence" shall have the common meaning herein. An mRNA coding sequence corresponds to the respective DNA coding (cDNA) sequence of a gene/allele apart from that thymine (T) is replaced by uracil (U).

A "mutation" in a nucleic acid molecule (DNA or RNA) is a change of one or more nucleotides compared to the corresponding wild type sequence, e.g. by replacement, deletion or insertion of one or more nucleotides. Examples of such a mutation are point mutation, nonsense mutation, missense mutation, splice-site mutation, frame shift mutation or a mutation in a regulatory sequence.

A "nucleic acid molecule" shall have the common understanding in the art. It is composed of nucleotides comprising either of the sugars deoxyribose (DNA) or ribose (RNA).

A "point mutation" is the replacement of a single nucleotide, or the insertion or deletion of a single nucleotide.

A "nonsense mutation" is a (point) mutation in a nucleic acid sequence encoding a protein, whereby a codon in a nucleic acid molecule is changed into a stop codon. This results in a pre-mature stop codon being present in the mRNA and results in translation of a truncated protein. A truncated protein may have decreased function or loss of function.

A "missense or non-synonymous mutation" is a (point) mutation in a nucleic acid sequence encoding a protein, whereby a codon is changed to code for a different amino acid. The resulting protein may have decreased function or loss of function.

A "splice-site mutation" is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have decreased function or loss of function.

A "frame shift mutation" is a mutation in a nucleic acid sequence encoding a protein by which the reading frame of the mRNA is changed, resulting in a different amino acid sequence. The resulting protein may have decreased function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid at either the N-terminus or the C-terminus of the protein is missing compared to the amino acid sequence of the corresponding wild type protein, whereby in a 3'-end or C-terminal truncation at least the first nucleotide at the 5'-end or the first amino acid at the N-terminus, respectively, is still present and in a 5'-end or N-terminal truncation at least the last nucleotide at the 3'-end or the last amino acid at the C-terminus, respectively, is still present. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence.

A "mutation in a regulatory sequence", e.g. in a promoter or enhancer of a gene, is a change of one or more nucleotides compared to the wild type sequence, e.g. by replacement, deletion or insertion of one or more nucleotides, leading for example to decreased or no mRNA transcript of the gene being made.

A "mutation in a protein" is a change of one or more amino acid residues compared to the wild type sequence, e.g. by replacement, deletion, truncation or insertion of one or more amino acid residues.

"Mutant protein" is herein a protein comprising one or more mutations in the nucleic acid sequence encoding the protein, whereby the mutation results in (the mutant nucleic acid molecule encoding) a "reduced-function" or "loss-of-function" protein, as e.g. measurable in vivo, e.g. by the phenotype conferred by the mutant allele.

"Wild type 3-dimensional structure" or "wild type protein folding" refers to the in vivo folding of the wild type protein to carry out its normal function in vivo. "Modified 3-dimensional structure or modified protein folding" refers to the mutant protein having a different folding than the wild type protein, which reduces or abolishes its normal function or activity in vivo, i.e. the protein has a reduced-function or loss-of-function.

In context of the present invention, "decreased activity" of a protein shall mean a decrease in activity of a WAP5.1 protein when compared to a corresponding wild type plant cell or a corresponding wild type plant. Decrease shall in one aspect comprise an entire knock-out or knock-down of gene expression, or the production of a loss-of-function or of a reduced-function WAP5.1 protein, e.g. a mutant WAP5.1 protein may have lost function or decreased function compared to the wild type, functional WAP5.1 protein. A decrease in activity can be a decrease in the expression of a gene encoding a WAP5.1 protein (also referred to as knock-down), or a knock-out of the expression of a gene encoding a WAP5.1 protein and/or a decrease in the quantity of a WAP5.1 protein in the cells, or a reduced-function or loss-of-function in the activity of a WAP5.1 protein in the cells.

In context with the present invention, the term "wild type plant cell" or "wild type plant" means that they comprise wild type wap5.1 alleles and not mutant wap5.1 alleles. Thus, the wild type plant or wild type plant cell is a plant or plant cell comprising fully functional WAP5.1 genes, encoding a fully functional WAP5.1 proteins (also referred to as wild type WAP5.1 protein), e.g. regarding watermelon plants or plant cells a diploid watermelon plant producing the protein of SEQ ID NO: 1 or of SEQ ID NO: 9 (or a protein comprising at least 95%, 96%, 97%, 98%, 99% sequence identity to SEQ ID NO: 1 or to SEQ ID NO: 9) and producing fruits only after pollination. Or regarding melon plants or cells a diploid melon plant producing the protein of SEQ ID NO: 3 (or a protein comprising at least 95% 96%, 97%, 98%, 99% sequence identity to SEQ ID NO: 3) or regarding cucumber plants or cells a diploid cucumber plant producing the protein of SEQ ID NO: 2 (or a protein comprising at least 95% 96%, 97%, 98%, 99% sequence identity to SEQ ID NO: 2).

"Knock-out" or "entire knock-out" shall be understood that expression of the respective gene is not detectable anymore.

"Loss-of-function" or "reduced-function" or "decreased function" shall mean in context of the present invention that the protein, although possibly present in amounts equal or similar to a corresponding wild type protein, does not evoke its normal effect anymore, i.e. for mutant alleles encoding such a protein when present in homozygous form in a diploid plant, the plant produces seedless fruits in the absence of pollination and seeded fruits in the presence of pollination.

"Conserved domain" refer to conserved protein domains, such as the "LRR-domain" and the "F-box domain", both of which are likely involved in protein-protein interactions. In the watermelon WAP5.1 protein of SEQ ID NO: 1 or SEQ ID NO: 9 an F-box domain is found from amino acid 237 to 277, in the cucumber WAP5.1 protein of SEQ ID NO: 2 it is found from amino acid 244 to 284 and in the melon protein of SEQ ID NO: 3 it is found from amino acid 247 to 287. In the watermelon WAP5.1 protein of SEQ ID NO: 1 or of SEQ ID NO: 9 an LRR-domain domain is found from amino acid 291 to 1033, in the cucumber WAP5.1 protein of SEQ ID NO: 2 it is found from amino acid 297 to 1040 and in the melon protein of SEQ ID NO: 3 it is found from amino acid 301 to 1043. Conserved domains can e.g. be found in the Conserved Domain Database of the NCBI (world wide web at ncbi.nlm.nih.gov/cdd).

"Marker assisted selection" or "MAS" is a process of using the presence of molecular markers (such as SNP markers or INDEL markers), which are genetically and physically linked to a particular locus or to a particular chromosome region or allele specific markers, to select plants for the presence of the specific locus or region or allele. For example, a molecular marker genetically and physically linked to the mutant wap5.1 allele or an allele specific marker, can be used to detect and/or select e.g. watermelon plants, or plant parts, comprising the mutant wap5.1 allele. Allele specific markers are preferred markers, as they select for the allele directly.

"Targeted gene editing" is referred to techniques whereby endogenous target genes can be modified, e.g. one or more nucleotides can be inserted, replaced and/or deleted e.g. in the promoter or coding sequence. For example CRISPR based techniques, such as Crispr-Cas9 gene editing, Crispr-Cpf1 gene editing, or more recent techniques called 'base editing' or 'primer editing' can be used to modify endogenous target genes, such as the endogenous wild type WAP5.1 gene in watermelon (encoding the protein of SEQ ID NO: 1 or 9, or a wild type protein comprising at least 95% sequence identity to SEQ ID NO: 1 or 9). The mutants described herein can, for example, be reproduced by targeted gene editing of the wild type WAP5.1 gene.

"Oligonucleotides" or "oligos" or "oligonucleotide primers or probes" are short, single-stranded polymers of nucleic acid, e.g. at least 10, 11, 12, 13, 14, 15, 16, 17, 18, 19, 20, 21, 22, 23, 24 or more nucleotides in length. Oligos may be unmodified or modified with a variety of chemistries depending on their intended use, for example, the addition of 5' or 3' phosphate groups to enable ligation or block extension, respectively, labelling with radionuclides or fluorophores and/or quenchers for use as probes, the incorporation of thiol, amino, or other reactive moieties to enable the covalent coupling of functional molecules such as enzymes, and extension with other linkers and spacers of diverse functionality. DNA oligos are the most commonly used, but RNA oligos are also available. The length of an oligo is usually designated by adding the suffix-mer. For example, an oligonucleotide with 19 nucleotides (bases) is called a 19-mer. For most uses, oligonucleotides are designed to base-pair with a strand of DNA or RNA. The most common use for oligonucleotides is as primers for PCR (polymerase chain reaction). Primers are designed with at least part of their sequence complementary to the sequence targeted for amplification. Optimal primer length for a complementary sequence is e.g. 18 to 22 nucleotides. Optimal primer sequences for PCR are usually determined by primer design software.

"DNA microarrays" are arrays which have many microscopic spots of DNA, usually oligonucleotides, bound on a solid support. Assay targets can be DNA, cDNA, or cRNA. Depending on the system, the hybridization of targets to specific spots is detected by fluorescence, chemiluminescence, or colloidal silver or gold. Microarrays are used for multiple applications such as simultaneous measurement of the expression of large numbers of genes, enabling genome-wide gene expression analysis, as well as genotyping studies using e.g. single-nucleotide polymorphism (SNP) or InDel analysis.

"Complementary strands" refer to two strands of complementary sequence, and may be referred to as sense (or plus) and anti-sense (or minus) strands for double stranded DNA. The sense/plus strand is, generally, the transcribed sequence of DNA (or the mRNA that was generated in transcription), while the anti-sense/minus strand is the strand that is complementary to the sense sequence. For any of the sequences provided herein only one strand of the sequence is given, but the complementary strand of the given strand is also encompassed herein. The complementary nucleotides of DNA are A complementary to T, and G complementary to C. The complementary nucleotides of RNA are A complementary to U, and G complementary to C.

FIG. 1: A foto of a cross section of a watermelon fruit developed in the absence of pollination on a plant homozygous for a mutant wap5.1 allele encoding a protein wherein the amino acid Leucine at position 528 is replaced by the amino acid Phenylalanine (L528F).

FIG. 2: A protein sequence alignment of the watermelon wild type (labelled as 'wt') WAP5.1 protein comprising amino acid Leucine (L) at amino acid 528 and a mutant WAP5.1 protein (labelled as 'wap5.1') comprising Phenylalanine (F) at amino acid 528. Also the F-box is indicated by a solid-line box and the LRR-domain is indicated by a dashed-line box.

FIG. 3A: 3-dimensional structure of the wild type WAP5.1 protein of SEQ ID NO: 1, generated by RaptorX Contact Prediction. Amino acid Leucine 528 is indicated with an arrow, The LRR-domain is folded in a long tail-like structure.

FIG. 3B: 3-dimensional structure of the mutant WAP5.1 protein of SEQ ID NO: 4, comprising a Phenylalanine at position 528 (instead of a Leucine), generated by RaptorX Contact Prediction. As can be seen by the loops sticking out, the 3-dimensional tail structure seen in the wild type protein of FIG. 3A is disrupted and the protein is not folded properly. This disruption extends past amino acid Q581, which sticks out in a loop.

FIG. 4: Multiple sequence alignment of the wild type WAP5.1 proteins of watermelon (labelled as 'wap5.1', SEQ ID NO: 1), melon (SEQ ID NO: 3) and cucumber (SEQ ID NO: 2). The watermelon protein depicted is the protein of SEQ ID NO: 1. The wild type WAP5.1 watermelon protein of SEQ ID NO: 9 is not depicted, but is identical to that of SEQ ID NO: 1, except that amino acid 51 is different. The wild type WAP5.1 proteins of SEQ ID NO: 1 and SEQ ID NO: 9 have 99.9% sequence identity. The star underneath each amino acid indicates identical amino acids. The F-box domain, surrounded by a solid-line box, is 100% identical between the watermelon, cucumber and melon WAP5.1 proteins. The LRR-domain, surrounded by a dashed box, also has a high amino acid identity between the watermelon, cucumber and melon WAP5.1 proteins. The N-terminal region preceding the F-box is the least conserved between the three species. Amino acids highlighted in bold indicate amino acid positions at which mutant alleles have been generated in watermelon (either single amino acid substitutions or STOP codon mutants) and which can be generated in melon and cucumber.

FIG. 5: A foto of cut watermelon fruits developed in the absence of pollination on a plant homozygous for a mutant wap5.1 allele encoding a protein wherein the amino acid Leucine at position 528 is replaced by the amino acid Phenylalanine (L528F).

DETAILED DESCRIPTION

A first embodiment of the present invention concerns cultivated watermelon plants, *Citrullus lanatus*, comprising at least one copy of a mutant allele of a gene conferring parthenocarpy when the mutant allele is in homozygous form, especially facultative parthenocarpy. Thus, in one aspect cultivated watermelon plants are provided, comprising at least one copy of a mutant allele of a single recessive gene called WAP5.1.

The WAP5.1 gene is an endogenous gene of cultivated watermelon, which when mutated and in homozygous form results in parthenocarpy, especially facultative parthenocarpy.

A segregating population made by crossing the mutant parthenocarp watermelon plant identified by the inventors with an elite watermelon line enabled mapping of the WAP5.1 gene to a region on chromosome 5. Further analysis in two mapping populations led to the identification of a gene comprising a mutation which led to a single amino acid substitution (L528F) in the encoded protein. The mutation was unique to the line and was not found in 93 whole genome resequenced lines. The gene was named WAP5.1 (for Watermelon Parthenocarpy gene on chromosome 5). To screen plants for the mutant allele an allele specific marker was designed, provided in SEQ ID NO: 8.

In the mutant parthenocarpic watermelon plant the Leucine at position 528 of the wild type WAP5.1 protein (of SEQ ID NO: 1 or of SEQ ID NO: 9) was replaced by a Phenylalanine (L528F) in the mutant protein (shown in SEQ ID NO: 4 or in SEQ ID NO: 10), as shown in FIG. 2. In the cDNA of the mutant allele (SEQ ID NO: 5 or SEQ ID NO: 12) nucleotide 1582 is a Thymine (T), while it is a Cytosine (C) in the wild type wap5.1 cDNA (SEQ ID NO:6 or SEQ ID NO: 11). This single nucleotide change (or SNP, from C→T) results in the codon changing from codon CTT (encoding Leucine, L) into TTT (encoding Phenylalanine, F). In the genomic DNA of SEQ ID NO: 7 (encoding the wild type WAP5.1 allele of the Charleston Grey genome) the mutation corresponds to the C at nucleotide 4123 being changed into a T at nucleotide 4123, changing codon CTT to TTT. In the genomic DNA of SEQ ID NO: 14 (encoding the wild type WAP5.1 allele of the watermelon 97103 genome) the mutation corresponds to the C at nucleotide 4118 being changed into a T at nucleotide 4118, changing codon CTT to TT.

It was found that this single amino acid change in the mutant WAP5.1 protein changed the normal protein folding of the LRR-domain, leading to the protein being non-functional or having reduced function in vivo. As a result the plant homozygous for this mutant protein (and thus lacking the functional wild type protein) develops seedless fruits in the absence of pollination, and normal seeded fruits when pollination takes place.

Other mutants in the WAP5.1 allele were generated and also the orthologs of cucumber and melon were identified. The findings, therefore, enable not only the production of facultative parthenocarpic watermelon plants, but also of facultative parthenocarpic cucumber or melon plants.

In one aspect a watermelon, cucumber or melon plant or plant part is provided comprising at least one copy of a mutant allele of a gene named WAP5.1, wherein said mutant allele either a) comprises one or more mutations in a regulatory element, resulting in no expression or reduced expression of the allele compared to the wild type allele, and/or b) encodes a mutant protein comprising one or more amino acids replaced, inserted or deleted compared to the wild type protein, wherein said mutant allele of a) or b) confers facultative parthenocarpy when the mutant allele is in homozygous form, and wherein the wild type watermelon allele encodes a protein of SEQ ID NO: 1 or SEQ ID NO: 9, or a protein comprising at least 95%, 96%, 97%, 98%, 99%, 99.5%, 99.8% or 99.9% sequence identity to SEQ ID NO: 1 or SEQ ID NO: 9, the wild type cucumber allele encodes a protein of SEQ ID NO: 2 or a protein comprising at least 95%, 96%, 97%, 98%, 99%, 99.5%, 99.8% or 99.9% sequence identity to SEQ ID NO: 2, and the wild type melon allele encodes a protein of SEQ ID NO: 3 or a protein comprising at least 95%, 96%, 97%, 98%, 99%, 99.5%, 99.8% or 99.9% sequence identity to SEQ ID NO: 3.

The wild type functional WAP5.1 proteins of watermelon, cucumber and melon are provided in SEQ ID NO: 1 and SEQ ID NO: 9 (watermelon), SEQ ID NO: 2 (cucumber) and SEQ ID NO: 3 (melon). They are also depicted in the multiple sequence alignment of FIG. 4. There may however be some amino acid sequence variation in each species and functional WAP5.1 proteins may comprise e.g. 1, 2, 3, 4 or 5 amino acids which are different than in SEQ ID NO: 1, 2 and 3 provided herein or whereby the protein comprises comprising at least 95%, 96%, 97%, 98%, 99% or 99.5% or 99.6%, 99.7%, 99.8% or 99.9% sequence identity to the proteins of SEQ ID NO: 1, 2 or 3. For example a difference was found between the wild type protein in watermelon Charleston Grey variety and in elite line TY. In elite watermelon line TY, the wild type WAP5.1 protein (SEQ ID NO: 9) was found to differ in amino acid 51 from the wild type Charleston Grey WAP5.1 protein (SEQ ID NO: 1). The line TY has an Arginine (R) at amino acid 51, while Charleston Grey has a Glycine (G) at amino acid 51. In the cDNA of line TY the codon at nucleotides 151 to 153 of SEQ ID NO: 11 is 'CGT', while in the cDNA of Charleston Grey the codon is 'GGT' at nucleotides 151 to 153 of SEQ ID NO: 6. Another difference between the alleles is that the codon for S450 is different, while the amino acid (S450) is identical. In the TY line the codon at nucleotides 1348 to 1350 of SEQ ID NO: 11 is 'AGC' (encoding Ser, S), while in the Charleston Grey allele the codon at nucleotides 1348 to 1350 of SEQ ID NO: 6 is 'AGT' (encoding Ser, S). The genomic DNA of the wild type alleles obviously comprises the same differences in these codons.

Thus, in watermelon for example the reference genome Charleston Grey contains a gene encoding the protein of SEQ ID NO: 1, while the reference genome of variety 97103 (genome version v2), and the elite line TY, contains a WAP5.1 gene having 1 amino acid which is different from SEQ ID NO: 1 (amino acid 51), i.e. the protein is 99.9% identical to SEQ ID NO: 1 (in a pairwise alignment such as Emboss-Needle). The N-terminal sequence prior to the F-box is less conserved and these are functional (wild type) WAP5.1 proteins. Therefore, in one aspect functional variants of the watermelon proteins (SEQ ID NO: 1 and SEQ ID NO: 9), cucumber protein (SEQ ID NO: 2) and melon protein (SEQ ID NO: 3) are proteins comprising at least 95%, 96%, 97%, 98%, 99% or 99.5% or 99.6%, 99.7%, 99.8% or 99.9% sequence identity to the proteins of SEQ ID NO: 1, 9, 2 or 3, when aligned pairwise (using e.g. Needle with default parameters).

In one aspect the amino acid sequence variation is prior to the F-box, i.e. in amino acid 1 to 236 of SEQ ID NO: 1 or SEQ ID NO: 9 (watermelon), or in amino acid 1 to 243 of SEQ ID NO: 2 (cucumber) or in amino acid 1 to 246 of SEQ ID NO: 3 (melon). In one aspect the functional proteins, which comprise at least 95%, 96%, 97%, 98%, 99% or 99.5% or 99.6%, 99.7%, 99.8% or 99.9% sequence identity to the proteins of SEQ ID NO: 1, 9, 2 or 3, therefore comprise 100% identical amino acids to SEQ ID NO: 1, 9, 2 or 3 for the region starting at amino acid 237 to the end of SEQ ID NO: 1 or 9, or starting at amino acid 244 to the end of SEQ ID NO: 2, or starting at amino acid 247 to the end of SEQ ID NO: 3, as the variation is prior to the F-box domain.

As the F-box domain and the LRR-domain is highly conserved, both within a species and between species, any mutations in either of these conserved domains is predicted to lead to the mutant WAP5.1 protein having a reduced function or no function in vivo, thereby leading to the facultative parthenocarpic phenotype when the mutant allele is in homozygous form in e.g. a diploid plant.

As mentioned, the F-box is 100% identical between the watermelon, cucumber and melon WAP5.1 proteins. The F-box is a domain which is generally involved in protein-protein interaction, and therefore changing the F-box sequence by inserting, deleting or replacing one or more amino acids in the F-box will negatively affect the protein function.

Therefore, in one aspect a watermelon, cucumber or melon plant or plant part is provided comprising at least one copy of a mutant allele of a gene named WAP5.1, wherein said mutant allele encodes a mutant protein comprising one or more amino acids inserted, deleted or replaced in the F-box domain of the protein starting at amino acid 237 and ending at amino acid 277 of SEQ ID NO: 1 or 9 (watermelon), starting at amino acid 244 and ending at amino acid 284 of SEQ ID NO: 2 (cucumber), starting at amino acid 247 and ending at amino acid 287 of SEQ ID NO: 3 (melon), and wherein said mutant allele confers facultative parthenocarpy when the mutant allele is in homozygous form, and wherein the wild type watermelon allele encodes a protein of SEQ ID NO: 1 or 9 or a protein comprising at least 95%, 96%, 97%, 98%, 99%, 99.5%, 99.8% or 99.9% sequence identity to SEQ ID NO: 1 or 9, the wild type cucumber allele encodes a protein of SEQ ID NO: 2 or a protein comprising at least 95%, 96%, 97%, 98%, 99%, 99.5%, 99.8% or 99.9% sequence identity to SEQ ID NO: 2, and the wild type melon allele encodes a protein of SEQ ID NO: 3 or a protein comprising at least 95%, 96%, 97%, 98%, 99%, 99.5%, 99.8% or 99.9% sequence identity to SEQ ID NO: 3. As mentioned above, the variation of at least 95% 96%, 97%, 98%, 99% or 99.5% or 99.6%, 99.7%, 99.8% or 99.9% sequence identity in the functional wild type proteins is in one aspect at the N-terminal part, preceding the F-box domain, i.e. in the protein region from amino 1 to 236 of SEQ ID NO: 1 or 9 (watermelon), or in the region from amino acid 1 to 243 of SEQ ID NO: 2 (cucumber), or from amino acid 1 to 246 of SEQ ID NO: 3 (melon).

The term 'starting at' and 'ending at' or 'from' and 'to' includes the first and last amino acid mentioned.

The LRR-domain is also highly conserved, both within and between species, as shown in the table below (sequence identity using pairwise alignment of the LRR-domains using Needle, default parameters):

| | Watermelon LRR domain (amino acid 291-1033 of SEQ ID NO: 1 or 9) | Cucumber LRR-domain (amino acid 298 to 1040 of SEQ ID NO: 2) | Melon LRR-domain (amino acid 301 to 1043 of SEQ ID NO: 3) |
|---|---|---|---|
| Watermelon LRR domain (amino acid 291-1033 of | 100% | | |

-continued

| | Watermelon LRR domain (amino acid 291-1033 of SEQ ID NO: 1 or 9) | Cucumber LRR-domain (amino acid 298 to 1040 of SEQ ID NO: 2) | Melon LRR-domain (amino acid 301 to 1043 of SEQ ID NO: 3) |
|---|---|---|---|
| SEQ ID NO: 1 or 9) | | | |
| Cucumber LRR-domain (amino acid 298 to 1040 of SEQ ID NO: 2) | 96.2% | 100% | |
| Melon LRR-domain (amino acid 301 to 1043 of SEQ ID NO: 3) | 98.0% | 97.8% | 100% |

The LRR-domain is a domain which is also generally involved in protein-protein interaction, and therefore changing the LRR-domain sequence by inserting, deleting or replacing one or more amino acids in the LRR-domain will negatively affect the protein function. The LRR-domain is highly structured, as can be seen in the 'tail like' structure into which it folds in the wild type WAP5.1 protein of watermelon, see FIG. 3A. Amino acid substitutions, deletions or insertions can lead to improper folding of the LRR-domain. This can be analysed using the program RaptorX Contact Prediction, as shown in Table 1 below and in FIG. 3B, where a single amino acid substitution (L528F) results in impaired or improper LRR-domain folding (compared to the wild type LRR-domain) and this mutant allele results in facultative parthenocarpy when the allele is in homozygous form.

Therefore, in one aspect a watermelon, cucumber or melon plant or plant part is provided comprising at least one copy of a mutant allele of a gene named WAP5.1, wherein said mutant allele encodes a mutant protein comprising one or more amino acids inserted, deleted or replaced in the LRR-domain of the protein starting at amino acid 291 and ending at amino acid 1033 of SEQ ID NO: 1 or 9 (watermelon), starting at amino acid 298 and ending at amino acid 1040 of SEQ ID NO: 2 (cucumber), starting at amino acid 301 and ending at amino acid 1043 of SEQ ID NO: 3 (melon), preferably wherein said insertion, deletion or replacement resulting in improper folding of the LRR-domain of the protein, and wherein said mutant allele confers facultative parthenocarpy when the mutant allele is in homozygous form, and wherein the wild type watermelon allele encodes a protein of SEQ ID NO: 1 or 9, or a protein comprising at least 95%, 96%, 97%, 98%, 99%, 99.5%, 99.8% or 99.9% sequence identity to SEQ ID NO: 1 or 9, the wild type cucumber allele encodes a protein of SEQ ID NO: 2 or a protein comprising at least 95% sequence identity to SEQ ID NO: 2, and the wild type melon allele encodes a protein of SEQ ID NO: 3 or a protein comprising at least 95% sequence identity to SEQ ID NO: 3. As mentioned above, the variation of at least 95% 96%, 97%, 98%, 99% or 99.5% or 99.6%, 99.7%, 99.8% or 99.9% sequence identity in the functional wild type proteins is in one aspect at the N-terminal part, preceding the F-box domain, i.e. in the protein region from amino 1 to 236 of SEQ ID NO: 1 or 9 (watermelon), or in the region from amino acid 1 to 243 of SEQ ID NO: 2 (cucumber), or from amino acid 1 to 246 of SEQ ID NO: 3 (melon).

Improper folding can be predicted based on RaptorX Contact Prediction, whereby the 3-dimensional model of the LRR-domain or 'tail' shows that the LRR domain folding of the mutant protein deviates from the tail-like folding of the wild type protein, e.g. loops stick out from the tail or the tail is truncated by e.g. at least 5, 10, 15, 20, 30, 40, 50, 60, 70, 80, 90, 100, 110, 120, 130, 140, 150, 160, 170, 180, 190, 200, 250, 300, 350, 400, 450, 500 or more C-terminal amino acids or the entire tail is absent.

Thus, insertion, deletion and/or replacement of one or more amino acids in the LRR-domain, may be the insertion, deletion and/or replacement of at least 1, 2, 3, 4, 5, 6, 7, 8, 9, 10 or more amino acids. Also the deletion of one or more amino acids through mutation of the codon into a STOP codon is encompassed herein.

Mutant alleles can be generated by various techniques, such as random mutagenesis or targeted gene editing, and the phenotype of the mutant allele can then be analysed in plants homozygous for the mutant allele.

Any mutant allele which results in an insertion, deletion and/or replacement of one or more amino acids of the wild type, functional protein may result in a mutant protein having reduced function or no function and may thus result in the phenotype of facultative parthenocarpy when the mutant allele is in homozygous form. In one aspect one or more of any of the amino acids which are conserved between the watermelon WAP5.1 protein of SEQ ID NO: 1 or 9, the cucumber WAP5.1 protein of SEQ ID NO: 2 and the melon WAP5.1 protein of SEQ ID NO: 3 (shown in FIG. 4 as a * underneath the multiple sequence alignment) is replaced by a different amino acid or is deleted or the codon is mutated into a STOP codon. Plants and plant parts comprising such mutant alleles are one embodiment herein.

Herein a number of mutant alleles have been generated in watermelon plants (in the elite TY line), as shown in Table 1 above. These mutant alleles, and watermelon, cucumber or melon plants and plant parts comprising these, are also one aspect. Thus in one aspect the plant or plant part comprises a mutant allele of a WAP5.1 gene, wherein said mutant allele comprises a mutation in the codon encoding amino acid number D209, A257, A266, W274, E287, Q333, L528, P308 or G330 of SEQ ID NO: 1 or of SEQ ID NO: 9 (or of a protein comprising at least 95%, 96%, 97%, 98%, 99%, 99.5%, 99.8% or 99.9% sequence identity to SEQ ID NO: 1 or to SEQ ID NO: 9) or encoding the equivalent amino acid in SEQ ID NO: 2 or 3 (or of a protein comprising at least 95%, 96%, 97%, 98%, 99%, 99.5%, 99.8% or 99.9% sequence identity to SEQ ID NO: 2 or 3). These amino acids are also conserved between the three species, as seen in FIG. 4, where they are highlighted in bold. A mutation in the codon in one aspect changes the codon to encode a different amino acid or to encode a STOP codon.

The 'equivalent amino acid' can easily be determined by amino acid sequence alignment, see e.g. FIG. 4, where the equivalent amino acids of cucumber and melon are highlighted in bold.

A mutation in the codon may be a (at least one) nucleotide insertion, deletion or replacement in the codon, leading to e.g. a different reading frame or a different codon, e.g. encoding a different amino acid or a STOP codon. Also the entire codon may be deleted or replaced by a different codon (or optionally a stop codon), resulting in either a deletion of the encoded amino acid, or the replacement thereof.

In one aspect the mutant allele encodes an amino acid substitution or a stop codon of amino acid number D209, A257, A266, W274, E287, Q333, L528, P308 or G330 of SEQ ID NO: 1 or 9 (or of a protein comprising at least 95%, 96%, 97%, 98%, 99%, 99.5%, 99.8% or 99.9% sequence identity to SEQ ID NO: 1 or to SEQ ID NO: 9) or the equivalent amino acid in SEQ ID NO: 2 or 3 (or of a protein comprising at least 95% sequence identity to SEQ ID NO: 2 or 3).

In a further aspect the mutant allele encodes one or more of the following changes: D209V, A257V, A266V, W274STOP, E287K, Q333STOP, L528F, P308L and/or G330E of SEQ ID NO: 1 or of SEQ ID NO: 9 (or of a protein comprising at least 95%, 96%, 97%, 98%, 99%, 99.5%, 99.8% or 99.9% sequence identity to SEQ ID NO: 1 or to SEQ ID NO: 9) or the equivalent amino acid in SEQ ID NO: 2 or 3 (or of a protein comprising at least 95% sequence identity to SEQ ID NO: 2 or 3).

As mentioned the watermelon, cucumber or melon plant or seed or plant part may comprise a mutant wap5.1 allele, wherein the mutant allele is produced by random mutagenesis or targeted mutagenesis, such as CRISPR based methods. Random mutagenesis may for example be chemical induced (e.g. EMS treatment) or radiation induced mutagenesis or other methods, whereby mutations are randomly induced in the genome and then plants or plant parts comprising mutations in the endogenous wap5.1 gene can be screened for and identified. Targeted mutagenesis are methods whereby mutations are specifically introduced into a target gene, such as the wap5.1 gene, using e.g. Crispr-Cas9, or Crispr-Cpf1 or other known methods. It is noted that using such methods, the mutant alleles described in e.g. Table 1 can be generated without undue burden or other mutant alleles can be made.

When referring herein to a watermelon, cucumber or melon plant this encompasses in one aspect a seed from which the plant can be grown, i.e. the embryo in the seed may comprise at least one copy of mutant wap5.1 allele as described.

In one aspect the plant comprising the mutant allele is not produced exclusively by an essentially biological process, meaning that the mutant allele has at one point been generated by human intervention. If such a human generated mutant allele is transferred from one plant to another by crossing and selection, then the patent covers plants comprising the mutant allele, even if the plant itself has been generated solely by crossing and selection. Preferably the plant is not transgenic, and e.g. any construct used to modify the endogenous gene, in case of targeted gene editing, has been removed from the genome. Also the plant is preferably not a transgenic plant in that the mutant wap5.1 allele has not been introduced from the outside and integrated anywhere in the plant genome using plant transformation techniques, but rather the mutant allele is an endogenous, wild type WAP5.1 allele which has been mutated (using targeted or random mutagenesis) at the locus in the genome where the wild type allele is located.

In one aspect the watermelon, cucumber or melon plant is diploid and comprises at least one copy of a mutant wap5.1 allele as described above, i.e. the plant is heterozygous. As the phenotype is only seen when the mutant allele is in homozygous form, these plants are not facultative parthenocarp, but produce normal seeded fruits upon pollination and no fruits in the absence of pollination of the flowers. Selfing of such heterozygous plants will generate a plant which is homozygous and which comprises two copies of the mutant allele. In one aspect the watermelon, cucumber or melon plant is diploid and comprises two copies of a mutant wap5.1 allele as described above, i.e. the plant is homozygous. The plant is, therefore, also facultative parthenocarp, producing seedless fruits in the absence of pollination and seeded fruits if pollination takes place.

The plants and plant parts comprising at least one copy of a mutant wap5.1 allele is preferably a cultivated plant, not a wild plant. So preferably cultivated watermelon (*Citrullus lanatus*), cultivated cucumber (*Cucumis sativus*) or cultivated melon (*Cucumis melo*). The plant may be an inbred line, a F1 hybrid or a breeding line.

In one aspect the plant is a watermelon plant and the watermelon plant is diploid, triploid or tetraploid, comprising at least one copy of a mutant wap5.1 allele. The diploid plant or plant part comprises in one aspect two copies, the triploid plant or plant part comprises one, two or three copies and the tetraploid plant or plant part comprises two or four copies of the mutant wap5.1 allele.

Also seeds from which a plant or plant part as described above can be grown are encompassed herein.

Likewise a fruit produced by a plant described above is encompassed herein, optionally wherein the fruit is seedless and is produced in the absence of pollination.

The plant or plant part according may further comprises a gene conferring male sterility or a gene conferring steno-spermocarpy or another gene conferring parthenocarpy.

The plant part may be a cell, a flower, a leaf, a stem, a cutting, an ovule, pollen, a root, a rootstock, a scion, a fruit, a protoplast, an embryo, an anther.

Further a vegetatively propagated plant propagated from a plant part and comprising at least one copy of a mutant wap5.1 allele in its genome is provided.

In one aspect also a method of producing seedless watermelon fruits is provided, said method comprising growing a diploid watermelon plant comprising two copies of a mutant wap5.1 allele as described, whereby pollination of the flowers is prevented during the growing. Preventing pollination can be done by various methods, e.g. removal of male flowers or male reproductive organs (stamen, pollen), growing in insect free environments and/or male sterility of the plant.

In a further aspect a method of producing seedless watermelon fruits is provided, said method comprising growing a triploid watermelon plant comprising one, two or three copies of mutant wap5.1 allele as described, whereby no pollenizer plant is present during the growing.

A method for screening or detecting or genotyping plants, seeds, plant parts or DNA therefrom for the presence of a mutant allele of a of a gene named WAP5.1, or for selecting a plant, seed or plant part comprising a mutant allele of a of a gene named WAP5.1, or for generating a plant, seed or plant part comprising a mutant allele of a gene named WAP5.1, is provided, wherein said mutant allele either a) comprises one or more mutations in a regulatory element, resulting in no expression or reduced expression of the allele compared to the wild type allele, and/or b) encodes a mutant protein comprising one or more amino acids replaced, inserted or deleted compared to the wild type protein, wherein the wild type watermelon allele encodes a protein of SEQ ID NO: 1 or 9 or a protein comprising at least 95% sequence identity to SEQ ID NO: 1 or 9, the wild type cucumber allele encodes a protein of SEQ ID NO: 2 or a protein comprising at least 95% sequence identity to SEQ ID NO: 2, and the wild type melon allele encodes a protein of SEQ ID NO: 3 or a protein comprising at least 95% sequence identity to SEQ ID NO: 3.

In one aspect the mutant wap5.1 allele comprises a mutation in the genomic DNA, resulting in the expression of a mutant WAP5.1 protein comprising one or more amino acids inserted, deleted or replaced as described above, e.g. D209, A257, A266, E287, W274, Q333, L528, P308 or G330 of SEQ ID NO: 1 or of SEQ ID NO: 9 (or the equivalent amino acid in a sequence comprising at least 95% identity to SEQ ID NO: 1 or 9) or the equivalent amino acid in SEQ ID NO: 2 or 3 (or a sequence comprising at least 95% identity to SEQ ID NO: 2 or 3).

However, also different mutant alleles of the WAP5.1 gene, causing facultative parthenocarpy when in homozygous form, are embodiments of the invention. Such different mutant wap5.1 alleles can be generated by the skilled person without undue burden. The skilled person can, for example, generate other mutants in the WAP5.1 gene and determine whether they equally result in facultative parthenocarpy when in homozygous form in a diploid watermelon, cucumber or melon plant.

Having identified the nucleotide sequence of the gene, the skilled person can generate watermelon, melon or cucumber plants comprising mutants in the WAP5.1 gene by various methods, e.g. mutagenesis, TILLING or CRISPR-Cas or other methods known in the art. Especially with targeted gene modification technologies such as Crispr-Cas, TAL-ENS and others, targeted mutations can be made by the person skilled in the art. He can then confirm the phenotype of a plant homozygous for the mutant wap5.1 allele, i.e. being facultative parthenocarpic. Therefore, the skilled person is not limited to the specific WAP5.1 mutants generated by the inventors (which the skilled person can also generate), but the skilled person can equally generate other mutations in the wap5.1 allele of watermelon, and also of cucumber and melon, and thereby generate other mutants which lead to facultative parthenocarpy when in homozygous form. Various mutations can be generated and tested for the resulting phenotype, for example the regulatory elements can be mutated to reduce expression (knock-down) or eliminate expression (knock-out) of the allele and thus reduce or eliminate the amount of WAP5.1 protein present in the cell or plant. Alternatively, mutations which lead to reduced function or loss-of-function of the WAP5.1 protein can be generated, i.e. mutations (such as missense mutations or frame shift mutations) which lead to one or more amino acids being substituted, inserted or deleted, or whereby the protein is truncated through the introduction of a stop-codon in the coding sequence (non-sense mutations). As the WAP5.1 protein comprises two conserved domains, the "F-box domain" and the "LRR-domain", it is in one aspect encompassed that one or more amino acids are replaced, deleted or inserted in either of these domains, as such mutations will likely reduced the protein function or result in a loss of function. Whether the mutation results in the expected phenotype (facultative parthenocarpy) can then be tested by generating plants homozygous for the mutation through selfing and growing the plant line with and without pollination of the flowers to see if fruits develop in a facultative parthenocarpic way.

Alternatively, the skilled person can carry out a method for production of a facultative parthenocarpic cultivated watermelon, cucumber or melon plant comprising the steps of:

a) introducing mutations in a (population of) watermelon, cucumber or melon plant(s) or seed(s), especially a cultivated plant, or providing a (population of) mutated plant(s) or seed or progeny thereof;

b) selecting a plant producing seedless fruits without pollination of the female flowers and producing a seeded fruit after pollination of the female flowers;

c) optionally determining if the plant selected under b) comprises a mutant allele of a WAP5.1 gene; and d) optionally growing the plants obtained under c).

Steps b) and c) can also be switched, so that step b) is selecting a plant comprising a mutant allele of a WAP5.1 gene and step c) is determining if the plant (or a progeny thereof produced by selfing) producing seedless fruits without pollination of the female flowers and producing a seeded fruit after pollination of the female flowers.

Step a) can be carried out by e.g. mutagenizing seeds of one or more lines or varieties of watermelon, cucumber or melon, for example by treatment with mutagenizing agents such as chemical mutagens, e.g. EMS (ethyl methane sulphonate), or irradiation with UV radiation, X-rays or gamma rays or the like. The population may for example be a TILLING population. Preferably the mutagenized plant population is selfed at least once (e.g. to produce an M2 generation, or M3, M4, etc.) prior to carrying out step b). In step b) relating to phenotyping, plants are preferably grown in an insect proof environment to avoid the presence of insect pollinators. Regular visual inspection of female flowers, fruit setting of those flowers without pollination and visual inspection of the mature fruits (e.g. presence of viable seeds or seedless) can be carried out to identify mutants which producing seedless fruits without pollination of the female flowers. Such plants, or selfing progeny thereof, can be tested for the presence of the mutant WAP5.1 gene by pollinating the female flowers to see if the fruits are seeded after pollination, genotyping the plants for mutations in the WAP5.1 gene and encoded protein, or expression of the WAP5.1 gene, sequencing and other methods known to the skilled person. There are, thus, various methods, or combinations of methods, for verifying if a phenotypically selected plant comprises a mutant allele of a WAP5.1 gene.

If step b) is the selection of plants comprising a mutant allele of the WAP5.1 gene, the skilled person can also use various methods for detecting the DNA, mRNA or protein of the WAP5.1 gene in order to identify a plant comprising a mutant wap5.1 allele. The genomic DNA of the wild type watermelon wap5.1 gene, encoding a functional WAP5.1 protein (SEQ ID NO: 1) is the DNA of SEQ ID NO: 7 and the cDNA (mRNA) encoding the protein of SEQ ID NO: 1 is given in SEQ ID NO: 6. The genomic DNA of the wild type watermelon wap5.1 gene, encoding a functional WAP5.1 protein (SEQ ID NO: 9) is the DNA of SEQ ID NO: 14 and the cDNA (mRNA) encoding the protein of SEQ ID NO: 9 is given in SEQ ID NO: 11. The promoter is upstream of this sequence and can e.g. be retrieved by sequencing or from the watermelon genome database. Likewise, the promoter sequences of the cucumber or melon WAP5.1 genes can be easily retrieved by the skilled person. As genomic sequences encoding a certain protein may vary slightly (e.g. due to degeneracy of the genetic code or due to variation in intron sequences), the genomic alleles encoding a wild type WAP5.1 protein may comprise at least 90%, 92%, 93%, 94%, 95%, 96%, 97%, 98%, 99% sequence identity to SEQ ID NO: 7 and/or to SEQ ID NO: 14.

In one aspect the mutant allele of the WAP5.1 gene is a mutant allele resulting in reduced expression or no expression of the WAP5.1 gene or is a mutant allele resulting in one or more amino acids of the encoded WAP5.1 protein being replaced, inserted or deleted, compared to the wild type WAP5.1 protein.

In one aspect the mutant allele of the WAP5.1 gene is obtainable by inducing mutations, either targeted or random, into the gene (promoter or other regulatory elements, splice sites, coding region, etc.) and selecting plants, e.g. from the progeny, comprising a mutant wap5.1 allele. In one aspect an allele comprising a mutation in a codon, especially in a codon of the F-box or of the LRR-domain is selected, e.g. a mutation which causes an amino acid replacement, a frame shift or a stop-codon. In one aspect the mutant allele causes the changes shown in Table 1 in the watermelon WAP5.1 gene or the equivalent change in the cucumber or melon WAP5.1 gene.

In one aspect the SNP marker Thymine (T) at nucleotide 61 of SEQ ID NO: 8 (marker mWM23348429) is detected in the genome of a watermelon, melon or cucumber plant or plant part, or DNA therefrom.

This SNP marker detects the allele comprising the L528F mutation in watermelon, or the corresponding amino acid change in the cucumber or melon wap5.1 allele. It is noted that the genomic region comprising the Thymine can be at least 92%, 93%, 94%, 95%, 96% or 97% identical to the sequence of SEQ ID NO: 8, as there are two 'Y' nucleotides in the sequence, referring to the nucleotide being a Pyrimidine (C of T) and there may be other non-identical nucleotides in the genomic sequence flanking the SNP at nucleotide 61 of SEQ ID NO: 8. Blast of SEQ ID NO: 8 against the watermelon Charleston Grey genome, for example, shows that SEQ ID NO: 8 is 97.52% identical to the Charleston Grey reference genome, which lacks the mutation and comprises a C (Cytosine) at nucleotide 61 of the genomic sequence.

For other mutant wap5.1 alleles, similar SNP markers (or other markers) and SNP genotyping (or other genotyping) assays can easily be designed. Thus, allele specific markers and detection methods are encompassed herein, especially for any mutant allele which results in an amino acid insertion, deletion or replacement in the F-box or the LRR-domain of a WAP5.1 protein of watermelon, cucumber or melon.

Especially in one aspect the genotype of marker mWM23348429 can be determined and used to select plants or progeny plants comprising a Thymine at nucleotide 61 of SEQ ID NO: 8 and thus comprising the mutant wap5.1 allele in which amino acid L528 of SEQ ID NO: 1 or 9 (or the corresponding amino acid of a sequence comprising at least 95% identity to SEQ ID NO: 1 or 9) is replaced by F (phenylalanine), or in which the corresponding L (Leucine) in melon or cucumber is replaced by F (Phenylalanine), wherein the corresponding amino acid is L535 in cucumber of SEQ ID NO: 2 (or the corresponding amino acid of a sequence comprising at least 95% identity to SEQ ID NO: 2) and L538 in melon of SEQ ID NO: 3 or the corresponding amino acid of a sequence comprising at least 95% identity to SEQ ID NO: 3).

The diploid plant heterozygous for wap5.1 (i.e. wap5.1/WAP5.1) will be heterozygous for the SNP marker, e.g. will have the genotype 'TC' for nucleotide 61 of SEQ ID NO: 8 (i.e. the plant comprises one chromosome having a Thymine, T, at nucleotide 61 of SEQ ID NO: 8 or at nucleotide 61 of a sequence comprising at least 92%, 93%, 94%, 95%, 96%, 97%, 98% or more sequence identity to SEQ ID NO:8 and a second chromosome having a Cytosine, C, at nucleotide 61 of SEQ ID NO: 8 or at nucleotide 61 of a sequence comprising at least 92%, 93%, 94%, 95%, 96%, 97%, 98% or more sequence identity to SEQ ID NO:8), while a plant homozygous for wap5.1 (i.e. wap5.1/wap5.1) will have the genotype 'T' for nucleotide 61 of SEQ ID NO: 8 (i.e. the plant comprises two chromosomes which both have a Thymine, T, at nucleotide 61 of SEQ ID NO: 8 or at nucleotide 61 of a sequence comprising at least 92%, 93%, 94%, 95%, 96%, 97%, 98% or more sequence identity to SEQ ID NO:8).

The marker mWM23348429 was designed based on the induced mutation of nucleotide 4123 (Cytosine) in the genomic DNA of the wild type WAP5.1 gene of SEQ ID NO: 7 to Thymine (C41234T), whereby the codon CU (encoding Leucine) is changed into the codon TTT encoding Phenylalanine, resulting in the L528P substitution in the watermelon WAP5.1 protein. Thus, nucleotide 4123 of the genomic WAP5.1 sequence of SEQ ID NO: 7 corresponds to nucleotide 61 of marker mWM23348429 of SEQ ID NO: 8.

Likewise, in the genomic DNA of SEQ ID NO: 14 marker mWM23348429 comprises the SNP for the mutation at nucleotide 4118 (Cytosine) in the genomic DNA of the wild type WAP5.1 gene of SEQ ID NO: 14 to Thymine (C41184 T), whereby the codon CTT (encoding Leucine) is changed into the codon TTT encoding Phenylalanine, resulting in the L528P substitution in the watermelon WAP5.1 protein.

Mutant-allele-specific markers and marker assays can equally easily be developed for any mutant wap5.1 allele, as the underlying genomic change, e.g. in a codon, can be used to design a marker assay to detect the genomic change, e.g. underlying the amino acid changes disclosed in Table 1 or other genomic changes in the mutant wap5.1 allele compared to the wild type WAP5.1 allele.

Using such allele-specific markers, which detect specific mutant wap5.1 alleles, genotyping can be carried out to detect the presence and copy number of the allele in plants and plant material (or DNA derived therefrom). So in diploids, the marker genotype for the above mutant wap5.1 allele (underlying the L528F change of the protein in watermelon or corresponding change in cucumber or melon) is 'TT' when the mutant allele is in homozygous form. In triploids or tetraploids the marker genotype can be used to determine copy number of the mutant allele. The genotype may thus for example be TTT if three copies are present in a triploid, or TTTT if for copies are present in a tetraploid, or TTC if two copies are present in a triploid, etc.

Plants and Plant Parts

In one embodiment a cultivated watermelon, cucumber or melon plant is provided, or a part thereof (such as a cell, a tissue, organ, fruit, etc.), comprising at least one copy of a mutant allele of a gene named WAP5.1, said mutant allele conferring facultative parthenocarpy when the mutant allele is in homozygous form.

In one aspect the mutant allele is a mutant allele of the watermelon gene which encodes the WAP5.1 protein of SEQ ID NO: 1 or of SEQ ID NO: 9, or a protein comprising at least 95%, 96%, 97%, 98%, 99%, 99.5% or 99.9% sequence identity to SEQ ID NO: 1 or to SEQ ID NO: 9 (wild type functional protein), or is a mutant allele of the cucumber gene which encodes the WAP5.1 protein of SEQ ID NO: 2 or a protein comprising at least 95%, %%, 97% 98%, 99%, 99.5% or 99.9% sequence identity to SEQ ID NO: 2 (wild type functional protein), or is a mutant allele of the melon gene which encodes the WAP5.1 protein of SEQ ID NO: 3 or a protein comprising at least 95%, %%, 97%, 98%, 99%, 99.5% or 99.9% sequence identity to SEQ ID NO: 3 (wild type functional protein), whereby the mutant allele has a reduced expression or no expression, or whereby the mutant allele encodes a mutant WAP5.1 protein comprising one or more amino acids replaced, inserted or deleted compared to the wild type protein.

In one embodiment the one or more amino acid replacements, insertions or deletions comprise or consist of the replacement, insertion or deletion of one or more amino acids in one or both of the conserved domains, i.e. the F-box domain and the LRR-domain. The mutant protein has a reduced-function or loss-of-function compared to the wild type protein (and thus compared to a wild type plant comprising the wild type WAP5.1 gene), preferably the plant cell or plant comprising the mutant allele in homozygous form is facultative parthenocarpic.

When referring herein to a specific nucleotide or amino acid position, e.g. at amino acid 528 of SEQ ID NO: 1 or 9, "or at amino acid 528 of a sequence comprising at least 95%, 96%, 97%, 98%, 99%, 99.5% or 99.9% sequence identity to the SEQ ID NO" (or 'at the equivalent position in a sequence comprising at least 95% . . . '), this means that the nucleotide or amino acid is present in a variant sequence at a nucleotide or amino acid corresponding to the same nucleotide or amino acid (e.g. corresponding to amino acid 528 of SEQ ID NO: 1 or 9) in the variant sequence, i.e. in a sequence comprising at least 95%, 96%, 97%, 98%, 99%, 99.5% or 99.9% sequence identity to the mentioned SEQ ID NO. It may for example be that the variant sequence is one or a few nucleotides or amino acids shorter, but when one pairwise aligns the variant sequence with the mentioned SEQ ID NO, one can see which nucleotide or amino acid of the variant sequence corresponds to the same nucleotide or amino acid. In the variant sequence this may for example be amino acid 527 or 529 of that variant sequence which corresponds to amino acid 528 of the mentioned sequence.

The mutant allele is a mutation in an endogenous gene of cultivated watermelon, cucumber and melon. The existence of a gene conferring facultative parthenocarpy enables the skilled person to generate other de novo mutants in the gene, e.g. in any cultivated line or variety.

The skilled person can, without undue burden, generate plants according to the invention, e.g. by carrying out a method for generation and/or identification of WAP5.1 mutants in a mutant population or by targeted gene editing of the WAP5.1 gene.

As mentioned above, as the WAP5.1 gene has been identified to be the gene encoding a protein of SEQ ID NO: 1 or 9 (wild type watermelon protein) in normal, non-parthenocarpic watermelon plants, other mutants than the ones generated by the inventors (e.g. encoding the mutant protein of SEQ ID NO: 4 or of SEQ ID NO: 10, or other mutant proteins mentioned in Table 1 above) can be generated de novo. The same holds true for cucumber and melon, also here any mutants can be generated de novo.

As natural variation may exist in the wild type, functional WAP5.1 proteins, the wild type WAP5.1 protein need not be 100% identical to the protein of SEQ ID NO: 1, 9, 2 or 3, but may have less sequence identity to SEQ ID NO: 1, 9, 2 or 3, e.g. at least 95% 96%, 97%, 98%, 99% or 99.5% or 99.6%, 99.7%, 99.8% or 99.9% when aligned pairwise over the entire length to SEQ ID NO: 1, 9, 2 or 3. In one aspect the conserved F-box domain is however 100% identical to that of SEQ ID NO: 1, 9, 2, or 3, so that the variation of at least 95% identity lies outside of the F-box domain. In another aspect the conserved LRR-domain is 100% identical to that of SEQ ID NO: 1, 9, 2 or 3, so that the variation of at least 95% identity lies outside of the LRR-domain. In a further aspect the variation of at least 95% identity lies outside of the LRR-domain and outside of the LRR-domain. In another aspect the variation of at least 95% sequence identity in the functional wild type proteins of SEQ ID NO: 1, 9, 2 or 3 is at the N-terminal part, preceding the F-box domain, i.e. in the protein region from amino 1 to 236 of SEQ ID NO: 1 or 9 (watermelon), or in the region from amino acid 1 to 243 of SEQ ID NO: 2 (cucumber), or from amino acid 1 to 246 of SEQ ID NO: 3 (melon).

As mentioned, a mutant allele of a WAP5.1 protein-encoding gene causes a plant to produce seedless fruits in the absence of pollination and seeded fruits in the presence of pollination, when the plant is homozygous for the mutant allele, especially a diploid plant homozygous for the mutant allele and optionally a triploid plant comprising at least one, two or three copies of the mutant allele or a tetraploid plant comprising at least two or four copies of the mutant allele. Concerning the embodiments of the invention, the mutation in the mutant allele of a WAP5.1 protein-encoding gene can be any mutation, including deletions, truncations, insertions, point mutations, nonsense mutations, missense or non-synonymous mutations, splice-site mutations, frame shift mutations and/or mutations in regulatory sequences. In one aspect the mutation in the mutant allele of a WAP5.1 protein-encoding gene is a point mutation. The mutation can occur in a DNA sequence comprising the coding sequence of a WAP5.1 protein-encoding gene or in a RNA sequence encoding a WAP5.1 protein or it can occur in the amino acid of a WAP5.1 protein. Concerning a DNA sequence of a WAP5.1 protein-encoding gene the mutation can occur in the coding sequence or it can occur in non-coding sequences like 5'- and 3'-untranslated regions, promoters, enhancers etc. of a WAP5.1 protein-encoding gene. In respect to RNA encoding a WAP5.1 protein the mutation can occur in the pre-mRNA or the mRNA. In one aspect the mutant allele results in the protein having a loss-of-function or decrease of function due to one or more amino acids being replaced, inserted and/or deleted, for example resulting in one or more amino acids being replaced, inserted or deleted in the conserved F-box domain or in the LRR-domain. For example, truncation of the protein to cause deletion of either or both of these domains, or a part of either of these domains, will result in a loss of function or decrease of function of the protein. Thus, stop codon mutations e.g. in the N-terminal part preceding the F-box domain (amino acid 1 to 236 of SEQ ID NO: 1 or 9 or a sequence comprising at least 95% sequence identity to SEQ ID NO: 1 or 9; amino acid 1 to 243 of SEQ ID NO: 2 or a sequence comprising at least 95% sequence identity to SEQ ID NO:2; amino acid 1 to 246 of SEQ ID NO: 3 or a sequence comprising at least 95% sequence identity to SEQ ID NO:3) or in one of the conserved domains result in truncated proteins having a reduced function or loss of function.

Likewise, amino acid insertions, deletions or replacements in the N-terminal part preceding the F-box domain or one of the conserved domains, i.e. the F-box domain or the LRR-domain, can result in a protein having a reduced function or loss of function.

In one aspect any amino acid insertion, deletion and/or replacement which results in a deviant/improper 3-dimension protein folding as predicted by RaptorX Contact Prediction analysis is likely to result in reduced in vivo function or no function of the mutant WAP5.1 protein.

Any mutant allele can be analysed for the phenotype when the allele is in homozygous form in e.g. diploid plants, to see if indeed the plant becomes facultative parthenocarp.

One embodiment of the invention therefore concerns plant cells or plants according to the invention comprising a mutant allele of a WAP5.1 protein-encoding gene characterized in that the mutant allele comprises or effects one or more of the mutations selected from the group consisting of a) a deletion, truncation, insertion, point mutation, nonsense mutation, missense or non-synonymous mutation, splice-site mutation, frame shift mutation in the genomic sequence;

b) a mutation in one or more regulatory sequences;

c) a deletion, truncation, insertion, point mutation, nonsense mutation, missense or non-synonymous mutation, splice-site mutation, frame shift mutation in the coding sequence;

d) a deletion, truncation, insertion, point mutation, nonsense mutation, missense or non-synonymous mutation, splice-site mutation, frame shift mutation in the pre-mRNA or mRNA; and/or e) a deletion, truncation, insertion or replacement of one or more amino acids in the WAP5.1 protein.

In one aspect the mutant allele results in reduced expression or no expression of the WAP5.1 gene or the mutant allele encodes a protein having a decreased function or a loss-of-function.

Reduced expression or no expression means that there is a mutation in a regulatory region of the WAP5.1 gene, such as the promoter, whereby reduced mRNA transcript or no mRNA transcript of the WAP5.1 allele is being made, compared to plants and plant parts comprising a wild type WAP5.1 allele. The decrease in the expression can, for example, be determined by measuring the quantity of mRNA transcripts encoding WAP5.1 protein, e.g. using Northern blot analysis or RT-PCR. Here, a reduction preferably means a reduction in the amount of RNA transcripts by at least 50%, in particular by at least 70%, optionally by at least 85% or by at least 95%, or even by 100% (no expression) compared to the plant or plant part comprising a wild type WAP5.1 gene. Expression can be analysed e.g. in young leaf tissue or ovary tissue.

In one aspect the protein comprising one or more amino acids replaced, inserted or deleted compared to the wild type protein. Thus, for watermelon, one or more amino acids are inserted, deleted or replaced compared to the wild type WAP5.1 protein of SEQ ID NO: 1 or 9, or a wild type WAP5.1 protein comprising at least 95%, 96%, 97%, 98%, 99%, 99.5% or 99.9% sequence identity to SEQ ID NO: 1 or 9; for cucumber, one or more amino acids are inserted, deleted or replaced compared to the wild type WAP5.1 protein of SEQ ID NO: 2 or a wild type WAP5.1 protein comprising at least 95%, 96%, 97% 98%, 99%, 99.5% or 99.9% sequence identity to SEQ ID NO: 2; for melon, one or more amino acids are inserted, deleted or replaced compared to the wild type WAP5.1 protein of SEQ ID NO: 3 or a wild type WAP5.1 protein comprising at least 95%, 96%, 97% 98%, 99%, 99.5% or 99.9% sequence identity to SEQ ID NO: 3, whereby the mutant protein has reduced function or loss of function compared to the wild type protein and, thus, results in facultative parthenocarpy when the mutant allele is present in homozygous form in a diploid plant.

In one aspect the wild type WAP5.1 protein comprises the conserved F-box domain. Thus in one aspect the mutant allele is a mutant allele of the gene WAP5.1, which gene encodes a wild type protein of SEQ ID NO: 1 or 9 (watermelon) or of SEQ ID NO: 2 (cucumber) or of SEQ ID NO: 3 (melon), or a wild type protein comprising at least 95%, 96%, 97% 98%, 99%, 99.5% or 99.9% sequence identity to SEQ ID NO: 1 or 9, SEQ ID NO: 2 or SEQ ID NO: 3, and whereby the wild type protein comprises the conserved F-box domain of amino acids 237 to 277 of SEQ ID NO: 1 or 9.

In one aspect the wild type WAP5.1 protein comprises the conserved LRR-domain. Thus in one aspect the mutant allele is a mutant allele of the gene WAP5.1, which gene encodes a wild type protein of SEQ ID NO: 1 or 9 (watermelon) or of SEQ ID NO: 2 (cucumber) or of SEQ ID NO: 3 (melon), or a wild type protein comprising at least 95%, 96%, 97% 98%, 99%, 99.5% or 99.9% sequence identity to SEQ ID NO: 1 or 9, SEQ ID NO: 2 or SEQ ID NO: 3, and whereby the watermelon wild type protein comprises the conserved LRR-domain of amino acids 291 to 1033 of SEQ ID NO: 1 or 9 (watermelon), the cucumber wild type protein comprises the conserved LRR-domain of amino acids 298 to 1040 of SEQ ID NO: 2 (cucumber), or the melon wild type protein comprises the conserved LRR-domain of amino acid 301 to 1043 of SEQ ID NO: 3 (melon).

In one aspect the wild type WAP5.1 protein comprises the conserved F-box and LRR-domain, i.e. any variation of the functional wild type protein is in the N-terminal preceding the F-box domain. Thus in one aspect the mutant allele is a mutant allele of the gene WAP5.1, which gene encodes a wild type protein of SEQ ID NO: 1 or 9 (watermelon) or of SEQ ID NO: 2 (cucumber) or of SEQ ID NO: 3 (melon), or a protein comprising at least 95%, 96%, 97% 98%, 99%, 99.5% or 99.9% sequence identity to SEQ ID NO: 1 or 9, SEQ ID NO: 2 or SEQ ID NO: 3, and whereby the watermelon wild type protein comprises amino acids 237 to 1033 of SEQ ID NO: 1 or 9 (watermelon), the cucumber wild type protein comprises amino acids 244 to 1040 of SEQ ID NO: 2 (cucumber), or the melon wild type protein comprises amino acid 247 to 1043 of SEQ ID NO: 3 (melon).

The mutant alleles of the above wild type alleles are in one aspect mutant alleles having reduced expression or no expression (through e.g. mutations in the promoter or enhancer elements) or producing a mutant protein which comprises one or more amino acids inserted, deleted or replaced compared to the wild type protein, whereby e.g. the 3-dimensional protein folding of the mutant protein is deviant from the wild type folding, as can be analysed by RaptorX Contact Prediction and/or the mutant protein has a reduced function or no function in vivo, as can be determined when the mutant allele is in homozygous form in a plant and by analysing whether the plant produces fruits in the absence of pollination (parthenocarpy), e.g. when grown in an insect free environment and the (female) flowers produce fruits despite not being pollinated. Also, plants can be tested as to whether they produce fruits normal, seeded fruits when the (female) flowers are pollinated. If the mutant allele causes facultative parthenocarpy in vivo, while the control plant comprising only the wild type WAP5.1 alleles is not facultative parthenocarp, then the mutant protein has a reduced function or no function compared to the wild type protein. The same phenotypic analysis can be done for a mutant allele having reduced gene expression or no gene expression. Thus, any mutant allele can be made homozygous in the plant and the phenotype can be compared to the control plant comprising the original, non-mutated allele.

The F-box domain was found to be identical between the three Cucurbitaceae species, watermelon, melon and cucumber, as shown in FIG. 4. It comprises the sequence LTD-DLLHMVFSFLDHINLCRAAIVCRQWQAASA-HEDFWRCL (SEQ ID NO: 13), which is present in wild type ClWAP5.1 of SEQ ID NO: 1 and 9, from amino acid 237 to 277, in wild type CsWAP5.1 of SEQ ID NO: 2, from amino acid 244 to 284, and in wild type CmWAP5.1 of SEQ ID NO: 3, from amino acid 247 to 287.

Most likely, the F-box will be 100% identical in other wild type, functional WAP5.1 variants also, as it is highly conserved and required for proper functioning of the protein (most likely through protein-protein interaction). Therefore, mutating the F-box by inserting, deleting or replacing one or more of its amino acids will reduce or abolish the WAP5.1 protein function in vivo.

In one aspect, therefore, a plant provided herein comprises a mutant WAP5.1 allele which encodes a WAP5.1 protein comprising one or more amino acids inserted, deleted or replaced in the F-box domain of sequence LTD-DLLHMVFSFLDHINLCRAAIVCRQWQAASA-HEDFWRCL (SEQ ID NO: 13). The wild type, functional WAP5.1 protein which is mutated to comprise one or more amino acids inserted, replaced or deleted is selected from the ClWAP5.1 of SEQ ID NO: 1 or SEQ ID NO: 9 or a protein comprising at least 95% identity to SEQ ID NO: 1 or 9, the CsWAP5.1 of SEQ ID NO: 2 or a protein comprising at least 95% identity to SEQ ID NO: 2, and the CmWAP5.1 of SEQ ID NO: 3 or a protein comprising at least 95% identity to SEQ ID NO: 3, whereby all of the wild type proteins comprise the F-box domain of the sequence LTD-DLLHMVFSFLDHINLCRAAIVCRQWQAASA-HEDFWRCL (SEQ ID NO: 13).

In a further aspect wild type, functional WAP5.1 protein which is mutated to comprise one or more amino acids inserted, replaced or deleted is selected from ClWAP5.1 of SEQ ID NO: 1 or of SEQ ID NO: 9, or a protein comprising at least 95% identity to SEQ ID NO: 1 or 9, CsWAP5.1 of SEQ ID NO: 2 or a protein comprising at least 95% identity to SEQ ID NO: 2, and CmWAP5.1 of SEQ ID NO: 3 or a protein comprising at least 95% identity to SEQ ID NO: 3, whereby all of the wild type proteins comprise the F-box domain of the sequence LTDDLLHMVFSFLDHINL-CRAAIVCRQWQAASAHEDFWRCL (SEQ ID NO: 13) and whereby the 'at least 95%' sequence variation is found in the N-terminal part of the protein, preceding the F-box domain. The region starting from the start of the F-box to the end of the protein is thus, in one aspect, 100% identical in sequence to SEQ ID NO: 1, 9, 2, or 3.

A mutant protein comprising a frame shift leading to a change of one or more amino acids in the F-box domain or a mutant protein comprising a truncation leading to the deletion of one or more amino acids of the F-box domain is hereby encompassed as being a mutant protein comprising reduced function or no function in vivo.

Three specific mutants in the F-box domain have been generated in watermelon, as shown in Table 1 and FIG. 4. In one aspect a watermelon, cucumber or melon plant comprising any of those three specific mutants in the F-box domain of the ClWAP5.1, CsWAP5.1 or CmWAP5.1 protein, respectively, is encompassed herein.

In one aspect therefore a mutant ClWAP5.1 allele is provided encoding a mutant protein wherein the A257 of SEQ ID NO: 1 or of SEQ ID NO: 9 (or a sequence comprising at least 95% identity to SEQ ID NO: 1 or 9), the A266 of SEQ ID NO: 1 or 9 (or a sequence comprising at least 95% identity to SEQ ID NO: 1 or 9) and/or the W274 of SEQ ID NO: 1 or 9 (or a sequence comprising at least 95% identity to SEQ ID NO: 1 or 9) is replaced by another amino acid or is deleted.

In another aspect therefore a mutant CsWAP5.1 allele is provided encoding a mutant protein wherein the A264 of SEQ ID NO: 2 (or a sequence comprising at least 95% identity to SEQ ID NO: 2), the A273 of SEQ ID NO: 2 (or a sequence comprising at least 95% identity to SEQ ID NO: 2) and/or the W281 of SEQ ID NO: 2 (or a sequence comprising at least 95% identity to SEQ ID NO: 2) is replaced by another amino acid or is deleted.

In another aspect therefore a mutant CmWAP5.1 allele is provided encoding a mutant protein wherein the A267 of SEQ ID NO: 3 (or a sequence comprising at least 95% identity to SEQ ID NO: 3), the A276 of SEQ ID NO: 3 (or a sequence comprising at least 95% identity to SEQ ID NO: 3) and/or the W284 of SEQ ID NO: 3 (or a sequence comprising at least 95% identity to SEQ ID NO: 3) is replaced by another amino acid or is deleted.

When amino acids from one amino acid to another amino acid are mentioned herein this includes the start/first and end/last amino acid mentioned.

The LRR-domain was found to be highly conserved between the three Cucurbitaceae species, watermelon, melon and cucumber, as shown in FIG. 4. The LRR-domain is 96.2% identical between watermelon and cucumber, 98% between watermelon and melon and 97.8% between cucumber and melon (in a pairwise alignment using Emboss-Needle). It is also highly structured, as it folds into a kind of 'tail', as can be seen in FIG. 3A.

The LRR-domain is present in wild type ClWAP5.1 of SEQ ID NO: 1 and SEQ ID NO: 9 from amino acid 291 to 1033, in wild type CsWAP5.1 of SEQ ID NO: 2 from amino acid 298 to 1040 and in wild type CmWAP5.1 of SEQ ID NO: 3 from amino acid 301 to 1043. Most likely, the LRR-domain will be at least 95%, 96%, 97%, 98% or 99% identical to the LRR-domain of SEQ ID NO: 1, 9, 2 or 3 in other wild type, functional WAP5.1 variants also, as it is highly conserved and is required for proper 3-dimensional folding and proper functioning of the protein (most likely through protein-protein interaction). Therefore, mutating the LRR-domain by inserting, deleting or replacing one or more of its amino acids will result in a different 3-dimensional protein folding of the domain and/or reduce or abolish the WAP5.1 protein function in vivo.

In one aspect, therefore, a plant provided herein comprises a mutant WAP5.1 allele which encodes a WAP5.1 protein comprising one or more amino acids inserted, deleted or replaced in the LRR-domain of SEQ ID NO: 1, 9, 2 or 3, or in the LRR-domain which is at least 95%, 96%, 97%, 98% or 99% identical to the LRR-domain of SEQ ID NO: 1, 9, 2 or 3.

In another aspect, therefore, a plant provided herein comprises a mutant WAP5.1 allele which encodes a WAP5.1 protein comprising one or more amino acids inserted, deleted or replaced in the LRR-domain of SEQ ID NO: 1, 9, 2 or 3, or in the LRR-domain of a variant wild type WAP5.1 protein, which wild type protein comprises at least 95%, 96%, 97%, 98% or 99% sequence identity to SEQ ID NO: 1, 9, 2 or 3.

In one aspect the wild type, functional WAP5.1 protein which is mutated to comprise one or more amino acids inserted, replaced or deleted in the LRR-domain is selected from the ClWAP5.1 of SEQ ID NO: 1 or of SEQ ID NO: 9, or a protein comprising at least 95% identity to SEQ ID NO: 1 or 9, the CsWAP5.1 of SEQ ID NO: 2 or a protein comprising at least 95% identity to SEQ ID NO: 2, and the CmWAP5.1 of SEQ ID NO: 3 or a protein comprising at least 95% identity to SEQ ID NO: 3, whereby all of the wild type proteins comprise an LRR-domain which is at least 95%, 96%, 97%, 98%, 99% or 100% identical to the LRR-domain of SEQ ID NO: 1, 9, 2 or 3.

In one aspect the wild type, functional WAP5.1 protein which is mutated to comprise one or more amino acids inserted, replaced or deleted in the LRR-domain is selected from ClWAP5.1 of SEQ ID NO: 1 or of SEQ ID NO: 9, or a protein comprising at least 95% identity to SEQ ID NO: 1 or 9, the CsWAP5.1 of SEQ ID NO: 2 or a protein comprising at least 95% identity to SEQ ID NO: 2, and the CmWAP5.1 of SEQ ID NO: 3 or a protein comprising at least 95% identity to SEQ ID NO: 3, whereby the sequence variation of 'at least 95%, 96%, or more', is due to sequence variation in the N-terminal part of the protein, i.e. preceding the F-box domain, while the remaining part of the protein (from start of the F-box domain to the end of the protein) is identical to the sequence of SEQ ID NO: 1, 9, 2 or 3.

A mutant protein comprising a frame shift leading to a change of one or more amino acids in the LRR-domain or a mutant protein comprising a truncation leading to the deletion of one or more amino acids of the LRR-domain is hereby encompassed as being a mutant protein comprising reduced function or no function in vivo.

Four specific mutants in the LRR-domain have been generated in watermelon, as shown in Table 1 and FIG. 4. In one aspect a watermelon, cucumber or melon plant comprising any of those four specific mutants in the LRR-domain of the ClWAP5.1, CsWAP5.1 or CmWAP5.1 protein, respectively, is encompassed herein.

In one aspect therefore a mutant ClWAP5.1 allele is provided encoding a mutant protein wherein the Q333 of SEQ ID NO: 1 or of SEQ ID NO: 9 (or a sequence comprising at least 95% identity to SEQ ID NO: 1 or 9) and/or the L528 of SEQ ID NO: 1 or of SEQ ID NO: 9 (or a sequence comprising at least 95% identity to SEQ ID NO: 1 or 9) and/or the P308 of SEQ ID NO: 1 or of SEQ ID NO: 9 (or a sequence comprising at least 95% identity to SEQ ID NO: 1 or 9), and/or the G330 of SEQ ID NO: 1 or of SEQ ID NO: 9 (or a sequence comprising at least 95% identity to SEQ ID NO: 1 or 9) is replaced by another amino acid or is deleted.

In one aspect a mutant CsWAP5.1 allele is provided encoding a mutant protein wherein the Q340 of SEQ ID NO: 2 (or a sequence comprising at least 95% identity to SEQ ID NO: 2) and/or the L535 of SEQ ID NO: 2 (or a sequence comprising at least 95% identity to SEQ ID NO: 2) and/or the P315 of SEQ ID NO: 2 (or a sequence comprising at least 95% identity to SEQ ID NO: 2), and/or the G337 of SEQ ID NO: 2 (or a sequence comprising at least 95% identity to SEQ ID NO: 2), is replaced by another amino acid or is deleted.

In one aspect a mutant CmWAP5.1 allele is provided encoding a mutant protein wherein the Q343 of SEQ ID NO: 3 (or a sequence comprising at least 95% identity to SEQ ID NO: 3) and/or the L538 of SEQ ID NO: 3 (or a sequence comprising at least 95% identity to SEQ ID NO: 3), and/or the P318 of SEQ ID NO: 3 (or a sequence comprising at least 95% identity to SEQ ID NO: 3), and/or the G340 of SEQ ID NO: 3 (or a sequence comprising at least 95% identity to SEQ ID NO: 3), is replaced by another amino acid or is deleted.

When referring to an amino acid being 'deleted', this includes a mutation whereby the codon is changed into a stop codon, or the codon is deleted, or a mutation whereby there is a frameshift, resulting in the amino acid not be encoded. Equally, when referring to an amino acid being 'replaced', this includes a mutation whereby the codon encodes a different amino acid, or a codon is inserted, or a mutation whereby there is a frameshift resulting in a different amino acid being encoded.

The plants and plant parts comprising at least one copy of a mutant wap5.1 allele may be plants of the family Cucurbitaceae, especially cultivated species such as cucumber (*Cucumis sativus*), melon (*Cucumis melo*) and watermelon (*Citrullus lanatus*). Also plants and plant parts of the family Cucurbitaceae, especially cucumber, melon and watermelon, comprising two copies of a mutant wap5.1 allele are encompassed herein, whereby diploid plants comprising two copies of the mutant wap5.1 allele results in plants exhibiting the phenotype of facultative parthenocarpy.

In one aspect the mutant wap5.1 allele is heterozygous in a diploid plant cell or plant, e.g. in a diploid watermelon, cucumber or melon plant. In another aspect the mutant wap5.1 allele is homozygous in a diploid plant cell or plant.

The plant cells and plants are preferably cultivated plants, such as elite breeding lines or varieties, and not wild plants. Cucumber may be any type of cucumber, such as long cucumber, pickling cucumber, slicing cucumber, etc. Likewise melon may be any type of melon (Galia, Piel de Sapo, Cantaloupe, honeydew, etc.) and watermelon may be any type of watermelon.

Watermelon plants, and parts thereof, which comprises at least one copy of the mutant wap5.1 allele, may be diploid, tetraploid or triploid. In another aspect it may be another polyploid, e.g. a pentaploid, hexaploid, heptaploid, octaploid, etc. A tetraploid plant comprising four copies of wap5.1 can for example be used to make an octaploid, by doubling the chromosomes. Crossing such an octoploid with a diploid homozygous for wap5.1 will result in a pentaploid comprising five copies of wap5.1. In one aspect the polyploidy watermelon plant comprises at least one copy of the mutant wap5.1 allele, but it may also comprise more copies, e.g. in a preferred aspect a triploid plant comprises two or three copies of a mutant wap5.1 allele or a tetraploid comprises two or four copies of a mutant wap5.1 allele.

A diploid plant may thus have the genotype wap5.1/WAP5.1 (heterozygous for the mutant allele) or wap5.1/wap5.1 (homozygous for the mutant allele). In one aspect the diploid plant comprising the wap5.1 allele in homozygous form is a double haploid plant (DH), e.g. a double haploid watermelon, cucumber or melon plant or plant cell or plant part. DH plants can be made by chromosome doubling (e.g. through colchicine treatment) of haploid cells.

A triploid watermelon plant may have the genotype wap5.1/WAP5.1/WAP5.1 or wap5.1/wap5.1/WAP5.1 or wap5.1/wap5.1/wap5.1. The triploid plant with genotype wap5.1/WAP5.1/WAP5.1 can be made by crossing a wild type female tetraploid (WAP5.1/WAP5.1/WAP5.1/WAP5.1) with a diploid male homozygous for the mutant allele (wap5.1/wap5.1). The triploid plant with genotype wap5.1/wap5.1/WAP5.1 can be made by crossing a female tetraploid (wap5.1/wap5.1/wap5.1/wap5.1) with a diploid male homozygous for the wild type allele (WAP5.1/WAP5.1).

A tetraploid watermelon plant may have the genotype wap5.1/WAP5.1/WAP5.1/WAP5.1 or wap5.1/wap5.1/WAP5.1/WAP5.1 or wap5.1/wap5.1/wap5.1/WAP5.1 or wap5.1/wap5.1/wap5.1/wap5.1. The genotypes wap5.1/wap5.1/WAP5.1/WAP5.1 can be made by doubling the chromosomes of a diploid wap5.1/WAP5.1. The genotypes wap5.1/wap5.1/wap5.1/wap5.1 can be made by doubling the chromosomes of a diploid wap5.1/wap5.1. The other two genotypes, wap5.1/WAP5.1/WAP5.1/WAP5.1 and wap5.1/wap5.1/wap5.1/WAP5.1 can for example be made by crossing two tetraploids of genotype wap5.1/w wap5.1/WAP5.1/WAP5.1 and identifying the genotypes in the progeny.

In one aspect the watermelon plant is homozygous for wap5.1, in another aspect it is heterozygous for wap5.1. In one aspect it is an inbred line or a variety. In a further aspect it is an F1 hybrid.

Seeds from which any of the watermelon plants, cucumber plants or melon plants described can be grown are also encompassed herein, as are parts of such a plant, such as seedless fruits produced in the absence of pollination, flowers, cells, roots, rootstocks, scions, leaves, stems, vegetative propagations, cuttings, seed propagations (e.g. selfings) and also in vitro cell- or tissue cultures, as well as pollen, ovaries, etc. are encompassed herein.

Diploid Watermelon, Cucumber and Melon Plants Comprising a Mutant wap5.1 Allele

In one aspect the watermelon plant or cucumber or melon plant is a diploid line (e.g. an inbred line) or variety, comprising at least one mutant copy of wap5.1, preferably two mutant copies (i.e. is homozygous for wap5.1). When preventing pollination of the female flowers, the diploid plant homozygous for wap5.1 will produce fruits which are seedless. When pollination does occur, the fruits will be seeded.

To prevent pollination one can, for example, grow the plant in an insect free environment. However, one can also produce a diploid plant which is male sterile. Thus, in one aspect of the invention a diploid plant is provided which is homozygous for wap5.1, and which additionally is male sterile. Male sterility is the failure of plants to produce functional anthers, pollen, or male gametes. Several male sterility genes have been identified in watermelon, including the ms-1 gene. The ms-1 nuclear gene controls male sterility and, in plants with an ms-1 gene in homozygous form (ms-1 is recessive), the normal development of anthers is hindered while female flower development is normal. The gene eliminates pollen production. Markers for the ms-1 gene and plants comprising the gene are described in EP2959771 and the database PINTO mentions that variety Bonta or Bonta F1 of *Seminis* is a plant according to this patent. The ms-1 gene has also been described in Zhang et al. 1996 (HortScience 31(1): 123-126). The ms-1 gene is on chromosome 6 of watermelon and can therefore easily be combined with wap5.1 on chromosome 5. In melon also male sterility genes exist. In cucumber the mutant wap5.1 allele can be combined with gynociousness, i.e. production of female, pistillate flowers.

Therefore, in one aspect the diploid plant and plant part according to the invention is male sterile and/or comprises a male sterility gene. If the male sterility gene is a recessive gene, the plant and plant part preferably comprises the gene in homozygous form. In one aspect the watermelon plant comprises the ms-1 gene, preferably in homozygous form. Thus, in one aspect the diploid watermelon plant comprises on chromosome 5 the mutant wap5.1 gene in homozygous form (wap5.1/wap5.1) and further comprises a male sterility gene, e.g. ms-1, in homozygous form, e.g. if the male sterility gene is recessive (e.g. ms-1/ms-1) or optionally in heterozygous form if the male sterility is dominant. One preferred plant is a diploid plant homozygous for wap5.1 and homozygous for ms-1.

A further way of ensuring that plants according to the invention, especially diploid watermelon plants, produce seedless fruits at all times (not only in the absence of pollination) is to combine the wap5.1 gene in homozygous form with a gene conferring stenospermocarpy, so that if pollination does occur the fruits will be seedless despite pollination. In one aspect the stenospermocarpy gene is the recessive gene called emb1. The wild type and mutant Emb1 gene has been described in co-pending application EP16171462.1. The Emb1 gene encodes a cyclin SDS like protein. When the mutant allele emb1 is in homozygous form, stenospermocarpy results. "Stenospermocarpy" means that induction of fruit set and development requires pollination but without the fruits producing mature or viable seeds. Mature or viable seeds are not developed in stenospermocarpic plants due to arrested seed development or degradation of ovules and/or embryos and/or endosperm or abortion of the ovules and/or embryos and/or endosperm before maturity is reached. Thus, when diploid plants homozygous for a mutant emb1 allele (emb1/emb1) are self-pollinated or pollinated by pollen from another plant, they produced seedless, diploid fruits.

Thus, in one aspect the diploid watermelon plant comprises on chromosome 5 the wap5.1 gene in homozygous form (wap5.1/wap5.1) and further comprises a stenospermocarpy gene, e.g. emb1, in homozygous form, e.g. if the stenospermocarpy gene is recessive (e.g. emb1/emb1) or optionally in heterozygous form if the stenospermocarpy gene is dominant. One preferred plant is a diploid plant homozygous for wap5.1 and homozygous for emb1.

One mutant allele of emb1 can be obtained from the watermelon seeds being heterozygous or homozygous for the mutant allele of the cyclin SDS like protein encoding gene (also referred to as Emb1 gene), deposited by Nunhems B.V. under NCIMB 42532. Of these seeds 25% contain the mutant allele (see mRNA of SEQ ID NO: 27) encoding a mutant protein of SEQ ID NO: 28. The wild type allele of the Emb1 gene can be obtained from the watermelon seeds being heterozygous or homozygous for the wild type cyclin SDS like protein encoding gene, deposited by Nunhems B.V. under NCIMB 42532. Of these seeds 25% contain the wild type allele of SEQ ID NO: 25 in homozygous form, encoding the wild type protein of SEQ ID NO: 26. Other mutant alleles of the Emb1 gene can be generated de novo, e.g. by mutagenesis or by other methods known to the skilled person. The genomic Emb1 nucleotide sequence shown under SEQ ID NO: 25 encodes a wild type cyclin SDS like protein of *Citrullus lanatus* having the amino acid sequence as shown under SEQ ID NO: 26. The mRNA sequence shown under SEQ ID NO: 27, and the mutant protein shown under SEQ ID NO: 28, is of the mutant emb1 allele found in seeds deposited under NCIMB42532.

A mutant allele of emb1 causes a plant to be male fertile but producing seedless fruits, when the plant is homozygous for the mutant allele. The mutation in the Emb1 gene can be any mutation, including deletions, truncations, insertions, point mutations, nonsense mutations, missense or non-synonymous mutations, splice-site mutations, frame shift mutations and/or mutations in regulatory sequences. Preferably the mutation is a point mutation and/or splice-site mutation. The mutation can occur in a DNA sequence comprising the coding sequence of a cyclin SDS like protein encoding gene (Emb1 gene) or in a RNA sequence encoding a cyclin SDS like protein or it can occur in the amino acid of a cyclin SDS like protein (or Emb1 protein). Concerning a DNA sequence of a cyclin SDS like protein encoding gene the mutation can occur in the coding sequence (cds, composed of the exons) or it can occur in non-coding sequences like 5'- and 3'-untranslated regions, introns, promoters, enhancers etc. of a cyclin SDS like protein encoding gene. In respect to RNA encoding a cyclin SDS like protein the mutation can occur in the pre-mRNA or the mRNA.

Diploid *Citrullus lanatus* seeds of plants segregating for a mutant allele of a cyclin SDS like protein encoding gene have been deposited by Nunhems B.V. under the Budapest Treaty under accession No. NCIMB 42532 at NCIMB Ltd., Ferguson Building, Craibstone Estate Bucksburn Aberdeen AB21 9YA, Scotland, UK on 27 Jan. 2016. For the seed deposit the allele of the cyclin SDS like protein encoding gene was designated emb1.

The deposited seeds were obtained from a self-pollinated back-cross of a plant homozygous for the emb1 mutant allele with plants homozygous for the emb1 wild type allele.

Therefore 25% of the deposited seeds are homozygous for the emb1 mutant allele and produce seedless fruits, 50% are heterozygous for the mutant allele and 25% are homozygous for the wild type allele, encoding the wild type cyclin SDS like protein.

In one aspect the invention, therefore, relates to a diploid watermelon plant or plant part comprising at least one copy of the mutant wap5.1 allele, preferably two copies, and at least one copy of a mutant emb1 allele, preferably two copies of a mutant emb1 allele. In one aspect the mutant emb1 allele is the allele found in seeds deposited under NCIMB 42532.

Seeds from which such a diploid plant can be grown are also encompassed herein, as are parts of such a plant, such as diploid seedless fruits, flowers, leaves, stems, vegetative propagations, cells, cuttings, seed propagations (e.g. selfings) and also in vitro cell- or tissue cultures, as well as pollen, ovaries, rootstocks, scions, etc. are encompassed herein. Thus, in one embodiment the diploid plant, or seeds from which the plant can be grown, or tissue or parts of the plant (pollen, anthers, ovules) comprises a mutant wap5.1 allele as described above in Table 1 or a different mutant wap5.1 allele.

Tetraploid Watermelon Plants Comprising a Mutant wap5.1 Allele

Seedless triploid watermelon production involves using pollen from diploid male parent plants to fertilize flowers of tetraploid maternal parent plants. Pollination of the tetraploid flowers with diploid pollen leads to F1 seeds which are triploid (Kihara, 1951, Proceedings of American Society for Horticultural Science 58: 217-230; Eigsti 1971, Hort Science 6: 1-2). The triploid hybrid plants, grown from these F1 seeds, are self-infertile as they produce sterile pollen due to chromosome imbalance. The triploid hybrids, therefore, normally need to be pollinated by a diploid pollenizer to produce watermelon fruit.

However, according to the present invention a triploid plant comprising one, two or three copies of a mutant wap5.1 gene produce fruits without pollination and there is no need anymore for a pollenizer plant being present. Therefore, a method for growing such triploid watermelon plants e.g. in a field, in the absence of pollenizer plants and/or in the absence of (fertile) pollen is encompassed herein, in order to produce seedless fruits.

In one aspect of the invention therefore both tetraploid plants, comprising preferably four copies of a recessive wap5.1 allele, for use as a female parent, and diploid plants comprising preferably two copies of a recessive wap5.1 allele, for use as a male parent, are provided, as well as triploid F1 hybrids (comprising preferably three copies of a mutant wap5.1 allele) produced by crossing the diploid male parent with the tetraploid female parent.

To make such a tetraploid plant, any of the diploid plants described above, which are preferably homozygous for wap5.1, may be used as starting material to generate tetraploid plants. Chromosome doubling techniques known to the skilled person may be used to generate a tetraploid plant from such diploid plants. For example Noh et al. (2012) Hort. Environ. Biotechnol. 53(6):521-529, evaluated different methods of generating tetraploid watermelons. In all methods an antimitotic agent is used, such as colchicine, dinitoalanine, or oryzalin, in order to induce chromosome doubling. Optionally tissue culture may be used to generate tetraploid plants from plant parts. To verify that plants are tetraploid chromosome number can be confirmed. Ploidy can be easily determined by chromosome counting or flow cytometry or other known methods (Sari et al. 1999, Scientia Horticulturae 82: 265-277, incorporated herein by reference).

Thus, in one aspect of the invention a tetraploid cultivated watermelon plant of the species *Citrullus lanatus* is provided, wherein said plant comprises two or preferably four copies of a mutant wap5.1 allele (as described above), one on each of the four chromosomes 5.

All embodiments described for the mutant wap5.1 allele above apply equally to the tetraploid. So for example the tetraploid plant may comprise four copies of a wap5.1 allele described in Table 1, or four copies of a different mutant wap5.1 allele as described further above.

Thus, in one aspect the invention encompasses a tetraploid watermelon plant or plant part comprising one, two, three or four copies of a mutant allele of a gene named WAP5.1 encoding a protein of SEQ ID NO: 1 or of SEQ ID NO: 9, or a protein comprising at least 95%, 96%, 97%, 98%, 99%, 99.5% or 99.9% sequence identity to SEQ ID NO: 1 or 9. The aspects regarding the mutant wap5.1 allele described above for diploid watermelon plants comprising one or two copies of a mutant wap5.1 allele apply to the tetraploid plants and plant parts. So, for example, in one aspect the mutant allele results in reduced expression or no expression of the WAP5.1 gene or the mutant allele encodes a mutant WAP5.1 protein having a decreased function or a loss-of-function.

In one aspect the tetraploid plant comprises two or preferably four copies of the mutant wap5.1 allele which encodes the mutant protein of SEQ ID NO: 4 or of SEQ ID NO: 10, comprising the L528F amino acid replacement in the LRR-domain.

Genotyping of tetraploid plants or plant parts (cells, leaves, DNA, etc.) can be done in the same way as for diploids, using for example a KASP-assay to distinguish SNP genotypes, e.g. plants or parts comprising TTTT for the marker mwm233348429 at nucleotide 61 of SEQ ID NO: 8 (detecting four mutant wap5.1 alleles encoding the protein of SEQ ID NO: 4 or of SEQ ID NO: 10, comprising the L528F mutation) can be distinguished from plants or parts comprising CTTT (detecting three mutant alleles encoding above) is provided. Preferably the watermelon plant is a tetraploid inbred female line, suitable as a parent for F1 hybrid seed production.

The generation of the tetraploid female inbred line can be carried out by using a diploid plant, comprising one or preferably two copies of the wap5.1 allele in order to double the chromosomes and generate a tetraploid plant. E.g. a diploid inbred line homozygous for wap5.1 can be used to generate the tetraploid plant.

A tetraploid plant comprising four copies of a mutant wap5.1 allele will express the phenotype, i.e. be facultative parthenocarpic.

Seeds from which such a tetraploid plant can be grown are also encompassed herein, as are parts of such a plant, such as tetraploid seedless fruits produced in the absence of pollination, flowers, leaves, stems, cuttings, vegetative propagations, cells, seed propagations (e.g. selfings) and also in vitro cell- or tissue cultures, as well as pollen, ovaries, rootstocks, scions, etc. are encompassed herein. Thus, in one embodiment the tetraploid plant, or seeds from which the plant can be grown, or tissue or parts of the plant (pollen, anthers, ovules) comprises a mutant wap5.1 allele as described above.

A tetraploid can comprise different mutant wap5.1 alleles, e.g. two mutant wap5.1 alleles encoding a truncated WAP5.1 protein and two mutant wap5.1 allele encoding a WAP5.1 protein having an amino acid substitution. Such plants can for example be made by first making a diploid comprising different mutant wap5.1 alleles and then doubling the chromosomes of such diploid. In one aspect the tetraploid does, however, comprise four copies of the same mutant wap5.1 allele, i.e. the tetraploid is made from a diploid which is homozygous for the wap5.1 allele.

Triploid Watermelon Plants Comprising a Mutant Wap5.1 Allele

In a further aspect triploid watermelon seeds, plants and plant parts comprising one, two or three copies of a mutant wap5.1 allele are provided, i.e. wap5.1/WAP5.1/WAP5.1 or wap5.1/wap5.1/WAP5.1 or wap5.1/wap5.1/wap5.1, respectively. Such triploids can be made as described above, and as shown in the Table 2 below:

TABLE 2

| | Female tetraploid parent | Male diploid parent | Genotype of F1 triploid seed produced by pollinating female tetraploid with pollen of male diploid |
|---|---|---|---|
| A | wap5.1/wap5.1/wap5.1/wap5.1 | wap5.1/wap5.1 | wap5.1/wap5.1/wap5.1 |
| B | wap5.1/wap5.1/wap5.1/wap5.1 | WAP5.1/WAP5.1 | wap5.1/wap5.1/WAP5.1 |
| C | WAP5.1/WAP5.1/WAP5.1/WAP5.1 | wap5.1/wap5.1 | WAP5.1/WAP5.1/wap5.1 | the protein of SEQ ID NO: 4 or of SEQ ID NO: 10), CCTT (detecting two mutant alleles encoding the protein of SEQ ID NO: 4 or of SEQ ID NO: 10), CCCT (detecting one mutant allele encoding the protein of SEQ ID NO 4 or of SEQ ID NO: 10) or CCCC (detecting four wild type alleles encoding the protein of SEQ ID NO: 1 or SEQ ID NO: 9) for the marker mwm233348429 at nucleotide 61 of SEQ ID NO: 8 in their genome. The same applies for other allele-specific markers.

In one aspect of the invention a tetraploid watermelon comprising at least one or two or three copies of the mutant wap5.1 allele (as described above), but preferably comprising four copies of the mutant wap5.1 allele (as described In one aspect a tetraploid plant comprising four copies of a mutant wap5.1 allele is used as female parent and is pollinated with pollen of diploid male parent comprising two copies of a mutant wap5.1 allele and the seeds from the cross are harvested. These seeds are triploid and they comprise three copies of a mutant wap5.1 allele of the invention (Table 2, row A). Plants grown from these seeds produce seedless watermelon fruits (triploid fruits) without the need for pollination to induce fruit set. The triploid hybrid plants, grown from these F1 triploid seeds, are self-infertile as they produce sterile pollen due to chromosome imbalance. These seeds can, thus, be grown in production fields without the need for pollenizer plants. This is the first time that seedless triploid watermelon fruits can be produced in the absence of pollen and pollenizer plants.

In one aspect the triploid under A above comprises three identical mutant wap5.1 alleles, i.e. the female and male parents comprise the same mutant allele. However, in another aspect the female parent and the male parent may comprise different mutant wap5.1 alleles. For example the female parent may comprise four mutant wap5.1 allele encoding a truncated WAP5.1 protein and the male parent may comprise two mutant wap5.1 allele encoding a WAP5.1 protein having an amino acid substitution, e.g. Leucine 528 of SEQ ID NO: 1 or 9 (or a sequence comprising at least 95% identity to either of these) being replaced by Phenylalanine (mutant L528F), or the other way around.

In one aspect the mutant wap5.1 allele conferring facultative parthenocarpy described herein is combined with another mutant allele conferring parthenocarpy, especially conferring facultative parthenocarpy. Such another mutant allele is for example the wop1 allele described in WO2018/060444, which is located on chromosome 4 (it is also referred to as wap4.1). In one aspect a mutant wap5.1 allele is combined with a mutant wop1 allele in diploid, triploid or tetraploid watermelon plants. As wop1 is on a different chromosome, one can make different combinations between wop1 and wap5.1, e.g. three mutant copies of each of wop1 and of wap5.1 in a triploid watermelon, or one or two mutant copy of wop1 and three mutant copies of wap5.1 in a triploid watermelon, or the other way around, etc.

The triploid, seedless fruits are preferably marketable. Preferably they have an average brix of at least 6.0, 7.0, 8.0 or preferably at least 9.0, preferably at least 10.0, more preferably at least 11.0. Fruits may be of any size, shape, color and rind pattern. Preferably fruit flesh color at maturity is uniform. In one aspect fruit flesh is red or dark red.

The average fruit weight of a triploid hybrid comprising wap5.1 in three copies may be equal to or above 2, 3, 4, 5, 6, 7, 8, 9, 10, 11, 12, 13 or 14 kg. In another embodiment average fruit weight of a triploid hybrid comprising wap5.1 in three copies may be equal to or less than 5 kg, e.g. 4, 3, 2, 1.5 or 1 kg or even less.

Seedless fruits may be of any shape (e.g. elongate, oval, blocky, spherical or round), fruit surface (furrow, smooth), flesh color (red, dark red, scarlet red, coral red, orange, salmon, pink, pinkish red, yellow, canary yellow or white), rind color (e.g. light green; dark green; green-striped with narrow, medium or wide stripes; grey types; with or without spotting; Golden yellow), rind thickness, rind toughness, rind pattern (e.g. striped, non-striped, netted), flesh structure/flesh firmness, lycopene and/or vitamin content, different sugar to acid ratios, fruit flavour, etc.

Thus, the mutant wap5.1 allele may be used to breed a range of seedless varieties, producing fruits of different shapes and sizes, etc. by traditional breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar:acid ratio, good flavor, high vitamin and lycopene content, firm flesh texture, non-fibrous flesh texture, freedom from defects such as hollow heart, rind necrosis, blossom-end rot or cross stitch and good rind characteristics and cracking-resistance).

Seeds from which such triploid F1 hybrid plants can be grown are one aspect of the invention. Thus, in one aspect a method for growing triploid watermelon plants/producing seedless watermelon fruits comprising the steps: seeding or planting triploid watermelon plants comprising one, two or three mutant wap5.1 alleles in their genome, optionally preventing pollination of the flowers (e.g. by male sterility, absence of pollenizers and/or absence of pollen) and harvesting the seedless watermelon fruits which develop in the absence of pollination through parthenocarpy. In principle, preventing pollination is not needed, as triploid fruits anyway produce seedless fruits. The difference is that triploids comprising the mutant wap5.1 allele(s) do not need pollen anymore to induce fruit development, so the cultivation area can be occupied entirely by triploid plants and interplanting of pollenizer plants is not needed anymore.

Also for diploid watermelon plants comprising two copies of a mutant wap5.1 allele a method of producing seedless fruits is provided. Thus, in one aspect a method for growing diploid watermelon plants/producing seedless watermelon fruits comprising the steps: seeding or planting diploid watermelon plants comprising two copies of a mutant wap5.1 allele in their genome, preventing pollination of the flowers (e.g. by male sterility, absence of pollenizers and/or absence of pollen) and harvesting the seedless watermelon fruits which develop in the absence of pollination through parthenocarpy. For diploid cultivation it is necessary to prevent pollination of the female flowers, as the fruits will otherwise contain seeds. Pollination can be prevented by various means or combinations thereof, e.g. growing the plants in protected, pollen free environments, ensuring that the plants are male sterile and/or do not produce pollen, generating a time difference in pollen production and opening of female flowers, removing male flowers, etc.

Regarding triploid seeds and triploid plants comprising only one or two copies of a mutant wap5.1 allele of the invention (as shown in the Table 2 above, row B and C), the phenotype has not yet been tested, but these may also be suitable to produce seedless fruits without pollen and they may also be grown in a field without pollenizer plants. In any case, such triploid plants and seeds from which such plants can be grown are an aspect of the invention, as are parts thereof and triploid fruits produced by such plants. Preferably such triploid fruits are marketable. Preferably they have an average brix of at least 6.0, 7.0, 8.0 or preferably at least 9.0, preferably at least 10.0, more preferably at least 11.0. Fruits may be of any size, shape, color and rind pattern. Preferably fruit flesh color at maturity is uniform. In one aspect fruit flesh is red or dark red.

In one aspect the triploid plant of the invention is a vegetative propagation.

Also provided is a method for producing triploid hybrid watermelon seeds, wherein triploid plants grown from such seeds produce fruits in the absence of pollination, said method comprising:

(a) providing a facultative parthenocarpic diploid watermelon plant and a facultative parthenocarpic tetraploid plant (see e.g. Table 2 row A), (b) allowing pollination of pistillate flowers of the tetraploid plant with pollen of the diploid plant, and (c) harvesting seeds produced in the fruits of the tetraploid plant, and optionally (d) drying the harvested seeds.

Optionally the dried and harvested F1 seeds are then packaged. They may also be treated prior to packaging. Thus, packages or containers comprising or consisting of seeds obtained by the above method are an embodiment herein.

Also provided is a method for producing triploid hybrid watermelon seeds, said method comprising:

(a) providing a diploid watermelon plant lacking a mutant wap5.1 allele and a tetraploid plant comprising four copies of a mutant wap5.1 allele (see e.g. Table 2 row B), or providing a diploid watermelon plant homozygous for the mutant wap5.1 allele and a tetraploid plant lacking a mutant wap5.1 allele (e.g. Table 2 row C), (b) allowing pollination of pistillate flowers of the tetraploid plant with pollen of the diploid plant, and (c) harvesting seeds produced in the fruits of the tetraploid plant, and optionally (d) drying the harvested seeds.

Optionally the dried and harvested F1 seeds are then packaged. They may also be treated prior to packaging. Thus, packages or containers comprising or consisting of seeds obtained by the above method are an embodiment herein.

Seeds from which any the above triploid plants can be grown are also encompassed herein, as are parts of such a plant, such as triploid fruits, flowers, leaves, stems, cuttings, vegetative propagations, cells, seed propagations (e.g. selfings) and also in vitro cell- or tissue cultures, as well as pollen, ovaries, rootstocks, scions, etc. are encompassed herein. Thus, in one embodiment the triploid plant, or seeds from which the plant can be grown, or tissue or parts of the plant (pollen, anthers, ovules) comprises a mutant wap5.1 allele as described above.

A method for growing the triploid plants comprising at least one copy of a mutant wap5.1 allele is also provided. The triploid plants are changed from stenospermocarpic to parthenocarpic, i.e. no pollenizer plant is needed anymore to induce fruit development from the flowers, and these plants can therefore be grown in the absence of pollenizer plants, producing seedless fruits. Thus, an entire field or greenhouse can be grown with only triploid plants, increasing the yield of seedless, triploid fruits. The seedless fruits, comprising at least one copy (or two or three copies) of the mutant wap5.1 allele in their genome are also encompassed herein, as are food or feed products comprising fruits or fruit parts.

The method thus comprises: seeding or growing triploid watermelons plants comprising at least one copy of a mutant wap5.1 allele in a cultivation area, such as a field or greenhouse or tunnel, without the presence of pollenizer plants (e.g. without interplanting pollenizer plants), and allowing fruits to develop without pollination of the flowers (parthenocarpic), and optionally harvesting the seedless triploid fruits.

Vegetative Propagations and Cell or Tissue Cultures

The above diploid plants, tetraploid plants or triploid plants (or other polyploids) can also be reproduced vegetatively (clonally) and such vegetatively propagated plants, or 'vegetative propagations' are an embodiment of the invention. They can easily be distinguished from other watermelon, cucumber or melon plants by the presence of a mutant wap5.1 allele and/or phenotypically. The presence of one or more mutant wap5.1 alleles can be determined as described elsewhere herein.

Vegetative propagations can be made by different methods. For example one or more scions of a plant of the invention may be grafted onto a different rootstock, e.g. a biotic or abiotic stress tolerant rootstock.

Other methods include in vitro cell or tissue culture methods and regeneration of vegetative propagations from such cultures. Such cell or tissue cultures comprise or consist of various cells or tissues of a plant of the invention. In one aspect such a cell or tissue culture comprises or consists of vegetative cells or vegetative tissues of a plant of the invention.

In another aspect a cell or tissue culture comprises or consists of reproductive cells or tissues, such as anthers or ovules of a plant of the invention. Such cultures can be treated with chromosome doubling agents to make e.g. double haploid plants, or they can alternatively be used to make haploid plants (e.g. to make diploids from a tetraploid or to make haploids from a diploid).

An in vitro cell or tissue culture may, thus, comprise or consist of cells or protoplasts or plant tissue from a plant part selected from the group consisting of: fruit, embryo, meristem, cotyledon, pollen, ovule, leaf, anther, root, root tip, pistil, flower, seed, stem. Also parts of any of these are included, such as e.g. only the seed coat (maternal tissue).

Thus, in one aspect of the invention a cell culture or a tissue culture of cells of a plant comprising one, two, three or four copies of a mutant wap5.1 allele, all as described above, is provided. As mentioned, a cell culture or a tissue culture comprises cells or protoplasts or plant tissue from a plant part of a plant comprising a mutant wap5.1 allele may comprise or consist of cells or tissues selected from the group consisting of: embryo, meristem, cotyledon, pollen, leaf, anther, root, root tip, pistil, flower, seed, stem; or parts of any of these.

Also provided is a watermelon, cucumber or melon plant regenerated from such a cell culture or tissue culture, wherein the regenerated plant (or progeny thereof, e.g. obtained after selfing the regenerated plant) comprises the mutant wap5.1 allele. Therefore, in one aspect the watermelon, cucumber or melon plant comprising a mutant wap5.1 allele in one or more copies is a vegetatively propagated watermelon, cucumber or melon plant.

In a different aspect the cells and tissues of the invention (and optionally also the cell or tissue culture), comprising wap5.1 in one or more copies, are non-propagating cells or tissues.

Methods

A method for seedless triploid watermelon fruit production is provided, said method comprising:

1. providing a triploid hybrid (F1) watermelon plant or seed comprising at least one, preferably two or preferably three copies of a mutant wap5.1 allele, 2. planting or seeding said triploid hybrid plants in a field, preferably without planting or seeding diploid pollenizer plants in the same field, and optionally 3. harvesting the seedless watermelon fruits produced on the triploid plants, whereby the fruits are preferably produced without pollination of the female flowers.

In one aspect the triploid hybrid plant of step 1 is preferably not grafted onto a different rootstock. In another aspect it may be grafted onto a different rootstock.

As mentioned, there is no need anymore to provide diploid pollenizer plants to induce fruit set on of the female flowers of the triploid plants. This means that an entire field can be sown or transplanted with essentially only seeds or transplants of the F1 triploid seeds or plants. Yield of seedless watermelon fruits per hectare is therefore greatly enhanced. Also seeding and planting is made much easier as only one genotype is seeded or planted.

Thus, the method can also be described as a method of producing seedless watermelon fruits, said method comprising growing a triploid plant comprising at least one, preferably two, more preferably three copies of mutant wap5.1 allele and harvesting the fruits produced by said plants. The fruits develop preferably without pollination of the female flowers, i.e. in the absence of viable or fertile pollen. No insects, such as bees, are required anymore for fruit set, i.e. placing bee hives into or near the fields is not necessary.

The harvested triploid, seedless fruits may be packaged for fresh markets or for processing. Fruits comprising one, two or three wap5.1 alleles obtainable by the above method are encompassed herein. Optionally detection of the mutant wap5.1 allele e.g. by detection of the mutant wap5.1 allele using DNA, RNA or protein detection as described elsewhere, e.g. by PCR, genotyping or marker analysis of markers linked to (or closely linked to) the wap5.1 allele or being allele-specific (e.g. detecting the mutation which distinguishes the mutant allele from the wild type allele), can distinguish such fruits. Thus, in one embodiment, harvested triploid fruits (i.e. wap5.1/WAP5.1/WAP5.1 or wap5.1/wap5.1/WAP5.1 or wap5.1/wap5.1/wap5.1) are provided, such as packaged whole fruits or fruit parts and/or processed fruits or fruit parts.

Also provided is a method for production of a facultative parthenocarpic cultivated watermelon plant comprising the steps of a) introducing mutations in a population of watermelon plants or providing a mutant population of watermelon plants;

b) selecting a plant producing seedless fruits without pollination of the female flowers and producing a seeded fruit after pollination of the female flowers and/or selecting a plant comprising a mutant allele of the WAP5.1 gene;

c) optionally verifying if the plant selected under b) comprises a mutant allele of a WAP5.1 gene; and d) optionally growing the plants obtained under c).

A watermelon plant produced by the above method is encompassed.

The population of watermelon plants under a) is preferably a single genotype of a cultivated watermelon breeding line or variety, which is treated/has been treated with (or subjected to) a mutagenic agent, or progeny of such a population e.g. obtained after selfing individuals of the population to produce M2, M3 or further generation plants. This may for example be a TILLING population.

In step b) plants are screened for the phenotype, i.e. for being facultative parthenocarpic and/or the plants (or plant parts or DNA therefrom) are screened for the presence of a mutant allele of the WAP5.1 gene, i.e. an allele which either has reduced expression or no expression of the wild type WAP5.1 protein or an allele encoding a mutant WAP5.1 protein. Regarding the screening for the phenotype, it is understood that without pollination of the female flowers, seedless fruits should develop; with pollination of the female flowers seeded fruits should develop. This phenotypic screening can be done in several steps. For example first plants can be grown in an insect free environment and male flowers can be removed. Female flowers can be observed visually for flowering and fruit development (in absence of pollen). The developed fruit can be cut in half at maturity to check if these are seedless. Selected plants can e.g. be vegetatively reproduced to confirm the parthenocarpy phenotype and/or to e.g. hand-pollinate flowers to see if fruits are seeded upon pollination (facultative parthenocarpy). Regarding the screening of the plants for the presence of a mutant allele of the WAP5.1 gene, this can be done by various methods which detect wap5.1 DNA, RNA or protein, for example by e.g. designing PCR primers which amplify part of the coding region or all of the coding region to amplify the genomic DNA in order to determine if a plant comprises a mutation in the genomic DNA, or other methods.

Step c) can involve various methods to determine whether a mutant wap5.1 allele is present. For example marker analysis or sequence analysis of the chromosome region comprising the WAP5.1 locus can be carried out, or PCR or RT-PCR can be used to amplify the wap5.1 allele (or a part thereof) or the mRNA (cDNA). Also genetic analysis to determine the recessive inheritance may be carried out.

Also the use of a facultative parthenocarpic watermelon plant for producing seedless watermelon fruits is provided, preferably without pollination of the female flowers of the plant. Further the use of a mutant wap5.1 allele for generating facultative parthenocarpic watermelon plants and/or seedless watermelon fruits in the absence of pollination of the female flowers is provided. Likewise the use of a mutant wap5.1 allele of a WAP5.1 gene according to the invention for producing facultative parthenocarpic watermelon plants is encompassed herein.

In one aspect the plants, plant parts and plant cells according to the invention are not exclusively obtained by means of an essentially biological process as defined by Rule 28 (2) EPC (European Patent Convention).

In one aspect the plants are non-GMO (not genetically modified).

In one aspect the mutant alleles are generated by mutagenesis (e.g. chemical or radiation mutagenesis) or by targeted mutagenesis, especially using the CRISPR system (e.g. Crispr/Cas9 or Crispr/Cpf1 or other nucleases). In one aspect the cultivated plant comprising the mutant wap5.1 allele is not a transgenic plant, e.g. non transgenic progeny are selected which do not comprise e.g. the CRISPR construct.

In one aspect the mutant allele of the WAP5.1 gene comprises a human induced mutation, i.e. a mutation introduced by mutagenesis techniques, such as chemical mutagenesis or radiation mutagenesis, or targeted mutagenesis techniques, such as Crispr based techniques.

A method for targeted mutagenesis of the endogenous WAP5.1 gene in watermelon, melon and cucumber is provided herein, using any targeted gene modification method, such as CRISPR based methods (e.g. Crispr/Cas9 or Crispr/Cpf1), TALENS, Zinc Fingers or other methods.

In one aspect an isolated mutant WAP5.1 protein and an isolated wild type WAP5.1 protein is provided or an isolated nucleic acid molecule encoding a mutant WAP5.1 protein or a wild type WAP5.1 protein. Also an antibody able to bind a mutant or wild type WAP5.1 protein is encompassed herein.

Detection Methods

In one aspect a screening method for identifying and/or selecting seeds, plants or plant parts or DNA from such seeds, plants or plant parts comprising in their genome a mutant allele of a WAP5.1 protein-encoding gene is provided.

The method comprises screening at the DNA, RNA (or cDNA) or protein level using known methods, in order to detect the presence of the mutant allele. There are many methods to detect the presence of a mutant allele of a gene.

Thus, a method for screening and/or selecting plants or plant material or plant parts, or DNA or RNA or protein derived therefrom, for the presence of a mutant wap5.1 allele is provided comprising one or more of the following steps:

a) determining if the gene expression of the endogenous WAP5.1 gene is reduced or abolished;

b) determining if the amount of wild type WAP5.1 protein is reduced or abolished;

c) determining if a mutant mRNA, cDNA or genomic DNA encoding a mutant WAP5.1 protein is present;

d) determining if a mutant WAP5.1 protein is present;

e) determining if plants or progeny thereof are facultative parthenocarpic.

Routine methods can be used, such as RT-PCR, PCR, antibody based assays, sequencing, genotyping assays (e.g. allele-specific genotyping), phenotyping, etc.

The plants or plant material or plant parts may be watermelon, cucumber or melon plants or plant materials or plant parts, such as leaves, leaf parts, cells, fruits, fruit parts, ovaries, stem, hypocotyl, seed, parts of seeds, seed coat, embryo, etc.

For example if there is a single nucleotide difference (single nucleotide polymorphism, SNP) between the wild type and the mutant allele, a SNP genotyping assay can be used to detect whether a plant or plant part or cell comprises the wild type nucleotide or the mutant nucleotide in its genome. For example the SNP can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p097-1098 for KASP-assay method.

Equally other genotyping assays can be used. For example, a TAQMAN® SNP genotyping assay, a High Resolution Melting (HRM) assay, SNP-genotyping arrays (e.g. Fluidigm, Illumina, etc.) or DNA sequencing may equally be used.

In one aspect for example the SNP marker mwm23348429 at nucleotide 61 of SEQ ID NO: 8, or at nucleotide 61 of a sequence comprising at least 92%, 93%, 94%, 95%, 96%, 97%, 98%, 99% or more sequence identity to SEQ ID NO: 8, can be used to detect the presence or absence of a mutant wap5.1 allele encoding a mutant protein comprising a L528F amino acid substitution in watermelon, a L535F amino acid substitution in cucumber or a L538F amino acid substitution in melon. Based on the difference between the genomic sequence of the wild type allele and the mutant allele, the skilled person can easily develop markers which can be used to detect specific alleles.

Also provided herein is a method for identifying a watermelon, cucumber or melon plant (or plant part) comprising a mutant wap5.1 allele, the method comprising detecting in the plant (or plant part) the presence of a mutant wap5.1 allele, wherein the presence is detected by at least one marker within the wap5.1 allele or by detecting the protein encoded by the wap5.1 allele. The method for detecting the mutant wap5.1 allele is selected from the group consisting of PCR amplification, nucleic acid sequencing, nucleic acid hybridization and an antibody based assay (e.g. immunoassay) for detecting the wap5.1 protein encoded by the allele.

Also provided herein is a method for identifying a watermelon, cucumber or melon plant (or plant part) comprising a mutant wap5.1 allele comprising a mutation in a regulatory element, the method comprising detecting in the plant (or plant part) the reduced gene expression or absence of gene expression of the mutant wap5.1 allele, wherein the presence is detected by mRNA levels (cDNA) of the wild type WAP5.1 allele or by detecting the protein levels of the wild type WAP5.1 protein. The method for detecting the mutant wap5.1 allele is selected from the group consisting of PCR amplification (e.g. RT-PCR), nucleic acid sequencing, western blotting and an antibody based assay (e.g. immunoassay) for detecting the WAP5.1 protein encoded by the allele.

Also provided is a method for determining, or detecting or assaying, whether a cell or of a watermelon plant or plant part comprises a mutant allele of a gene named WAP5.1 encoding a protein of SEQ ID NO: 1 or 9, or a protein comprising at least 95%, 96%, 97% or 98% sequence identity to SEQ ID NO: 1 or 9, is provided herein. In one aspect the method comprises determining the expression of the allele, and/or determining the coding sequence of the allele and/or determining part of the coding sequence of the allele (e.g. a SNP genotype of the allele), and/or determining the amino acid sequence of the protein produced and/or the amount of protein produced. The same applies to a method for determining, or detecting or assaying, whether a cell or of a cucumber or melon plant or plant part comprises a mutant allele of a gene named WAP5.1 encoding a protein of SEQ ID NO: 2, or a protein comprising at least 95%, 96%, 97% or 98% sequence identity to SEQ ID NO: 2 (cucumber), or a protein of SEQ ID NO: 3, or a protein comprising at least 95%, 96%, 97% or 98% sequence identity to SEQ ID NO: 3 (melon).

Various method can be used to determine whether a plant or part thereof comprises a mutant wap5.1 allele of the invention. As mentioned, the mRNA (or cDNA) level of the wild type allele may be determined, or the wild type protein level may be determined, to see if there is a reduced expression or no expression of the wild type allele. Also, the coding sequence or part thereof may be analysed, for example if one already knows which mutant allele may be present, an assay can be developed to detect the mutation, e.g. a SNP genotyping assay can e.g. distinguish between the presence of the mutant allele and the wild type allele, e.g. genotyping for marker mwm23348429.

A method for selection of a plant or seed comprising the steps of:

a) identifying a plant or seed which has a mutation in an allele of a gene encoding a WAP5.1 protein, wherein the wild type allele of the gene encodes a WAP5.1 protein comprising at least 95%, 96%, 97%, 98%, 99%, 99.5% or 99.9% sequence identity to any one of the proteins selected from the group of: SEQ ID NO:1 or SEQ ID NO:1 or SEQ ID NO: 2 or SEQ ID NO: 3, and optionally b) determining whether the plant, or a progeny plant produced by self-fertilization, is facultative parthenocarpic, and optionally c) selecting a plant or seed comprising at least on copy of the mutant allele of step a).

A method for production of a plant, preferably a watermelon, melon or cucumber plant, comprising the steps of:

a) introducing mutations in a population of plants or seeds, b) selecting a plant producing seedless fruit in the absence of pollination and seeded fruits after pollination and/or selecting a plant or seed comprising a mutant wap5.1 allele in its genome, c) optionally verifying if the plant selected under b) has a mutation in an allele encoding a WAP5.1 protein, and optionally d) growing or cultivating the plant or seed obtained under c), wherein the wild type allele of the gene encodes a WAP5.1 protein comprising at least 95% sequence identity to any one of the proteins selected from the group of: SEQ ID NO:1 or SEQ ID NO:9 or SEQ ID NO: 2 or SEQ ID NO: 3.

A method for production of a plant comprising the steps of:

a) introduction of a foreign nucleic acid molecule into a plant, wherein the foreign nucleic acid molecule is chosen from the group consisting of:

i) DNA molecules, which code at least one antisense RNA, which effects a reduction in the expression of an endogenous gene encoding a WAP5.1 protein;

ii) DNA molecules, which by means of a co-suppression effect lead to the reduction in the expression of an endogenous gene encoding a WAP5.1 protein;

iii) DNA molecules, which code at least one ribozyme, which splits specific transcripts of an endogenous gene encoding a WAP5.1 protein;

iv) DNA molecules, which simultaneously code at least one antisense RNA and at least one sense RNA, wherein the said antisense RNA and the said sense RNA form a double-stranded RNA molecule, which effects a reduction in the expression of an endogenous gene encoding a WAP5.1 protein (RNAi technology);

v) nucleic acid molecules introduced by means of in vivo mutagenesis, which lead to a mutation or an insertion of a heterologous sequence in an endogenous gene encoding a WAP5.1 protein, wherein the mutation or insertion effects a reduction in the expression of a gene encoding a WAP5.1 protein or results in the synthesis of a loss-of-function or reduced function WAP5.1 protein;

vi) nucleic acid molecules, which code an antibody, wherein the antibody results in a reduction in the activity of an endogenous gene encoding a WAP5.1 protein due to the bonding of the antibody to an endogenous WAP5.1 protein;

vii) DNA molecules, which contain transposons, wherein the integration of these transposons leads to a mutation or an insertion in an endogenous gene encoding a WAP5.1 protein, which effects a reduction in the expression of an endogenous gene encoding a WAP5.1 protein, or results in the synthesis of an inactive protein;

viii) T-DNA molecules, which, due to insertion in an endogenous gene encoding a WAP5.1 protein, effect a reduction in the expression of an endogenous gene encoding a WAP5.1 protein, or result in the synthesis of a loss-of-function or reduced function WAP5.1 protein;

ix) nucleic acid molecules encoding rare-cleaving endonucleases or custom-tailored rare-cleaving endonucleases preferably a meganuclease, a TALENs or a CRISPR/Cas system.

b) selecting a plant wherein the plant, or a progeny of the plant produced by self-fertilization, produces seedless fruit in the absence of pollination and seeded fruits after pollination, optionally c) verifying if the plant selected under b) has a decreased activity of a WAP5.1 protein compared to wild type plants into whose genome e.g. no foreign nucleic acid molecules had been integrated, optionally d) growing/cultivating the plants obtained under c).

A plant obtained by any of the methods above is encompassed herein.

In one aspect a genetically modified plant and plant part is provided, whereby the plant has reduced expression or no expression of the endogenous WAP5.1 gene, e.g. through silencing of the endogenous WAP5.1 gene. Such a plant may be any plant, in one aspect it is a watermelon, melon or cucumber. However, it can also be a maize, soybean, wheat, canola, tomato, cotton, etc.

In another aspect a plant and plant part is provided comprising a mutation in the endogenous WAP5.1 gene, e.g. an induced mutation generated e.g. by targeted mutagenesis, whereby either the gene expression is reduced or abolished or the expressed gene encodes a reduced function or loss of function WAP5.1 protein compared to the wild type protein. Such a plant may be any plant, in one aspect it is a watermelon, melon or cucumber, as described. However, it can also be a maize, soybean, wheat, canola, tomato, cotton, pepper, etc. As the WAP5.1 gene in other species may have less sequence identity to the Cucurbitaceae WAP5.1 gene, it is encompassed herein that in this aspect of the invention the WAP5.1 gene is a gene encoding a protein comprising at least 60%, 65%, 70%, 75%, 80%, 85%, 90%, 95% sequence identity to SEQ ID NO: 1, 9, 2 or 3. Optionally the WAP5.1 gene is a gene encoding a protein comprising at least 60%, 65%, 70%, 75%, 80%, 85%, 90%, 95% sequence identity to SEQ ID NO: 1, 9, 2 or 3, whereby the protein comprises the conserved F-box domain and/or LRR-domain of SEQ ID NO: 1, 9, 2, or 3 or a F-box or LRR-domain comprising at least 70%, 75%, 80%, 85%, 90%, 95% sequence identity to the F-box or LRR-domain of SEQ ID NO: 1, 9, 2 or 3. The skilled person can identify orthologs of the WAP5.1 gene in such other species, e.g. in pepper or tomato, and thereby make facultative parthenocarpic pepper or tomato plants. All embodiments described herein for watermelon, cucumber and melon apply equally for other crop species, with the difference that the WAP5.1 gene may thus encode a protein with less than 95% sequence identity to the wild type WAP5.1 watermelon, cucumber or melon protein of SEQ ID NO: 1, 9, 2 or 3, respectively.

Also provided herein is a method for screening watermelon plants, seeds, plant parts, or DNA therefrom, for the presence of a mutant allele of a gene named WAP5.1, or for selecting a watermelon plant, seed or plant part comprising a mutant allele of a gene named WAP5.1, comprising the steps:

a) analysing whether the genomic DNA comprises a wild type WAP5.1 allele which encodes a protein of SEQ ID NO: 1 or 9 and/or a mutant WAP5.1 allele which encodes a mutant protein comprising one or more amino acids replaced, inserted or deleted compared to the wild type WAP5.1 protein, and optionally b) selecting a plant, seed or plant part comprising two copies of the wild type allele, two copies of the mutant allele or one copy of the wild type allele and one copy of the mutant allele.

In one aspect the method step a) comprises a method selected from:

i) amplification of at least part of the WAP5.1 allele using one or more oligonucleotide primers which hybridize to the DNA of the WAP5.1 allele, ii) hybridization of one or more oligonucleotide probes to at least part of the DNA of the WAP5.1 allele, iii) sequencing the DNA, mRNA or cDNA of the WAP5.1 allele.

So, for example a DNA sample can be obtained from a plant, seed or plant part, and a PCR reaction can be carried out to amplify part of the wild type WAP5.1 allele and/or part of the mutant WAP5.1 allele. Competitive PCR methods, for example, can be used (such as a KASP assay) to generate amplification products of the alleles present at the WAP5.1 locus in the genomic DNA. Similarly, oligonucleotide probes can generate hybridization products of the alleles present at the WAP5.1 locus in the genomic DNA. Primers or probes may be designed to be specific to a particular WAP5.1 allele, e.g. to differentiate between the wild type allele and a mutant allele. For example, SNP marker mwm23348429 comprises a SNP at nucleotide 61, which differentiates between the wild type allele encoding a protein comprising amino acid L528 and the mutant allele encoding a protein comprising amino acid F528 in SEQ ID NO: 1 or 9. Primers or probes can be designed to detect this SNP and the same can be done for any other polymorphism (e.g. SNP or INDEL) found between wild type and mutant WAP5.1 alleles, such as those of Table 1.

In one aspect, a genotyping assay is provided for genotyping watermelon plants, seeds, plant parts, cells or tissues, comprising the steps:

a) providing genomic DNA of one or more watermelon plants or a population of plants, and b) carrying out a genotyping assay which detects the presence of the wild type allele encoding the protein of SEQ ID NO: 1 or 9 and/or the presence of a mutant allele, wherein the mutant allele encodes a mutant protein which comprises one or more amino acids inserted, deleted or replaced with respect of SEQ ID NO: 1 or 9, and optionally c) selecting a plant, seed, plant part, cell or tissue comprising either two copies of the wild type allele, or one copy of the wild type allele and one copy of a mutant allele, or two copies of a mutant allele.

In step b) the mutation in the mutant allele preferably causes one or more amino acids to be inserted, deleted or replaced with respect to the wild type protein, e.g. the mutant allele encodes one of the mutant WAP5.1 proteins described herein e.g. in Table 1.

The wild type alleles are for example the genomic DNA at the locus on chromosome 5, corresponding to the Charleston Grey locus in the region described, or the variety 97103 locus in the region described earlier. These WAP5.1 loci comprise the genomic sequence of SEQ ID NO: 7 and SEQ ID NO: 14, respectively. Both have a sequence identity of 99.8% when aligned pairwise using the program Needle. The cDNA encoded by the wild type loci is the cDNA of SEQ ID NO: 6 (encoding the wild type protein of SEQ ID NO: 1) and the cDNA of SEQ ID NO: 11 (encoding the wild type protein of SEQ ID NO: 9), respectively.

Step a) may comprise isolation of genomic DNA from the plant, seeds, plant part, cell or tissue to be analyzed in the genotyping assay. Often crude DNA extractions methods can be used, as known in the art.

Step b) preferably comprises a bi-allelic genotyping assay, which makes use of allele-specific oligonucleotide primers and/or allele-specific probes, i.e. primers or probes which discriminate between the wild type allele and the mutant allele.

The plants of step a) may be mutagenized using e.g. chemical or radiation mutagens or gene editing techniques. Thus prior to step a) there may be a step of treating the plants, seeds or plant parts with a mutagenic agent or induce targeted mutations in the WAP5.1 allele.

Various genotyping assays can be used, as long as they can detect INDELs and SNPs and can differentiate between the wild type allele being present in the genomic DNA (at the WAP5.1 locus on chromosome 5) or a mutant allele of the WAP5.1 gene being present in the genomic DNA. Genotyping assays are generally based on allele-specific primers used in PCR or thermal cycling reactions (polymerase chain reaction) to amplify either the wild type or mutant allele and detect the amplification product or on allele-specific oligonucleotide probes, which hybridize to either the wild type allele or the mutant allele, or both. For example genotyping with BHQPLUS® probes uses two allele specific probes and two primers that flank the region of the polymorphism, and during thermal cycling the polymerase encounters the allele-specific probes bound to the DNA and releases a fluorescent signal. Allele discrimination involves competitive binding of the two allele-specific BHQPLUS® probes (see also biosearchtech.com).

Examples of genotyping assays are the KASP-assay (by LGC, see www at LGCgenomics.com and also WWW at biosearchtech.com/products/pcr-kits-and-reagents/genotyping-assays/kasp-genotyping-chemistry), based on competitive allele-specific PCR and end-point fluorescent detection, the TAQMAN®-assay (Applied Biosystems), which is also PCR based, HRM assays (High Resolution Melting Assay), wherein allele-specific probes are detected using real time PCR, or the rhAmp assay, based on Rnase H2-dependent PCR, BHQPLUS® genotyping, BHQplex CoPrimer genotyping and many others.

The KASP-assay is also described in He C, Holme J, Anthony J. 'SNP genotyping: the KASP assay. Methods Mol Biol. 2014; 1145:75-86' and EP1726664B1 or U.S. Pat. No. 7,615,620 B2, incorporated by reference. The KASP genotyping assay utilizes a unique form of competitive allele-specific PCR combined with a novel, homogeneous, fluorescence-based reporting system for the identification and measurement of genetic variation occurring at the nucleotide level to detect single nucleotide polymorphisms (SNPs) or inserts and deletions (InDels). The KASP technology is suitable for use on a variety of equipment platforms and provides flexibility in terms of the number of SNPs and the number of samples able to be analyzed. The KASP chemistry functions equally well in 96-, 384-, and 1,536-well microtiter plate formats and has been utilized over many years in large and small laboratories by users across the fields of human, animal, and plant genetics.

The TAQMAN® genotyping assays is also described in Woodward J. 'Bi-allelic SNP genotyping using the TAQMAN® assay.' Methods Mol Biol. 2014; 1145:67-74, U.S. Pat. Nos. 5,210,015 and 5,487,972, incorporated herein by reference. With TAQMAN® technology allele-specific probes are utilized for quick and reliable genotyping of known polymorphic sites. TAQMAN® assays are robust in genotyping multiple variant types, including single nucleotide polymorphisms, insertions/deletions, and presence/absence variants. To query a single bi-allelic polymorphism, two TaqMan probes labeled with distinct fluorophores are designed such that they hybridize to different alleles during PCR-based amplification of a surrounding target region. During the primer extension phase of PCR, the 5'-3' exonuclease activity of Taq polymerase cleaves and releases the fluorophores from bound probes. At the end of PCR, the emission intensity of each fluorophore is measured and allele determination at the queried site can be made.

Various genotyping assays can, therefore, be used, which can differentiate between the presence of the wild type allele of the WAP5.1 gene, encoding the protein of SEQ ID NO: 1 or 9, or a mutant allele of the WAP5.1 gene. Various mutant alleles of the WAP5.1 gene can be detected. So, not only the mutant allele encoding the protein of SEQ ID NO: 4 or of SEQ ID NO: 10 (comprising the L528F mutation), but the assay can be designed to detect any other mutant allele of the WAP5.1 gene, including those described in Table 1 and others.

As mentioned preferably a bi-allelic genotyping assay is used, e.g. a KASP-assay, a TAQMAN® assay, a BHOPLUS® assay, PACE genotyping (see world wide web at idtdna.com/pages/products/qpcr-and-pcr/genotyping/pace-snp-genotyping-assays) or any other bi-allelic genotyping assay.

In one aspect the genotyping assay in step b) of the methods above is a KASP-assay. Thus in step b) a competitive PCR is carried out using two forward primers and one common reverse primer. The two forward primers comprise at least 10, 11, 12, 13, 14, 15, 16, 17, 18, 19 or 20 nucleotides complementary to the genomic sequence (or the complement strand thereof). In addition the two forward primers comprise 1, 2, 3 or more nucleotides (preferably at the 3' end of the primers) which provide specificity to the SNP or INDEL which differentiates the wild type sequence from the mutant sequence of the allele. The two forward primers thereby have different binding specificity (or preference) to either the wild type allele or to the mutant allele. For example the Fam-primer may comprise e.g. 17 nucleotides of the wild type sequence and 1 nucleotide specific for the nucleotide of the mutant allele, and the VIC-primer may comprise 18 nucleotides of the wild type allele and 1 nucleotide specific to the nucleotide of the wild type allele. A KASP-assay can easily be designed to differentiate between the wild type allele and any mutant allele of the WAP5.1 gene which differs from the wild type allele in one or more nucleotides being inserted, deleted or replaced, so e.g. the assay can be designed for any SNP or INDEL that differentiates two alleles.

It is noted that genotyping assays, such as the KASP assay, can also be carried out to detect the mutant and/or wild type WAP5.1 allele in triploid or tetraploid watermelon plants and plant parts in the same way as described for diploid watermelon plants and plant parts.

In one aspect the mutant allele of the WAP5.1 gene encodes a protein comprising one or more amino acids inserted, replaced or deleted with respect of the wild type protein of SEQ ID NO: 1 or 9, as already described elsewhere herein.

Therefore, in one embodiment a method is provided for detecting, and optionally selecting, a watermelon plant, seed or plant part comprising at least one copy of a wild type allele and/or of a mutant allele of a gene named WAP5.1, comprising:

- a) providing genomic DNA of a watermelon plant or of a plurality of plants (e.g. a breeding population, F2, backcross, etc.),
- b) carrying out an assay (e.g. a bi-allelic genotyping assay) that discriminates or can discriminate between the presence of alleles in the genomic DNA of a), based on nucleic acid amplification (e.g. comprising the use of allele specific oligonucleotide primers) and/or nucleic acid hybridization (e.g. comprising the use of allele-specific oligonucleotide probes), to detect the presence of a wild type allele of the gene and/or a mutant allele of the gene, wherein the wild type allele encodes a protein of SEQ ID NO: 1 or 9 (or a wild type WAP5.1 protein comprising at least 95%, 96%, 97%, 98%, 99%, 99.5% or 99.8% or 99.9% identity to SEQ ID NO: 1 or 9), and the mutant allele encodes a protein comprising one or more amino acids inserted, deleted or replaced with respect to the wild type protein of SEQ ID NO: 1 or 9 (or with respect to a wild type WAP5.1 protein comprising at least 95%, 96%, 97%, 98%, 99%, 99.5% or 99.8% or 99.9% identity to SEQ ID NO: 1 or 9), and optionally
- c) selecting a plant, seed or plant part comprising one or two copies of the mutant allele.

Under step b) the genotyping assay discriminates between the wild type and the mutant alleles based on nucleic acid (especially DNA) amplification reactions making use of e.g. oligonucleotide primers, such as PCR (Polymerase Chain Reaction) and PCR primers, preferably allele-specific primers, and/or nucleic acid hybridization making use of as oligonucleotide probes, preferably allele-specific probes.

The primers or probes are preferably modified to comprise a label, e.g. a fluorescent label, or to comprise a tail sequence or other modification.

In one aspect, in any of the above methods the assay uses one or more WAP5.1 allele specific primers or one or more WAP5.1 allele specific probes. As mentioned, based on the genomic sequence of SEQ ID NO: 7 or 14 or other (e.g. degenerate) genomic sequences which encode the protein of SEQ ID NO: 1 or 9 or the genomic sequence of a mutant allele which encodes e.g. a protein comprising one or more amino acids inserted, deleted or replaced in comparison to SEQ ID NO: 1 or 9, PCR primers and nucleic acid probes can be designed using known methods or software programs for oligonucleotide design. Primers and probes may for example be at least 10, 11, 12, 13, 14, 15, 16, 17, 18, 19, 20, 21, 22, 23, 24 or more nucleotides (bases) in length and anneal to (or hybridize to) the template DNA sequence, i.e. they preferably have at least 95%, 96%, 97%, 98%, 99% or 100% sequence identity to the target sequence. The primer or probe specificity to a wild type allele or a mutant allele is due to at least 1, 2, 3 or more nucleotides of the primer or probe being specific for either allele. The primers or probes are thus designed around the polymorphism (e.g. the SNP or InDel) between the two alleles of the target gene, so that they discriminate between these. In one aspect the assay is a bi-allelic genotyping assay selected from e.g. a KASP-assay, a TAQMAN®-assay, a BHQPLUS® probe assay or any other bi-allelic genotyping assay.

In one aspect, the mutant allele comprises at least one codon inserted or duplicated in the coding region of the allele, or at least one codon changed into another codon (e.g. through a single nucleotide change), or at least one codon deleted or changed into a STOP codon.

In any of the methods above, in one aspect the mutant allele encodes a protein as described in Table 1. Thus, in one aspect the methods can be used to discriminate between plants, seeds or plant parts comprising two copies of the wild type WAP5.1 allele encoding the protein of SEQ ID NO: 1 or 9, two copies of the mutant WAP5.1 allele encoding the mutant protein of Table 1, or one copy of each allele (heterozygous). Optionally plants, plant parts or seeds comprising any of these genotypes may be selected for e.g. further breeding or for use in watermelon production.

Although any DNA genotyping assay may be used in the above methods, be it PCR based (using PCR primers) and/or hybridization based (using probes), in one aspect a KASP-assay is used to discriminate between the wild type and the mutant allele. The assay can be used in a high throughput way, e.g. in 96 well plates or more well plates (e.g. 384 well plates).

In one aspect the assay discriminates between the C/T SNP at nucleotide 61 of SEQ ID NO: 8. So the primers or probes detect the allele comprising the C or the T at nucleotide 61 of SEQ ID NO: 8.

Depending on the SNP or INDEL between the wild type and mutant WAP5.1 allele, various allele-specific primers and probes can be designed for use in the assays.

In one aspect two forward primers (one for the wild type allele and one for the mutant allele) and one common reverse primer (for both the wild type and the mutant allele) are used in the KASP-assay. In one aspect the two forward primers and the reverse primer comprise at least 10, 11, 12, 13, 14, 15, 16, 17, 18, 19 or more nucleotides of genomic WAP5.1 sequence or of the complement sequence thereof. The forward primers further comprise at least 1, 2, or 3 nucleotides (preferably at the 3' end of the primer) which confer specificity (or preference) to either amplification of the wild type allele or amplification of the mutant allele. Each forward primer forms a primer pair with the common reverse primer to amplify the DNA sequence of the target allele in between the primer pair, during thermal cycling. Standard components for thermal cycling are used and standard components for KASP-assays.

In another embodiment a method is provided for producing a hybridization product or an amplification product of a wild type allele and/or of a mutant allele of a gene named WAP5.1, comprising:
  a) providing genomic DNA of a watermelon plant or of a plurality of plants (e.g. a breeding population, F2, backcross, etc.),
  b) carrying out an assay (e.g. a bi-allelic genotyping assay) that discriminates or can discriminate between the presence of alleles in the genomic DNA of a), which assay generates a nucleic acid amplification product (e.g. through the use of allele specific oligonucleotide primers to generate the product) and/or which assay generates a nucleic acid hybridization product (e.g. through the use of allele-specific oligonucleotide probes to generate the hybridization product), whereby the amplification product or hybridization product indicates the presence of a wild type allele of the gene and/or a mutant allele of the gene in the DNA, wherein the wild type allele encodes the protein of SEQ ID NO: 1 or 9) and the mutant allele encodes a protein comprising one or more amino acids inserted, duplicated, deleted or replaced with respect to the wild type protein of SEQ ID NO: 1 or 9), and optionally
  c) selecting a plant, seed or plant part comprising one or two copies of the mutant allele.

Also a method of amplifying all or part of a mutant and/or wild type WAP5.1 allele from a genomic DNA sample derived from a watermelon plant, plant part or seed is provided, comprising contacting genomic DNA with a primer pair which amplifies all or part of the mutant WAP5.1 or wild type WAP5.1 allele in the sample, and detecting the amplification product.

Also a method of hybridizing a probe to a mutant and/or wild type WAP5.1 allele in a genomic DNA sample derived from a watermelon plant, plant part or seed is provided, comprising contacting genomic DNA with a oligonucleotide probe which hybridizes to the mutant WAP5.1 or wild type WAP5.1 allele in the sample, and detecting the hybridization product.

All embodiments described above and elsewhere herein also apply to these embodiments. The amplification product may thus be a PCR amplification product, e.g. competitive PCR amplification product generated in e.g. a KASP assay or other assay, to detect the mutant and/or wild type allele in the DNA sample. The hybridization product may thus be a hybridization product of an oligonucleotide probe which hybridizes to the nucleic acid in the DNA sample, to detect the mutant and/or wild type allele in the DNA sample. The primer pairs or probes preferably are allele specific, and the products are thus distinguishable as being either two copies of the wild type allele, two copies of the mutant allele or one copy of each being present in the genomic DNA of the watermelon plant, plant part or seed.

The primers or probes are preferably modified, e.g. labelled by a tail sequence or fluorescent label or otherwise modified with respect to the wild type sequence which they amplify or hybridize.

As the described methods require detection of a mutant and/or wild type allele in the genomic DNA of the plant, plant part or seed, the genomic DNA needs to be accessible for detection, e.g. it may be extracted from the plant cells using DNA extraction methods or at least eluted from the damaged cells into a solution (e.g. a buffer solution).

As the ortholog genes in other Cucurbitaceae are provided herein, the above methods can also be applied to other WAP5.1 genes and alleles in other species, especially cucumber and melon.

In one aspect, therefore, a genotyping assay is provided for genotyping watermelon, cucumber or melon plants, seeds, plant parts, cells or tissues, comprising the steps:
  a) providing genomic DNA of one or more watermelon, cucumber or melon plants or a population of plants (e.g. breeding population, F2 population, backcross population etc.), and
  b) carrying out a genotyping assay which is able to detect (or which detects) the presence of the wild type allele encoding the protein of SEQ ID NO: 1 or 9 or a protein comprising at least 95% sequence identity thereto (watermelon wild type WAP5.1 protein) or SEQ ID NO: 2 or a protein comprising at least 95% sequence identity thereto (cucumber wild type WAP5.1 protein) or SEQ ID NO: 3 or a protein comprising at least 95% sequence identity thereto (melon wild type WAP5.1 protein) and/or the presence of a mutant allele, wherein the mutant allele comprises one or more amino acids inserted, deleted, replaced or duplicated with respect of SEQ ID NO: 1 or 9 (or with respect to the wild type sequence comprising at least 95% identity thereto), or SEQ ID NO: 2 (or with respect to the wild type sequence comprising at least 95% identity thereto) or SEQ ID NO: 3 (or with respect to the wild type sequence comprising at least 95% identity thereto), and optionally
  c) selecting a plant, seed, plant part, cell or tissue comprising either two copies of the wild type allele, or one copy of the wild type allele and one copy of a mutant allele, or two copies of a mutant allele.

Thus, a method is provided for detecting, and optionally selecting, a watermelon, cucumber or melon plant, seed or plant part comprising at least one copy of a wild type allele and/or of a mutant allele of a gene named ClWAP5.1 (*Citrullus lanatus* WAP5.1), CsWAP5.1 (*Cucumis sativus* WAP5.1) or CmWAP5.1 (*Cucumis melo* WAP5.1) comprising:
  a) carrying out an assay on a genomic DNA sample obtained from at least one plant that detects or discriminates between WAP5.1 alleles based on nucleic acid amplification and/or nucleic acid hybridization to detect the presence of a wild type allele of the gene and/or a mutant allele of the gene, wherein the wild type allele encodes the protein of SEQ ID NO: 1 or 9 or a protein comprising at least 95% sequence identity thereto (in watermelon), SEQ ID NO: 2 or a protein comprising at least 95% sequence identity thereto (in cucumber) and SEQ ID NO: 3 or a protein comprising at least 95% sequence identity thereto (in melon) and the mutant allele comprises one or more amino acids inserted, deleted or replaced with respect to SEQ ID NO: 1 or 9 (or with respect to the wild type sequence comprising at least 95% identity thereto), SEQ ID NO: 2 (or with respect to the wild type sequence comprising at least 95% identity thereto) or SEQ ID NO: 3 (or with respect to the wild type sequence comprising at least 95% identity thereto), and optionally
  b) selecting a plant, seed or plant part comprising one or two copies of the mutant allele.

Further a method is provided for determining the genotype of the WAP5.1 gene, and optionally selecting, a watermelon, cucumber or melon plant, seed or plant part comprising certain genotype, e.g. at least one copy of a wild type allele and/or of a mutant allele of a gene named ClWAP5.1 (*Citrullus lanatus* WAP5.1), CsWAP5.1 (*Cucumis sativus* WAP5.1) or CmWAP5.1 (*Cucumis melo* WAP5.1) comprising:

a) carrying out a bi-allelic genotyping assay on one or more genomic DNA samples, obtained from one or more plants, wherein said genotyping assay detects or discriminates between WAP5.1 alleles based on WAP5.1 allele-specific primers and/or WAP5.1 allele-specific probes which allele specific primers or allele specific probes detect the presence of a wild type allele of the gene or of a mutant allele of the gene, wherein the wild type allele encodes the protein of SEQ ID NO: 1 or 9 or a protein comprising at least 95% sequence identity thereto (in watermelon), SEQ ID NO: 2 or a protein comprising at least 95% sequence identity thereto (in cucumber) and SEQ ID NO: 3 or a protein comprising at least 95% sequence identity thereto (in melon) and the mutant allele comprises one or more amino acids inserted, deleted or replaced with respect to SEQ ID NO: 1 or 9 (or with respect to the wild type sequence comprising at least 95% identity thereto), SEQ ID NO: 2 (or with respect to the wild type sequence comprising at least 95% identity thereto) or SEQ ID NO: 3 (or with respect to the wild type sequence comprising at least 95% identity thereto), and optionally b) selecting one or more plants, seeds or plant parts comprising one or two copies of the mutant allele.

Such an assay can be used for marker assisted selection (MAS) of plants in e.g. a breeding program to select plants comprising a certain genotype, e.g. homozygous for the wild type allele of the WAP5.1 gene, homozygous or heterozygous for a mutant allele of the WAP5.1 allele.

Therefore, also a method of breeding watermelon, cucumber or melon plants is provided herein, said method comprising genotyping one or more plants for the allele composition at the WAP5.1 locus in the genome and optionally selecting one or more plants having a specific genotype at the WAP5.1 locus. In one aspect also genotyping-by-sequencing may be done for the WAP5.1 gene.

As mentioned, optionally the plants or seeds which comprise two copies of a mutant WAP5.1 allele can be grown and phenotyped for facultative parthenocarpy. The mutant allele is in one aspect a mutant allele which, in homozygous form, confers facultative parthenocarpy.

In a different aspect a watermelon, cucumber or melon plant, seed or plant part is provided comprising at least one copy of a mutant allele of a gene named ClWAP5.1 in watermelon, CsWAP5.1 in cucumber and CmWAP5.1 in melon, wherein said mutant allele either a) comprises one or more mutations in a regulatory element, resulting in no expression or reduced expression of the allele compared to the wild type allele, and/or b) encodes a mutant protein comprising one or more amino acids replaced, inserted, or deleted compared to the wild type protein, wherein said mutant allele of a) or b) confers facultative parthenocarpy when the mutant allele is in homozygous form (compared to the plant comprising the wild type allele in homozygous form), and wherein the wild type watermelon ClWAP5.1 allele encodes a protein of SEQ ID NO: 1 or 9 or a protein comprising at least 95%, 96%, 97%, 98%, 99% or more sequence identity to SEQ ID NO: 1 or 9, wherein the wild type cucumber CsWAP5.1 allele encodes a protein of SEQ ID NO: 2 or a protein comprising at least 95%, 96%, 97%, 98%, 99% or more sequence identity to SEQ ID NO: 2, wherein the wild type melon CmWAP5.1 allele encodes a protein of SEQ ID NO: 3 or a protein comprising at least 95%, 96%, 97%, 98%, 99% or more sequence identity to SEQ ID NO: 3.

Breeding Methods

Further a method of crossing a plant comprising at least one mutant WAP5.1 allele as described herein with a plant, e.g. lacking a mutant WAP5.1 allele, is provided and selecting progeny comprising at least one copy of the mutant WAP5.1 allele is provided.

Thus, in one aspect a method for generating a watermelon, cucumber or melon plant is provided comprising the steps of:

a) Providing a watermelon, cucumber or melon plant comprising at least one copy of a mutant WAP5.1 allele, as described;

b) Crossing said watermelon, cucumber or melon plant with another watermelon, cucumber or melon plant to produce F1 seeds;

c) Optionally selfing the watermelon plants grown from F1 seeds one or more times to produce F2, F3 or further generation selfing progeny;

d) Crossing said F1 or further generation selfing progeny to the plant of step b), to produce a backcross progeny;

e) Selecting backcross progeny which comprise the mutant WAP5.1 allele of step a).

Optionally the plant of step e) comprises two copies of the mutant WAP5.1 allele and is facultative parthenocarpic.

Optionally selection or detection of the presence of the mutant WAP5.1 allele in any of the steps can be done using molecular methods, such as SNP or INDEL genotyping, sequencing and the like.

Preferably the allele in step a) is a mutant allele which confers facultative parthenocarpy when in homozygous form. In one aspect the plant in step a) is a watermelon plant comprising a mutant allele of Table 1, either in heterozygous or homozygous form.

Also provided is a method for production of a watermelon plant comprising the steps of:

a) introducing mutations in a population of watermelon plants or providing a population of mutagenized watermelon plants, e.g. a TILLING population of the M2, M3 or further generation, b) identifying a plant which has a mutation in an allele encoding a WAP5.1 protein wherein the wild type allele of the gene encodes a WAP5.1 protein comprising at least 95% sequence identity to the protein of SEQ ID NO 1 or SEQ ID NO 9.

The method may further comprise one or both steps of selecting a plant comprising at least two copies of the mutant allele of step b), determining if the plant produces fruits in the absence of pollination.

Further any sequences and molecules of the sequences are encompassed, as are sequences comprising at least 90%, 95%, 96%, 97%, 98%, 99%, 99.5%, 99.8% or 99.9% sequence identity to the provided sequences. Also any fragments and/or modified sequences (e.g. primers or probes comprising at least 10, 15, 16, 17, 18, 19, 20 or more nucleotides of the sequence or the complement sequence) and their use in breeding (e.g. MAS) or in detecting or selecting plants or plant parts is provided.

When a mutant protein is described, it is clear that the genomic sequence and mRNA or cDNA sequence encoding the mutation leading to the mutation in the protein is encompassed herein and can be used to detect an allele in the genome comprising the mutation leading to the amino acid change, and to e.g. carry out a genotyping assay directed at the mutant allele.

Sequence Description

SEQ ID NO: 1: wild type WAP5.1 protein of watermelon.

SEQ ID NO: 2: wild type WAP5.1 protein of cucumber.

SEQ ID NO: 3: wild type WAP5.1 protein of melon.

SEQ ID NO: 4: mutant watermelon WAP5.1 protein, wherein amino acid L (Leucine) 528 is replaced by F (Phenylalanine).

SEQ ID NO: 5: cDNA encoding the mutant WAP5.1 protein of SEQ ID NO: 4.

SEQ ID NO: 6: cDNA encoding the wild type WAP5.1 protein of SEQ ID NO: 1.

SEQ ID NO: 7: genomic DNA encoding the wild type WAP5.1 protein of SEQ ID NO: 1.

SEQ ID NO: 8: SNP marker (mwm23348429) at nucleotide 61 (C/T) for detecting either the mutant wap5.1 allele or wild type Wap5.1 allele. In the wild type allele the codon CTT encodes Leucine, L528 of SEQ ID NO: 1 or SEQ ID NO: 9, or L535 of SEQ ID NO: 2 or L538 of SEQ ID NO: 3. In the mutant allele the C is changed to T (C→T), and the resulting mutated codon TTT encodes F, Phenylalanine instead of L, Leucine. Thus the SNP marker comprises a T at nucleotide 61 of SEQ ID NO: 8 or at a sequence comprising at least 92%, 93%, 94%, 95% or more sequence identity to SEQ ID NO: 8, can be used to detect the mutant wap5.1 allele, while the SNP marker comprising a C at nucleotide 61 of SEQ ID NO: 8, or at a sequence comprising at least 92%, 93%, 94%, 95% or more sequence identity to SEQ ID NO: 8, can be used to detect the wild type wap5.1 allele.

SEQ ID NO: 9: protein sequence of wild type watermelon WAP5.1 protein of watermelon line TY; note that amino acid 51 is an R (Arg).

SEQ ID NO: 10: mutant watermelon WAP5.1 protein present in line TY, wherein amino acid L (Leucine) 528 is replaced by F (Phenylalanine).

SEQ ID NO: 11: cDNA encoding the wild type protein of SEQ ID NO: 9.

SEQ ID NO: 12: cDNA encoding the mutant protein of SEQ ID NO: 10.

SEQ ID NO: 13: F-box domain.

SEQ ID NO: 14: genomic DNA encoding the wild type protein of SEQ ID NO: 9.

EXAMPLES

A watermelon mutant population (developed via EMS treatment of an elite line called TY) was screened with a forward screening approach in Chile and one mutant was found which produced fruits without pollination, in an insect proof greenhouse.

A single plant able to produce parthenocarpic fruits was selected and used to make several F2 mapping populations in different genetic backgrounds. In one population the QTL was mapped to a 0.47 Mb/8.2 cM region on chromosome 5. There were two mutations within this interval: the first mutation was in an intergenic region and a second mutation changed a highly conserved amino acid from a leucine (L) to a phenylalanine (L528F) in a gene named herein wap5.1.

This mutant wap5.1 allele was found to be completely unique to this line when it was compared to 93 whole genome re-sequenced lines.

Markers saturating the chromosome 5 interval were designed and run on the F2 population. The marker with the highest association with the trait, mWM23348429, was designed to the non-synonymous mutation in the wap5.1 gene. To confirm this mutation, an additional 92 F2 plants were genotyped with mWM23348429 and flanking markers. The highest associated marker was mWM23348429, which further confirmed the mutation this marker was designed to, was underlying the trait.

The wap5.1 gene is a single recessive gene and the facultative parthenocarpic phenotype co-segregated with the mutant wap5.1 allele in plants homozygous for the mutation (wap5.1/wap5.1).

RaptorX Contact Prediction was carried out for the wild type and mutant Wap5.1 proteins, showing that the L528F mutation lead to an incorrect 3-Dimensional protein folding of the LRR-domain, compared to the wild type protein, most likely significantly reducing the normal in vivo protein function or even abolishing the normal in vivo function completely. The LRR-domain is most likely involved in protein-protein interactions so that a small structural change of this highly ordered and highly conserved protein domain can have significant effects on function.

Orthologs of the Wap5.1 gene were identified using BLAST analysis. The cucumber and melon proteins contained an F-box domain which was identical between all three Cucurbitaceae species. Also the LRR-domain was highly conserved. Most of the amino acid variation was found to lie in the N-terminal protein parts which precede the F-box domain.

Further mutants in the wap5.1 gene were identified in the mutant watermelon population (see Table 1) and will be tested for their phenotype, in plants homozygous for the mutant allele.

Further, when looking at the genomic sequence of the WAP5.1 gene, in the wild type background watermelon line TY and in the mutant wap5.1 line (generated in the TY background), it was found the amino acid at position 51 was an R (Arg; Arginine, codon CGT at nucleotide 151 to 153 of SEQ ID NO: 11 and 12) rather than a G (Gly; Glycine, codon GGT at nucleotide 151 to 153 of SEQ ID NO: 6), which is found in the Charleston Grey reference genome. The R51 is found in both the wild type WAP5.1 protein of line TY and in the mutant wap5.1 protein (comprising the L528F substitution). The same R51 was also found in the wild type WAP5.1 protein of the watermelon 97103 genome, as described earlier herein.

Also in the TY-line the S450 (Serine 450) is encoded by codon AGC at nucleotide 1348 to 1350 of SEQ ID NO: 11 and 12, while in the Charleston Grey reference genome the S450 is encoded by codon AGT at nucleotide 1348 to 1350 of SEQ ID NO: 6. The wild type WAP5.1 protein of line TY is provided herein in SEQ ID NO: 9, and the cDNA encoding the wild type WAP5.1 protein of line TY is provided herein in SEQ ID NO: 11. The cDNA is identical to the cDNA of variety 97103 V2, found in the cucurbitgenomics.org database. The genomic sequence of SEQ ID NO: 14, encoding the wild type WAP5.1 protein is obtained from the watermelon variety 97103 V2 database.

The mutant wap5.1 protein found in the TY mutant population and comprising the L528F amino acid substitution is provided herein in SEQ ID NO: 10. Likewise the cDNA encoding this mutant protein is provided in SEQ ID NO: 12.

The wild type WAP5.1 protein of SEQ ID NO: 1 (Charleston Grey genome) and the wild type WAP5.1 protein of SEQ ID NO: 9 (TY-line and watermelon 97103 genome) comprise 99.9% sequence identity to each other, when aligned pairwise, as only a single amino acid is different.

The cDNA encoding the wild type WAP5.1 protein of SEQ ID NO: 1 (Charleston Grey genome) and the cDNA encoding the wild type WAP5.1 protein of SEQ ID NO: 9 (TY line) also comprise 99.9% sequence identity, with two nucleotides being different.

The watermelon plants homozygous for the mutant wap5.1 allele (comprising the L528F substitution) had normal growth and morphology. No abnormalities were observed during growth and development of the plants. The only phenotypic difference that could be seen in the homozygous wap5.1 mutant plants was that the mature fruits that developed in the absence of pollination had a slight triangular shape at one end, see FIG. 5. However, it is not clear if this is an effect of the mutation or a background effect.

The invention claimed is:

1. A watermelon plant or plant part comprising at least one copy of a mutant allele of an endogenous gene named Watermelon Parthenocarpy gene located on chromosome 5 (WAP5.1), wherein said mutant allele encodes an amino acid substitution of amino acid number L528 or P308 compared to the wild type protein, wherein said mutant allele confers facultative partheno-carpy when the mutant allele is in homozygous form, and wherein the wild type WAP5.1 allele encodes a protein of SEQ ID NO: 1 or SEQ ID NO: 9, or a protein comprising at least 95% sequence identity to SEQ ID NO: 1 or to SEQ ID NO: 9.

2. A watermelon plant or plant part comprising at least one copy of a mutant allele of an endogenous gene named Watermelon Parthenocarpy gene located on chromosome 5, WAP5.1, wherein said mutant allele comprises a substitution in the codon encoding amino acid number L528 or P308 compared to the wild type protein, wherein said mutant allele confers facultative parthenocarpy when the mutant allele is in homozygous form, and wherein the wild type WAP5.1 allele encodes a protein of SEQ ID NO: 1 or SEQ ID NO: 9, or a protein comprising at least 95% sequence identity to SEQ ID NO: 1 or to SEQ ID NO: 9.

3. The watermelon plant or plant part according to claim 1, wherein said mutant allele encodes the amino acid substitution L528F of SEQ ID NO: 1 or of SEQ ID NO: 9.

4. The watermelon plant or plant part according to claim 1, wherein said plant or plant part is diploid and is homozygous for the mutant allele.

5. The plant or plant part according to claim 1, wherein the watermelon plant is diploid, triploid or tetraploid.

6. The plant or plant part according to claim 5, wherein the diploid plant or plant part comprises two copies, the triploid plant or plant part comprises one, two or three copies and the tetraploid plant or plant part comprises two or four copies of the mutant allele.

7. A seed from which a plant or plant part according to claim 1 can be grown.

8. A fruit produced by a plant according to claim 1, optionally wherein the fruit is seedless and is produced in the absence of pollination.

9. The plant or plant part according to claim 1, wherein said plant or plant part further comprises a gene conferring male sterility or a gene conferring stenospermocarpy or another gene conferring parthenocarpy.

10. The plant part according to claim 1, wherein the plant part is a cell, a flower, a leaf, a stem, a cutting, an ovule, pollen, a root, a rootstock, a scion, a fruit, a protoplast, an embryo, or an anther.

11. A vegetatively propagated plant propagated from a plant part according to claim 10.

12. A method of producing seedless watermelon fruits, said method comprising growing a diploid watermelon plant comprising two copies of a mutant allele according to claim 1, whereby pollination of the flowers is prevented during the growing and harvesting the seedless fruits produced from the unpollinated flowers.

13. A method of producing seedless watermelon fruits, said method comprising growing a triploid watermelon plant comprising one, two or three copies of a mutant allele according to claim 1, whereby no pollenizer plant is present during the growing and harvesting the seedless fruits produced from the unpollinated flowers.

14. A method for screening watermelon plants, watermelon seeds, watermelon plant parts, or DNA therefrom, for the presence of a mutant allele of a gene named WAP5.1, or for selecting a watermelon plant, seed or plant part comprising a mutant allele of a gene named WAP5.1, said method comprising the steps:

a) analyzing whether the genomic DNA comprises a wild type WAP5.1 allele which encodes a protein of SEQ ID NO: 1 or 9, or a protein comprising at least 95% sequence identity to SEQ ID NO: 1 or to SEQ ID NO: 9, and/or a mutant WAP5.1 allele which encodes a mutant protein comprising an amino acid substitution of amino acid number L528 or P308 compared to the wild type WAP5.1 protein, and optionally b) selecting a plant, seed or plant part comprising two copies of the wild type allele, two copies of the mutant allele or one copy of the wild type allele and one copy of the mutant allele.

15. A method for producing a watermelon plant, said method comprising crossing a watermelon plant comprising at least one mutant WAP5.1 allele according to claim 1 with another watermelon plant, and producing a watermelon plant comprising at least one copy of the mutant WAP5.1 allele.

16. The watermelon plant or plant part according to claim 1, wherein said mutant allele encodes the amino acid substitution P308L of SEQ ID NO: 1 or of SEQ ID NO: 9.

17. The watermelon plant or plant part according to claim 2, wherein said plant or plant part is diploid and is homozygous for the mutant allele.

18. The plant or plant part according to claim 2, wherein the watermelon plant is diploid, triploid or tetraploid.

19. A seed from which a plant or plant part according to claim 2 can be grown.

20. A fruit produced by a plant according to claim 2, optionally wherein the fruit is seedless and is produced in the absence of pollination.

21. The plant part according to claim 2, wherein the plant part is a cell, a flower, a leaf, a stem, a cutting, an ovule, pollen, a root, a rootstock, a scion, a fruit, a protoplast, an embryo, or an anther.

22. A method of producing seedless watermelon fruits, said method comprising growing a diploid watermelon plant comprising two copies of a mutant allele according to claim 2, whereby pollination of the flowers is prevented during the growing and harvesting the seedless fruits produced from the unpollinated flowers.

23. A method of producing seedless watermelon fruits, said method comprising growing a triploid watermelon plant comprising one, two or three copies of a mutant allele according to claim 2, whereby no pollenizer plant is present during the growing and harvesting the seedless fruits produced from the unpollinated flowers.

24. A method for producing a watermelon plant, said method comprising crossing a watermelon plant comprising at least one mutant WAP5.1 allele according to claim 2 with another watermelon plant, and producing a watermelon plant comprising at least one copy of the mutant WAP5.1 allele.

* * * * *

SEQUENCE LISTING

```
<160> NUMBER OF SEQ ID NOS: 14

<210> SEQ ID NO 1
<211> LENGTH: 1033
<212> TYPE: PRT
<213> ORGANISM: artificial
<220> FEATURE:
<223> OTHER INFORMATION: Wild type watermelon WAP5.1 protein

<400> SEQUENCE: 1

Met Thr Ile Trp Cys Cys Leu Cys Phe Thr Val Gly Glu Glu Asp Glu
1               5                   10                  15

Arg Glu Arg Glu Glu Glu Leu Lys Lys Glu Gly Glu Met Lys Pro Met
                20                  25                  30

Met Arg Glu Glu Val Phe Glu Asn Gln Asp Asp Ser Asp Arg Ile Val
            35                  40                  45

Arg Asn Gly Asp Asp Ser Gln Gly Ser Asn Pro Leu Pro Ile Ala Val
        50                  55                  60

Asp Asp Ala Pro Asp Arg His Asp Gly Asp Arg Leu Arg Leu Phe Glu
65                  70                  75                  80

Asp Met Val Arg Ala Met His Asp Gly Ala Asp Gly Gly Gly Ala His
                85                  90                  95

Trp Asp Asp Glu Leu Arg Gly Gly Gly Gly Ala Ile Asn Pro Trp
                100                 105                 110

Asn Phe Ser Phe Gly Ile Leu His Gln Ser Glu Gly Gly Glu Ser Ser
            115                 120                 125

Ser Ala Ser Ala Leu Ser Leu Ser Ser Thr Val Glu Thr Ser Asn Glu
        130                 135                 140

Glu Arg Asp Arg Asp Ala Asn His Lys Arg Ala Lys Val Leu Ser Lys
145                 150                 155                 160

Phe Thr Glu Ser Ser Phe Ala Thr Pro Trp Pro Leu Gly Ala Gly Asn
                165                 170                 175

Pro Met Arg Asp Tyr Asp Phe Ile His Gly Ser Ser Ser Ile Met Ser
                180                 185                 190

Arg Asn Glu Phe Leu Tyr His Ala Ser Thr Ser Cys Arg Val Asp Glu
            195                 200                 205

Asp Leu Glu Ser Ser Phe Gly Arg Asp Asp Gly Ile Asn Asp Asn Asp
        210                 215                 220

Thr Cys Lys Ser Glu Gly Phe Glu Val Arg Met Asp Leu Thr Asp Asp
225                 230                 235                 240

Leu Leu His Met Val Phe Ser Phe Leu Asp His Ile Asn Leu Cys Arg
                245                 250                 255

Ala Ala Ile Val Cys Arg Gln Trp Gln Ala Ala Ser Ala His Glu Asp
                260                 265                 270

Phe Trp Arg Cys Leu Asn Phe Glu Asn Arg Asn Ile Ser Met Glu Gln
            275                 280                 285
```

```
Phe Glu Asp Met Cys Gly Arg Tyr Pro Asn Ala Thr Glu Val Asn Ile
    290                 295                 300

Ser Gly Val Pro Ala Val His Leu Leu Ala Met Lys Ala Val Ser Ser
305                 310                 315                 320

Leu Arg His Leu Glu Val Leu Thr Leu Gly Arg Gly Gln Leu Ala Asp
                325                 330                 335

Asn Phe Phe His Ala Leu Thr Asp Cys His Leu Leu Lys Ser Leu Thr
            340                 345                 350

Val Asn Asp Ser Thr Leu Val Asn Val Thr Gln Glu Ile Pro Ile Ser
            355                 360                 365

His Asp Arg Leu Arg His Leu His Leu Thr Lys Cys Arg Val Ile Arg
    370                 375                 380

Ile Ser Val Arg Cys Pro Gln Leu Glu Thr Leu Ser Leu Lys Arg Ser
385                 390                 395                 400

Asn Met Ala Gln Ala Val Leu Asn Cys Pro Leu Leu Arg Asp Leu Asp
                405                 410                 415

Ile Gly Ser Cys His Lys Leu Ser Asp Ala Ala Ile Arg Ser Ala Ala
            420                 425                 430

Ile Ser Cys Pro Gln Leu Glu Ser Leu Asp Met Ser Asn Cys Ser Cys
            435                 440                 445

Val Ser Asp Glu Thr Leu Arg Glu Ile Ser Ala Asn Cys Pro Asn Leu
    450                 455                 460

Gln Leu Leu Asn Ala Ser Tyr Cys Pro Asn Ile Ser Leu Glu Ser Val
465                 470                 475                 480

Arg Leu Thr Met Leu Thr Val Leu Lys Leu His Ser Cys Glu Gly Ile
                485                 490                 495

Thr Ser Ala Ser Met Thr Ala Ile Ser Ser Ser Gly Leu Lys Val
                500                 505                 510

Leu Glu Leu Asp Asn Cys Ser Leu Leu Thr Ser Val Ser Leu Asp Leu
            515                 520                 525

Pro His Leu Gln Asn Ile Arg Leu Val His Cys Arg Lys Phe Ser Asp
    530                 535                 540

Leu Ser Leu Gln Ser Val Lys Leu Ser Ser Ile Met Val Ser Asn Cys
545                 550                 555                 560

Pro Ser Leu His Arg Ile Asn Ile Thr Ser Asn Leu Leu Gln Lys Leu
                565                 570                 575

Val Leu Lys Lys Gln Glu Ser Leu Ala Lys Leu Val Leu Gln Cys Pro
                580                 585                 590

Ser Leu Gln Asp Val Asp Leu Thr Asp Cys Glu Ser Leu Thr Asn Ser
            595                 600                 605

Ile Cys Glu Val Phe Ser Asp Gly Gly Gly Cys Pro Met Leu Lys Ser
    610                 615                 620

Leu Val Leu Asp Asn Cys Glu Ser Leu Thr Ala Val Arg Phe Cys Ser
625                 630                 635                 640

Ser Ser Leu Gly Ser Leu Ser Leu Val Gly Cys Arg Ala Ile Thr Ser
                645                 650                 655

Leu Glu Leu Gln Cys Pro Asn Leu Glu Gln Val Ser Leu Asp Gly Cys
            660                 665                 670

Asp His Leu Glu Arg Ala Ser Phe Ser Pro Val Gly Leu Arg Ser Leu
    675                 680                 685

Asn Leu Gly Ile Cys Pro Lys Leu Asn Glu Leu Lys Leu Glu Ala Pro
    690                 695                 700

Arg Met Asp Leu Leu Glu Leu Lys Gly Cys Gly Gly Leu Ser Glu Ala
```

```
705                710                715                720

Ala Ile Asn Cys Pro Arg Leu Thr Ser Leu Asp Ala Ser Phe Cys Gly
                725                730                735

Gln Leu Lys Asp Glu Cys Leu Ser Ala Thr Thr Ala Ser Cys Pro Gln
                740                745                750

Ile Glu Ser Leu Ile Leu Met Ser Cys Pro Ser Val Gly Ser Glu Gly
                755                760                765

Leu Tyr Ser Leu Arg Cys Leu Leu Lys Leu Val Val Leu Asp Leu Ser
                770                775                780

Tyr Thr Phe Leu Met Ser Leu Gln Pro Val Phe Glu Ser Cys Ile Gln
785                790                795                800

Leu Lys Val Leu Lys Leu Gln Ala Cys Lys Tyr Leu Thr Asp Ser Ser
                805                810                815

Leu Glu Pro Leu Tyr Lys Glu Asp Ala Leu Pro Ala Leu Gln Glu Leu
                820                825                830

Asp Leu Ser Tyr Gly Thr Leu Cys Gln Ser Ala Ile Glu Glu Leu Leu
                835                840                845

Ala Cys Cys Thr His Leu Thr His Val Ser Leu Asn Gly Cys Val Asn
850                855                860

Met His Asp Leu Asn Trp Gly Cys Ser Ile Gly Gln Leu Ser Leu Ser
865                870                875                880

Ser Ile Pro Ile Pro Leu Gly Gln Ala Thr Leu Asp Glu Ile Glu Glu
                885                890                895

Pro Val Ala Gln Pro Asn Arg Leu Leu Gln Asn Leu Asn Cys Val Gly
                900                905                910

Cys Gln Asn Ile Arg Lys Val Leu Ile Pro Pro Ala Ala Arg Cys Phe
                915                920                925

His Leu Ser Ser Leu Asn Leu Ser Leu Ser Ser Asn Leu Lys Glu Val
                930                935                940

Asp Val Ser Cys Tyr Asn Leu Cys Phe Leu Asn Leu Ser Asn Cys Cys
945                950                955                960

Ser Leu Glu Val Leu Lys Leu Asp Cys Pro Arg Leu Thr Ser Leu Phe
                965                970                975

Leu Gln Ser Cys Asn Ile Glu Glu Glu Val Val Val Ala Ala Val Ser
                980                985                990

Arg Cys Ser Met Leu Glu Thr Leu  Asp Val Arg Leu Cys  Pro Lys Ile
                995                1000               1005

Ser Ser  Ile Ser Met Val Gln  Leu Arg Ile Ala Cys  Pro Ser Leu
        1010               1015               1020

Lys Arg  Ile Phe Ser Thr Leu  Ser Pro Thr
        1025               1030
```

```
<210> SEQ ID NO 2
<211> LENGTH: 1040
<212> TYPE: PRT
<213> ORGANISM: artificial
<220> FEATURE:
<223> OTHER INFORMATION: wild type cucumber WAP5.1 ortholog

<400> SEQUENCE: 2

Met Thr Ile Trp Cys Cys Leu Cys Phe Thr Val Gly Glu Glu Glu Glu
1                5                10                15

Glu Asp Glu Arg Ala Arg Glu Glu Glu Val Lys Lys Glu Glu Gly Glu
                20                25                30

Met Lys Pro Met Met Arg Glu Glu Val Phe Glu Asn Gln Asp Asp Ser
```

-continued

```
              35                  40                  45
Asp Arg Ile Val Arg Asn Gly Asp Asp Ser Gln Gly Ser Asn Pro Leu
        50                  55                  60

Ala Ser Ala Val Asp Asp Val Pro Glu Arg His Asp Gly Asp Arg Leu
65                  70                  75                  80

Arg Leu Phe Glu Asp Met Val Arg Ala Met His Asp Gly Gly Asp Gly
                85                  90                  95

Gly Ala His Trp Asp Asp Glu Leu Arg Gly Ala Gly Ala Gly Gly Gly
            100                 105                 110

Ala Ile Asn Pro Trp Asn Leu Ser Phe Gly Ile Met His Gln Ser Glu
            115                 120                 125

Gly Gly Glu Ser Ser Ser Ala Ser Ala Leu Pro Leu Ser Ser Met Val
        130                 135                 140

Glu Thr Ser Met Glu Glu Arg Asp Arg Asp Ala His His Lys Arg Ala
145                 150                 155                 160

Lys Val His Ser Lys Phe Ile Glu Ser Ser Phe Ala Thr Pro Trp Pro
                165                 170                 175

Leu Gly Ala Gly Asn Pro Met Arg Glu Tyr Asp Phe Ile His Gly Ser
            180                 185                 190

Pro Ser Ile Met Ser Arg Asn Glu Phe Leu Tyr His Ala Ser Thr Ser
            195                 200                 205

Ser Arg Phe Asp Ala Asp Lys Asp Leu Glu Ser Ser Phe Gly Arg Asp
        210                 215                 220

Asp Gly Ile Asn Glu Asn Asp Thr Cys Lys Ser Glu Gly Phe Glu Val
225                 230                 235                 240

Arg Met Asp Leu Thr Asp Asp Leu Leu His Met Val Phe Ser Phe Leu
                245                 250                 255

Asp His Ile Asn Leu Cys Arg Ala Ala Ile Val Cys Arg Gln Trp Gln
            260                 265                 270

Ala Ala Ser Ala His Glu Asp Phe Trp Arg Cys Leu Asn Phe Glu Asn
        275                 280                 285

Lys Asn Ile Ser Met Glu Gln Phe Glu Asp Met Cys Gly Arg Tyr Pro
        290                 295                 300

Asn Ala Thr Glu Val Asn Ile Ser Gly Val Pro Ala Val His Leu Leu
305                 310                 315                 320

Ala Met Lys Ala Val Ser Ser Leu Arg Asn Leu Glu Val Leu Thr Leu
                325                 330                 335

Gly Arg Gly Gln Leu Ala Asp Asn Phe Phe His Ala Leu Ala Asp Cys
            340                 345                 350

His Leu Leu Lys Ser Leu Thr Val Asn Asp Ser Thr Leu Val Asn Val
            355                 360                 365

Thr Gln Glu Ile Pro Ile Ser His Asp Gly Leu Arg His Leu His Leu
        370                 375                 380

Thr Lys Cys Arg Val Ile Arg Ile Ser Val Arg Cys Pro Gln Leu Glu
385                 390                 395                 400

Thr Leu Ser Leu Lys Arg Ser Asn Met Ala Gln Ala Val Leu Asn Cys
                405                 410                 415

Pro Leu Leu Arg Asp Leu Asp Ile Gly Ser Cys His Lys Leu Ser Asp
            420                 425                 430

Ala Ala Ile Arg Ser Ala Ala Ile Ser Cys Pro Gln Leu Glu Ser Leu
            435                 440                 445

Asp Met Ser Asn Cys Ser Cys Val Ser Asp Glu Thr Leu Arg Glu Ile
        450                 455                 460
```

-continued

```
Ser Gly Ser Cys Pro Asn Leu Gln Leu Leu Asn Ala Ser Tyr Cys Pro
465                 470                 475                 480

Asn Ile Ser Leu Glu Ser Val Arg Leu Thr Met Leu Thr Val Leu Lys
                485                 490                 495

Leu His Ser Cys Glu Gly Ile Thr Ser Ala Ser Met Thr Ala Ile Ser
                500                 505                 510

Asn Ser Ser Ser Leu Lys Val Leu Glu Leu Asp Asn Cys Ser Leu Leu
                515                 520                 525

Thr Ser Val Cys Leu Asp Leu Pro Asp Leu Gln Asn Ile Arg Leu Val
                530                 535                 540

His Cys Arg Lys Phe Ser Asp Leu Ser Leu Gln Ser Ile Lys Leu Ser
545                 550                 555                 560

Ser Ile Met Val Ser Asn Cys Pro Ser Leu His Arg Ile Asn Ile Thr
                565                 570                 575

Ser Asn Leu Leu Gln Lys Leu Val Leu Lys Lys Gln Glu Ser Leu Ala
                580                 585                 590

Lys Leu Ile Leu Gln Cys Pro Ser Leu Gln Asp Val Asp Leu Thr Asp
                595                 600                 605

Cys Glu Ser Leu Thr Asn Ser Leu Cys Glu Val Phe Ser Asp Gly Gly
                610                 615                 620

Gly Cys Pro Met Leu Lys Ser Leu Val Leu Asp Asn Cys Glu Ser Leu
625                 630                 635                 640

Thr Ala Val Arg Phe Cys Ser Ser Ser Leu Gly Ser Leu Ser Leu Val
                645                 650                 655

Gly Cys Arg Ala Ile Thr Ser Leu Glu Leu Gln Cys Pro Asn Leu Glu
                660                 665                 670

Lys Val Ser Leu Asp Gly Cys Asp Arg Leu Glu Arg Ala Ser Phe Ser
                675                 680                 685

Pro Val Gly Leu Arg Ser Leu Asn Leu Gly Ile Cys Pro Lys Leu Asn
                690                 695                 700

Glu Leu Lys Leu Glu Ala Pro His Met Asp Leu Leu Glu Leu Lys Gly
705                 710                 715                 720

Cys Gly Gly Leu Ser Glu Ala Ala Ile Asn Cys Pro Arg Leu Thr Ser
                725                 730                 735

Leu Asp Ala Ser Phe Cys Ser Gln Leu Lys Asp Glu Cys Leu Ser Ala
                740                 745                 750

Thr Thr Ala Ser Cys Pro Gln Ile Glu Ser Leu Ile Leu Met Ser Cys
                755                 760                 765

Pro Ser Val Gly Ser Glu Gly Leu Tyr Ser Leu Gln Cys Leu Leu Lys
                770                 775                 780

Leu Val Val Leu Asp Leu Ser Tyr Thr Phe Leu Leu Asn Leu Gln Pro
785                 790                 795                 800

Val Phe Glu Ser Cys Ile Gln Leu Lys Val Leu Lys Leu Gln Ala Cys
                805                 810                 815

Lys Tyr Leu Thr Asp Ser Ser Leu Glu Pro Leu Tyr Lys Glu Gly Ala
                820                 825                 830

Leu Pro Ala Leu Gln Glu Leu Asp Leu Ser Tyr Gly Thr Leu Cys Gln
                835                 840                 845

Ser Ala Ile Glu Glu Leu Leu Ala Cys Cys Thr His Leu Thr His Val
                850                 855                 860

Ser Leu Asn Gly Cys Val Asn Met His Asp Leu Asn Trp Gly Cys Ser
865                 870                 875                 880
```

-continued

```
Ile Gly Gln Leu Ser Leu Ser Gly Ile Pro Ile Pro Leu Gly Gln Ala
                885                 890                 895

Thr Phe Asp Glu Ile Glu Glu Pro Ile Ala Gln Pro Asn Arg Leu Leu
                900                 905                 910

Gln Asn Leu Asn Cys Val Gly Cys Gln Asn Ile Arg Lys Val Leu Ile
                915                 920                 925

Pro Pro Ala Ala Arg Cys Phe His Leu Ser Ser Leu Asn Leu Ser Leu
        930                 935                 940

Ser Ser Asn Leu Lys Glu Val Asp Val Ser Cys Tyr Asn Leu Cys Val
945                 950                 955                 960

Leu Asn Leu Ser Asn Cys Cys Ser Leu Glu Val Leu Lys Leu Asp Cys
                965                 970                 975

Pro Arg Leu Thr Asn Leu Phe Leu Gln Ser Cys Asn Ile Glu Glu Glu
                980                 985                 990

Val Val Val Ala Ala Val Ser Lys Cys Ser Met Leu Glu Thr Leu Asp
        995                 1000                1005

Val Arg Phe Cys Pro Lys Ile Ser Ser Ile Ser Met Val Gln Leu
        1010                1015                1020

Arg Ile Ala Cys Pro Ser Leu Lys Arg Ile Phe Ser Ser Leu Ser
        1025                1030                1035

Pro Thr
1040
```

```
<210> SEQ ID NO 3
<211> LENGTH: 1043
<212> TYPE: PRT
<213> ORGANISM: artificial
<220> FEATURE:
<223> OTHER INFORMATION: wild type melon WAP5.1 ortholog protein

<400> SEQUENCE: 3

Met Thr Ile Trp Cys Cys Leu Cys Phe Thr Val Gly Glu Glu Glu Glu
1               5                   10                  15

Glu Glu Asp Glu Arg Glu Arg Glu Glu Glu Val Lys Lys Glu Glu Gly
                20                  25                  30

Glu Met Lys Pro Met Met Arg Glu Glu Val Phe Glu Asn Gln Asp Asp
        35                  40                  45

Ser Asp Arg Ile Val Arg Asn Gly Asp Asp Ser Gln Gly Ser Asn Pro
        50                  55                  60

Leu Ala Ser Ala Val Asp Asp Val Pro Glu Arg His Gly Ser Asp Gln
65                  70                  75                  80

Leu Arg Leu Phe Glu Asp Met Val Arg Ala Met His Asp Gly Gly Asp
                85                  90                  95

Gly Gly Ala His Cys His Trp Asp Asp Glu Leu Arg Gly Gly Gly Ala
                100                 105                 110

Gly Gly Gly Val Ile Asn Pro Trp Asn Leu Ser Phe Gly Ile Met His
        115                 120                 125

Gln Ser Glu Gly Gly Glu Ser Ser Ser Ala Ser Ala Leu Pro Leu Ser
        130                 135                 140

Ser Met Ala Glu Thr Ser Ile Glu Glu Arg Asp Arg Asp Ala His His
145                 150                 155                 160

Lys Arg Ala Lys Val His Ser Lys Phe Ile Glu Ser Ser Phe Ala Thr
                165                 170                 175

Pro Trp Pro Leu Gly Ala Gly Asn Pro Met Arg Glu Phe Asp Phe Ile
                180                 185                 190
```

-continued

```
His Gly Ser Ser Ser Ile Met Ser Arg Asn Glu Phe Leu Tyr His Ala
        195             200             205

Ser Thr Ser Ser Arg Ile Asp Ala Asp Lys Asp Leu Glu Ser Ser Phe
        210             215             220

Gly Arg Asp Asp Gly Ile Asn Glu Asn Asp Thr Cys Lys Ser Glu Gly
225             230             235             240

Phe Glu Val Arg Met Asp Leu Thr Asp Leu Leu His Met Val Phe
                245             250             255

Ser Phe Leu Asp His Ile Asn Leu Cys Arg Ala Ala Ile Val Cys Arg
                260             265             270

Gln Trp Gln Ala Ala Ser Ala His Glu Asp Phe Trp Arg Cys Leu Asn
        275             280             285

Phe Glu Asn Arg Asn Ile Ser Met Glu Gln Phe Glu Asp Met Cys Gly
        290             295             300

Arg Tyr Pro Asn Ala Thr Glu Val Asn Ile Ser Gly Val Pro Ala Val
305             310             315             320

His Leu Leu Ala Met Lys Ala Val Ser Ser Leu Arg Asn Leu Glu Val
                325             330             335

Leu Thr Leu Gly Arg Gly Gln Leu Ala Asp Asn Phe Phe His Ala Leu
                340             345             350

Ala Asp Cys His Leu Leu Lys Ser Leu Thr Val Asn Asp Ser Thr Leu
        355             360             365

Val Asn Val Thr Gln Glu Ile Pro Ile Ser His Asp Arg Leu Arg His
        370             375             380

Leu His Leu Thr Lys Cys Arg Val Ile Arg Ile Ser Val Arg Cys Pro
385             390             395             400

Gln Leu Glu Thr Leu Ser Leu Lys Arg Ser Asn Met Ala Gln Ala Val
                405             410             415

Leu Asn Cys Pro Leu Leu Arg Asp Leu Asp Ile Gly Ser Cys His Lys
                420             425             430

Leu Ser Asp Ala Ala Ile Arg Ser Ala Ala Ile Ser Cys Pro Gln Leu
        435             440             445

Glu Ser Leu Asp Met Ser Asn Cys Ser Cys Val Ser Asp Glu Thr Leu
        450             455             460

Arg Glu Ile Ser Gly Ser Cys Pro Asn Leu Gln Leu Leu Asn Ala Ser
465             470             475             480

Tyr Cys Pro Asn Ile Ser Leu Glu Ser Val Arg Leu Thr Met Leu Thr
                485             490             495

Val Leu Lys Leu His Ser Cys Glu Gly Ile Thr Ser Ala Ser Met Thr
                500             505             510

Ala Ile Ser Asn Ser Ser Ser Leu Lys Val Leu Glu Leu Asp Asn Cys
        515             520             525

Ser Leu Leu Thr Ser Val Cys Leu Asp Leu Pro His Leu Gln Asn Ile
        530             535             540

Arg Leu Val His Cys Arg Lys Phe Ser Asp Leu Ser Leu Gln Ser Val
545             550             555             560

Lys Leu Ser Ser Ile Met Val Ser Asn Cys Pro Ser Leu His Arg Ile
                565             570             575

Asn Ile Thr Ser Asn Leu Leu Gln Lys Leu Val Leu Lys Lys Gln Glu
                580             585             590

Ser Leu Ala Lys Leu Val Leu Gln Cys Pro Ser Leu Gln Asp Val Asp
        595             600             605

Leu Thr Asp Cys Glu Ser Leu Thr Asn Ser Ile Cys Glu Val Phe Ser
```

```
        610             615             620

Asp Gly Gly Gly Cys Pro Met Leu Lys Ser Leu Val Leu Asp Asn Cys
625             630             635             640

Glu Ser Leu Thr Ala Val Arg Phe Cys Ser Ser Ser Leu Gly Ser Leu
                645             650             655

Ser Leu Val Gly Cys Arg Ala Ile Thr Ser Leu Glu Leu Gln Cys Pro
                660             665             670

Asn Leu Glu Gln Val Ser Leu Asp Gly Cys Asp His Leu Glu Arg Ala
                675             680             685

Ser Phe Ser Pro Val Gly Leu Arg Ser Leu Asn Leu Gly Ile Cys Pro
                690             695             700

Lys Leu Asn Glu Leu Lys Leu Glu Ala Pro Arg Met Asp Leu Leu Glu
705             710             715             720

Leu Lys Gly Cys Gly Gly Leu Ser Glu Ala Ala Ile Asn Cys Pro Arg
                725             730             735

Leu Thr Ser Leu Asp Ala Ser Phe Cys Gly Gln Leu Lys Asp Glu Cys
                740             745             750

Leu Ser Ala Thr Thr Ala Ser Cys Pro Gln Ile Glu Ser Leu Ile Leu
                755             760             765

Met Ser Cys Pro Ser Val Gly Ser Glu Gly Leu Tyr Ser Leu Arg Cys
770             775             780

Leu Leu Lys Leu Val Val Leu Asp Leu Ser Tyr Thr Phe Leu Met Asn
785             790             795             800

Leu Gln Pro Val Phe Glu Ser Cys Ile Gln Leu Lys Val Leu Lys Leu
                805             810             815

Gln Ala Cys Lys Tyr Leu Thr Asp Ser Ser Leu Glu Pro Leu Tyr Lys
                820             825             830

Glu Gly Ala Leu Pro Ala Leu Gln Glu Leu Asp Leu Ser Tyr Gly Thr
                835             840             845

Leu Cys Gln Ser Ala Ile Glu Glu Leu Leu Ala Cys Cys Thr His Leu
                850             855             860

Thr His Val Ser Leu Asn Gly Cys Val Asn Met His Asp Leu Asn Trp
865             870             875             880

Gly Cys Ser Ile Gly Gln Leu Ser Leu Ser Val Ile Pro Ile Pro Leu
                885             890             895

Gly Gln Ala Thr Phe Asp Glu Ile Glu Glu Pro Val Ala Gln Pro Asn
                900             905             910

Arg Leu Leu Gln Asn Leu Asn Cys Val Gly Cys Pro Asn Ile Arg Lys
                915             920             925

Val Leu Ile Pro Pro Ala Ala Arg Cys Phe His Leu Ser Ser Leu Asn
930             935             940

Leu Ser Leu Ser Ser Asn Leu Lys Glu Val Asp Val Ser Cys Tyr Asn
945             950             955             960

Leu Cys Phe Leu Asn Leu Ser Asn Cys Cys Ser Leu Glu Val Leu Lys
                965             970             975

Leu Asp Cys Pro Arg Leu Thr Ser Leu Phe Leu Gln Ser Cys Asn Ile
                980             985             990

Glu Glu Glu Val Val Val Ala Ala  Val Ser Lys Cys Ser  Met Leu Glu
                995             1000            1005

Thr Leu  Asp Val Arg Phe Cys  Pro Lys Ile Ser Ser  Ile Ser Met
    1010            1015            1020

Val Gln  Leu Arg Ile Ala Cys  Pro Ser Leu Lys Arg  Ile Phe Ser
    1025            1030            1035
```

```
Ser Leu  Ser Pro Thr
    1040

<210> SEQ ID NO 4
<211> LENGTH: 1033
<212> TYPE: PRT
<213> ORGANISM: artificial
<220> FEATURE:
<223> OTHER INFORMATION: Mutant wap5.1 protein with L528F substitution

<400> SEQUENCE: 4

Met Thr Ile Trp Cys Cys Leu Cys Phe Thr Val Gly Glu Glu Asp Glu
1               5                   10                  15

Arg Glu Arg Glu Glu Glu Leu Lys Lys Glu Gly Glu Met Lys Pro Met
                20                  25                  30

Met Arg Glu Glu Val Phe Glu Asn Gln Asp Asp Ser Asp Arg Ile Val
            35                  40                  45

Arg Asn Gly Asp Asp Ser Gln Gly Ser Asn Pro Leu Pro Ile Ala Val
    50                  55                  60

Asp Asp Ala Pro Asp Arg His Asp Gly Asp Arg Leu Arg Leu Phe Glu
65                  70                  75                  80

Asp Met Val Arg Ala Met His Asp Gly Ala Asp Gly Gly Gly Ala His
                85                  90                  95

Trp Asp Asp Glu Leu Arg Gly Gly Gly Gly Ala Ile Asn Pro Trp
                100                 105                 110

Asn Phe Ser Phe Gly Ile Leu His Gln Ser Glu Gly Gly Glu Ser Ser
            115                 120                 125

Ser Ala Ser Ala Leu Ser Leu Ser Ser Thr Val Glu Thr Ser Asn Glu
    130                 135                 140

Glu Arg Asp Arg Asp Ala Asn His Lys Arg Ala Lys Val Leu Ser Lys
145                 150                 155                 160

Phe Thr Glu Ser Ser Phe Ala Thr Pro Trp Pro Leu Gly Ala Gly Asn
                165                 170                 175

Pro Met Arg Asp Tyr Asp Phe Ile His Gly Ser Ser Ser Ile Met Ser
                180                 185                 190

Arg Asn Glu Phe Leu Tyr His Ala Ser Thr Ser Cys Arg Val Asp Glu
            195                 200                 205

Asp Leu Glu Ser Ser Phe Gly Arg Asp Asp Gly Ile Asn Asp Asn Asp
    210                 215                 220

Thr Cys Lys Ser Glu Gly Phe Glu Val Arg Met Asp Leu Thr Asp Asp
225                 230                 235                 240

Leu Leu His Met Val Phe Ser Phe Leu Asp His Ile Asn Leu Cys Arg
                245                 250                 255

Ala Ala Ile Val Cys Arg Gln Trp Gln Ala Ala Ser Ala His Glu Asp
                260                 265                 270

Phe Trp Arg Cys Leu Asn Phe Glu Asn Arg Asn Ile Ser Met Glu Gln
            275                 280                 285

Phe Glu Asp Met Cys Gly Arg Tyr Pro Asn Ala Thr Glu Val Asn Ile
    290                 295                 300

Ser Gly Val Pro Ala Val His Leu Leu Ala Met Lys Ala Val Ser Ser
305                 310                 315                 320

Leu Arg His Leu Glu Val Leu Thr Leu Gly Arg Gly Gln Leu Ala Asp
                325                 330                 335

Asn Phe Phe His Ala Leu Thr Asp Cys His Leu Leu Lys Ser Leu Thr
            340                 345                 350
```

-continued

```
Val Asn Asp Ser Thr Leu Val Asn Val Thr Gln Glu Ile Pro Ile Ser
        355                 360                 365

His Asp Arg Leu Arg His Leu His Leu Thr Lys Cys Arg Val Ile Arg
        370                 375                 380

Ile Ser Val Arg Cys Pro Gln Leu Glu Thr Leu Ser Leu Lys Arg Ser
385                 390                 395                 400

Asn Met Ala Gln Ala Val Leu Asn Cys Pro Leu Leu Arg Asp Leu Asp
                405                 410                 415

Ile Gly Ser Cys His Lys Leu Ser Asp Ala Ala Ile Arg Ser Ala Ala
                420                 425                 430

Ile Ser Cys Pro Gln Leu Glu Ser Leu Asp Met Ser Asn Cys Ser Cys
                435                 440                 445

Val Ser Asp Glu Thr Leu Arg Glu Ile Ser Ala Asn Cys Pro Asn Leu
        450                 455                 460

Gln Leu Leu Asn Ala Ser Tyr Cys Pro Asn Ile Ser Leu Glu Ser Val
465                 470                 475                 480

Arg Leu Thr Met Leu Thr Val Leu Lys Leu His Ser Cys Glu Gly Ile
                485                 490                 495

Thr Ser Ala Ser Met Thr Ala Ile Ser Ser Ser Ser Gly Leu Lys Val
                500                 505                 510

Leu Glu Leu Asp Asn Cys Ser Leu Leu Thr Ser Val Ser Leu Asp Phe
                515                 520                 525

Pro His Leu Gln Asn Ile Arg Leu Val His Cys Arg Lys Phe Ser Asp
        530                 535                 540

Leu Ser Leu Gln Ser Val Lys Leu Ser Ser Ile Met Val Ser Asn Cys
545                 550                 555                 560

Pro Ser Leu His Arg Ile Asn Ile Thr Ser Asn Leu Leu Gln Lys Leu
                565                 570                 575

Val Leu Lys Lys Gln Glu Ser Leu Ala Lys Leu Val Leu Gln Cys Pro
                580                 585                 590

Ser Leu Gln Asp Val Asp Leu Thr Asp Cys Glu Ser Leu Thr Asn Ser
        595                 600                 605

Ile Cys Glu Val Phe Ser Asp Gly Gly Gly Cys Pro Met Leu Lys Ser
        610                 615                 620

Leu Val Leu Asp Asn Cys Glu Ser Leu Thr Ala Val Arg Phe Cys Ser
625                 630                 635                 640

Ser Ser Leu Gly Ser Leu Ser Leu Val Gly Cys Arg Ala Ile Thr Ser
                645                 650                 655

Leu Glu Leu Gln Cys Pro Asn Leu Glu Gln Val Ser Leu Asp Gly Cys
                660                 665                 670

Asp His Leu Glu Arg Ala Ser Phe Ser Pro Val Gly Leu Arg Ser Leu
        675                 680                 685

Asn Leu Gly Ile Cys Pro Lys Leu Asn Glu Leu Lys Leu Glu Ala Pro
        690                 695                 700

Arg Met Asp Leu Leu Glu Leu Lys Gly Cys Gly Gly Leu Ser Glu Ala
705                 710                 715                 720

Ala Ile Asn Cys Pro Arg Leu Thr Ser Leu Asp Ala Ser Phe Cys Gly
                725                 730                 735

Gln Leu Lys Asp Glu Cys Leu Ser Ala Thr Thr Ala Ser Cys Pro Gln
                740                 745                 750

Ile Glu Ser Leu Ile Leu Met Ser Cys Pro Ser Val Gly Ser Glu Gly
        755                 760                 765
```

-continued

```
Leu Tyr Ser Leu Arg Cys Leu Leu Lys Leu Val Val Leu Asp Leu Ser
    770                 775                 780

Tyr Thr Phe Leu Met Ser Leu Gln Pro Val Phe Glu Ser Cys Ile Gln
785                 790                 795                 800

Leu Lys Val Leu Lys Leu Gln Ala Cys Lys Tyr Leu Thr Asp Ser Ser
                805                 810                 815

Leu Glu Pro Leu Tyr Lys Glu Asp Ala Leu Pro Ala Leu Gln Glu Leu
                820                 825                 830

Asp Leu Ser Tyr Gly Thr Leu Cys Gln Ser Ala Ile Glu Glu Leu Leu
                835                 840                 845

Ala Cys Cys Thr His Leu Thr His Val Ser Leu Asn Gly Cys Val Asn
    850                 855                 860

Met His Asp Leu Asn Trp Gly Cys Ser Ile Gly Gln Leu Ser Leu Ser
865                 870                 875                 880

Ser Ile Pro Ile Pro Leu Gly Gln Ala Thr Leu Asp Glu Ile Glu Glu
                885                 890                 895

Pro Val Ala Gln Pro Asn Arg Leu Leu Gln Asn Leu Asn Cys Val Gly
                900                 905                 910

Cys Gln Asn Ile Arg Lys Val Leu Ile Pro Pro Ala Ala Arg Cys Phe
                915                 920                 925

His Leu Ser Ser Leu Asn Leu Ser Leu Ser Ser Asn Leu Lys Glu Val
    930                 935                 940

Asp Val Ser Cys Tyr Asn Leu Cys Phe Leu Asn Leu Ser Asn Cys Cys
945                 950                 955                 960

Ser Leu Glu Val Leu Lys Leu Asp Cys Pro Arg Leu Thr Ser Leu Phe
                965                 970                 975

Leu Gln Ser Cys Asn Ile Glu Glu Glu Val Val Val Ala Ala Val Ser
                980                 985                 990

Arg Cys Ser Met Leu Glu Thr Leu  Asp Val Arg Leu Cys  Pro Lys Ile
                995                 1000                1005

Ser Ser  Ile Ser Met Val Gln  Leu Arg Ile Ala Cys  Pro Ser Leu
    1010                1015                1020

Lys Arg  Ile Phe Ser Thr Leu  Ser Pro Thr
    1025                1030
```

```
<210> SEQ ID NO 5
<211> LENGTH: 3102
<212> TYPE: DNA
<213> ORGANISM: artificial
<220> FEATURE:
<223> OTHER INFORMATION: cDNA encoding mutant wap5.1 protein of
      SEQ ID NO: 4

<400> SEQUENCE: 5
atgacgattt ggtgctgctt atgcttcacc gttggagaag aagacgaaag ggaaagggaa      60
gaggaactga agaaggaagg tgaaatgaaa cccatgatgc gtgaggaggt ttttgagaac     120
caggatgact ctgatcgcat tgtgcgaaat ggtgatgatt ctcaagggag taatccactt     180
ccgattgctg tagatgatgc gcctgaccgt catgacggtg atcgacttag actgtttgag     240
gatatggtca gagcaatgca cgatggcgcc gatggtggtg tgctcattgg gacgatgag     300 ctgcgcggcg gcggcggcgg ggctattaat ccctggaatt tttcttttgg aattctgcat     360
caatctgagg gaggagaaag tagtagcgcc tcggctttgt ccttgtcttc tacggtggag     420
acttctaatg aggaacgcga tcgggatgcc aaccataagc gcgctaaagt tctctccaaa     480
ttcactgaga gctcatttgc aactccatgg cctttgggtg ctggaaatcc tatgagagat     540
```

-continued

```
tatgatttta ttcacggatc atcttcaatt atgagtagga atgaatttct ataccatgct    600
tctacatcat gcagagttga cgaagatttg gaatctagtt ttggtagaga tgatgggatc    660
aatgataatg acacctgtaa atcagaagga tttgaagtaa gaatggatct tacagatgat    720
ttactgcata tggtgttctc tttcttggat cacatcaatc tttgtcgagc tgctatagtc    780
tgcaggcagt ggcaagctgc tagtgctcat gaagatttct ggaggtgttt gaattttgaa    840
aataggaaca tatccatgga acaattcgag gatatgtgtg gaagatatcc aaatgctaca    900
gaggtcaata tctctggtgt acctgccgtt cacttgcttg ccatgaaagc agtttcttct    960
ttaagacatc tggaggtttt aactctgggg agaggacaac tggcagataa cttttttcac   1020
gccctgactg attgccattt attgaagagt ttgactgtca atgattctac gctggttaat   1080
gttacacaag agatacctat aagccatgat agactgcgtc atcttcatct tactaaatgt   1140
cgtgttatac gcatatctgt tagatgtcca caacttgaaa cattgtcgtt gaagcgcagc   1200
aacatggcac aggctgttct taactgcccc cttcttcggg acctggatat aggctcttgc   1260
cacaagctct cagatgctgc aattcgctca gccgctattt catgcccaca gttggaatct   1320
cttgatatgt ctaattgttc atgtgttagt gatgagacat tacgtgaaat ttctgcaaac   1380
tgcccgaatc tccagcttct gaatgcatca tactgcccaa atatatcttt ggagtctgta   1440
agactgacaa tgctgaccgt gcttaagctt cacagctgtg agggcatcac atcagcttca   1500
atgaccgcaa tatctagtag ttctggtttg aaggttttgg agcttgataa ttgcagtctt   1560
ttgacttctg tttctctgga ttttccccat ttacagaata tcagacttgt tcattgccgc   1620
aaattctcag acttgagttt acagagtgtt aaattatcat ccataatggt ctctaattgt   1680
ccatcacttc atcggatcaa catcacttcc aatttacttc aaaaattggt gttgaagaaa   1740
caagagagct tggccaaatt ggttttgcag tgccctagtc tgcaagatgt ggacctcaca   1800
gactgtgaat cgctaacgaa ttctatttgt gaggttttta gtgatggtgg tggatgccct   1860
atgttgaaat cacttgttct tgataactgt gagagtctga ctgctgttcg attctgtagc   1920
agttctttag gcagtctttc ccttgttggt tgccgggcaa tcacttcact tgaacttcaa   1980
tgccctaatc tcgaacaggt ttctttagat ggctgtgatc atcttgagag agcatcattt   2040
tccccggttg gtctgcggtc actaaacctg ggaatctgtc ccaaattgaa tgaattaaaa   2100
cttgaggccc ctcggatgga tttacttgag ttaaaaggtt gtggtggatt gtctgaagca   2160
gccatcaatt gtcctcgtct aacatcgttg gatgcttcct tttgtggcca actgaaagat   2220
gagtgtttgt ctgcgactac tgcctcatgt ccacagattg agtcgttaat actgatgtca   2280
tgtccatcgg ttggttcaga ggggctttac tctctgcgat gccttctgaa gttggttgtg   2340
ctcgatttat catatacctt tttgatgagc ttgcagccag tcttcgagtc ttgtatacaa   2400
cttaaggtat tgaaactaca agcatgcaag tatttaactg actcatcgct agagcctctt   2460
tataaggaag acgctcttcc agctcttcaa gagttagact tatcttacgg gactctttgt   2520
cagtctgcca tagaagagct tcttgcttgt tgcactcact taactcatgt gagcttaaat   2580
gggtgtgtga acatgcatga tctaaattgg ggttgtagca ttggacagct ttcgttgtcc   2640
agcatcccaa ttcctcttgg tcaggccact cttgatgaga ttgaggaacc agttgcacag   2700
ccaaaccgtt tgttacagaa ccttaactgt gtaggttgtc agaatattag aaaggttctc   2760
attcctccag ctgctcgttg tttttcattta tcatcattaa acctatcctt gtcttcaaat   2820
ctcaaggaag ttgacgtctc ttgttacaac ctatgctttc ttaatttgag taattgctgc   2880
```

-continued

```
tctttggaag ttctaaaact tgactgcccg cggttaacca gtctctttct tcagtcttgc      2940
aacattgaag aagaagtggt tgtggctgcg gtatcgagat gtagcatgct cgagacgttg      3000
gatgtccgct tatgtccaaa gatctcctct attagcatgg tacaactgcg tattgcttgt      3060
ccaagtttga agcggatctt cagcactctg tctccaacat ga                        3102

<210> SEQ ID NO 6
<211> LENGTH: 3102
<212> TYPE: DNA
<213> ORGANISM: artificial
<220> FEATURE:
<223> OTHER INFORMATION: cDNA encoding wild type WAP5.1 protein of
     SEQ ID NO: 1

<400> SEQUENCE: 6
atgacgattt ggtgctgctt atgcttcacc gttggagaag aagacgaaag ggaaagggaa        60
gaggaactga agaaggaagg tgaaatgaaa cccatgatgc gtgaggaggt ttttgagaac       120
caggatgact ctgatcgcat tgtgcgaaat ggtgatgatt ctcaagggag taatccactt       180
ccgattgctg tagatgatgc gcctgaccgt catgacggtg atcgacttag actgtttgag       240
gatatggtca gagcaatgca cgatggcgcc gatggtggtg gtgctcattg ggacgatgag       300
ctgcgcggcg gcggcggcgg ggctattaat ccctggaatt tttcttttgg aattctgcat       360
caatctgagg gaggagaaag tagtagcgcc tcggctttgt ccttgtcttc tacggtggag       420
acttctaatg aggaacgcga tcgggatgcc aaccataagc gcgctaaagt tctctccaaa       480
ttcactgaga gctcatttgc aactccatgg cctttgggtg ctggaaatcc tatgagagat       540
tatgatttta ttcacggatc atcttcaatt atgagtagga atgaatttct ataccatgct       600
tctacatcat gcagagttga cgaagatttg gaatctagtt ttggtagaga tgatgggatc       660
aatgataatg acacctgtaa atcagaagga tttgaagtaa gaatggatct tacagatgat       720
ttactgcata tggtgttctc tttcttggat cacatcaatc tttgtcgagc tgctatagtc       780
tgcaggcagt ggcaagctgc tagtgctcat gaagatttct ggaggtgttt gaattttgaa       840
aataggaaca tatccatgga acaattcgag gatatgtgtg gaagatatcc aaatgctaca       900
gaggtcaata tctctggtgt acctgccgtt cacttgcttg ccatgaaagc agtttcttct       960
ttaagacatc tggaggtttt aactctgggg agaggacaac tggcagataa cttttttcac      1020
gccctgactg attgccattt attgaagagt ttgactgtca atgattctac gctggttaat      1080
gttacacaag atacctat aagccatgat agactgcgtc atcttcatct tactaaatgt        1140
cgtgttatac gcatatctgt tagatgtcca caacttgaaa cattgtcgtt gaagcgcagc      1200
aacatggcac aggctgttct taactgcccc cttcttcggg acctggatat aggctcttgc      1260
cacaagctct cagatgctgc aattcgctca gccgctattt catgcccaca gttggaatct      1320
cttgatatgt ctaattgttc atgtgttagt gatgagacat acgtgaaat ttctgcaaac       1380 tgcccgaatc tccagcttct gaatgcatca tactgcccaa atatatcttt ggagtctgta      1440
agactgacaa tgctgaccgt gcttaagctt cacagctgtg agggcatcac atcagcttca      1500
atgaccgcaa tatctagtag ttctggtttg aaggttttgg agcttgataa ttgcagtctt      1560
ttgacttctg tttctctgga tcttcccat ttacagaata tcagacttgt tcattgccgc       1620
aaattctcag acttgagttt acagagtgtt aaattatcat ccataatggt ctctaattgt      1680
ccatcacttc atcggatcaa catcacttcc aatttacttc aaaaattggt gttgaagaaa      1740
caagagagct tggccaaatt ggttttgcag tgccctagtc tgcaagatgt ggacctcaca      1800
```

-continued

```
gactgtgaat cgctaacgaa ttctatttgt gaggtttta gtgatggtgg tggatgccct    1860
atgttgaaat cacttgttct tgataactgt gagagtctga ctgctgttcg attctgtagc    1920
agttctttag gcagtctttc ccttgttggt tgccgggcaa tcacttcact tgaacttcaa    1980
tgccctaatc tcgaacaggt ttctttagat ggctgtgatc atcttgagag agcatcattt    2040
tccccggttg gtctgcggtc actaaacctg ggaatctgtc ccaaattgaa tgaattaaaa    2100
cttgaggccc ctcggatgga tttacttgag ttaaaaggtt gtggtggatt gtctgaagca    2160
gccatcaatt gtcctcgtct aacatcgttg gatgcttcct tttgtggcca actgaaagat    2220
gagtgtttgt ctgcgactac tgcctcatgt ccacagattg agtcgttaat actgatgtca    2280
tgtccatcgg ttggttcaga ggggctttac tctctgcgat gccttctgaa gttggttgtg    2340
ctcgatttat catatacctt tttgatgagc ttgcagccag tcttcgagtc ttgtatacaa    2400
cttaaggtat tgaaactaca agcatgcaag tatttaactg actcatcgct agagcctctt    2460
tataaggaag acgctcttcc agctcttcaa gagttagact tatcttacgg gactctttgt    2520
cagtctgcca tagaagagct tcttgcttgt tgcactcact taactcatgt gagcttaaat    2580
gggtgtgtga acatgcatga tctaaattgg ggttgtagca ttggacagct ttcgttgtcc    2640
agcatcccaa ttcctcttgg tcaggccact cttgatgaga ttgaggaacc agttgcacag    2700
ccaaaccgtt tgttacagaa ccttaactgt gtaggttgtc agaatattag aaaggttctc    2760
attcctccag ctgctcgttg tttttcattta tcatcattaa acctatcctt gtcttcaaat    2820
ctcaaggaag ttgacgtctc ttgttacaac ctatgctttc ttaatttgag taattgctgc    2880
tctttggaag ttctaaaact tgactgcccg cggttaacca gtctctttct tcagtcttgc    2940
aacattgaag aagaagtggt tgtggctgcg gtatcgagat gtagcatgct cgagacgttg    3000
gatgtccgct tatgtccaaa gatctcctct attagcatgg tacaactgcg tattgcttgt    3060
ccaagtttga agcggatctt cagcactctg tctccaacat ga                      3102
```

<210> SEQ ID NO 7
<211> LENGTH: 6896
<212> TYPE: DNA
<213> ORGANISM: artificial
<220> FEATURE:
<223> OTHER INFORMATION: genomic DNA of wild type WAP5.1 gene

<400> SEQUENCE: 7

```
atgacgattt ggtgctgctt atgcttcacc gttggagaag aagacgaaag ggaaagggaa      60
gaggaactga agaaggaagg tgaaatgaaa cccatgatgc gtgaggaggt tttttgagaac    120 caggatgact ctgatcgcat tgtgcgaaat ggtgatgatt ctcaagggag taatccactt    180
ccgattgctg tagatgatgc gcctgaccgt catgacggtg atcgacttag actgtttgag    240
gatatggtca gagcaatgca cgatggcgcc gatggtggtg gtgctcattg ggacgatgag    300
ctgcgcggcg gcggcggcgg ggctattaat ccctggaatt tttcttttgg aattctgcat    360
caatctgagg gaggagaaag tagtagcgcc tcggctttgt ccttgtcttc tacggtggag    420
acttctaatg aggaacgcga tcgggatgcc aaccataagc gcgctaaagt tctctccaaa    480
ttcacgtgag tcacttgtag actgcttctg gatatgaatt atgctaaggt ttcatgggtt    540
tgccattttt cttggttttc ttttcccct tttccgaaag gggtgttggt tttttttttt    600
tttttttttt tttcttgttc cttcttaaat gttctctctt tgtgggattt aggactagat    660
attgtggtgg tttttggatg gagatcgtta gcatttattg aggttatcat ttacgaatat    720
gcagggttct ttgtaattta gctatcaatg caggctgttt gttgttattt ttgtgccggc    780
```

-continued

```
atctctgaat aatttgctgt tttgcactgc aagatagcta tggaaaatta cgtattttat      840
gatctaaacg tgctccgctt ctttagctct cgggctgtat cagcgtttgg aaagtagttg      900
ttctatagat tttcacgagc accttctatt cttgaatact tgaagtggtg tctaatataa      960
agcaatatgt ttttgcatcg accttatccc gtccatcttt attgtatgta ttagactgtt     1020
ggcaggctct ttatcattgt attttaaata ttttttcccg atttctaaat tagaaatgtg     1080
tttcttaatc aatagtggca tgttgcttgg gcttttctag aagagatatc atacggtgtg     1140
ccaagatgat atctcaaagt cttcttcagt tgcgagtctt ctgagtgagt tgtcaccatg     1200
gaaaagtttc cttttcttca tggaatagaa aatcatttat atttgagaaa ttcaatatat     1260
ggttttcttt ctctgagaag agtttgaaaa tgaaagtat agatatgaat gtttattgtt      1320
tttgattgtc ttattaattg ttttttttgaa gcaaaccttc atgtacaacg atatttaggg     1380
tgtttgaatg cacataggtt ctcctattac atgatttatt tatgtactga aaattaaagg     1440
tgtattaaat ttgagtcata attttttgtaa aaactattct ttctaaattg ttttctggat     1500
atgcccaaac aagtccttat attttcaagc actgttgacc ttggtagtat agttatcaca     1560
ctcatttgca aacctacttg tgatactata ctttcattac tagttaaaaa aatgtcttcg     1620
ttaaggttta tcatggaggg atgagtatat agctgttgtc ttactgctaa atatgatctt     1680
atgttggaaa ctctgcccct cacatggtgg ttgatgatgt atcatgtgat ctttagttta     1740
aaaaagagta aactctgagt taactaaatg taagtatgtg cagtaatact cattccagat     1800
aattcacatt ctctcaaccg tttagatctt gcaaattagc accatcaagt ttcctataat     1860
ttacaagtta gactaactga taagtgtaaa gttagaaatg atgctcgtta ttcactttta     1920
acaattgttt cttattttct tttctttttca atcttcccta gtgagagctc atttgcaact     1980
ccatggcctt tgggtgctgg aaatcctatg agagattatg attttattca cggatcatct     2040
tcaattatga gtaggaatga atttctatac catgcttcta catcatgcag agttgacgaa     2100
gatttggaat ctagttttgg tagagatgat gggatcaatg ataatgacac ctgtaaatca     2160
gaaggatttg aagtaagaat ggatcttaca gatgatttac tgcatatggt atgcatctcc     2220
agagatttat tattgttttc ttgcttaccg tcttatttct tggatttctt attcacatga     2280
agttaaatta attgatatca ggtgttctct ttcttggatc acatcaatct ttgtcgagct     2340
gctatagtct gcaggcagtg gcaagctgct agtgctcatg aagatttctg gaggtgtttg     2400
aattttgaaa ataggaacat atccatggaa caatgtaggt gttgttctgc ttcttccttt     2460 catttttctag agtagttgag acaagaatga ggtgatttta aaaatgttgg ttgcctcttg     2520
gaaatagagg tgatatatta tgatgtaact tcaaaacatg taggatgcag tatttgagtc     2580
tggaatgtct ttagcactca tgaaatgttg ttaaaagcct aggactgcga catatttggg     2640
gcttgttttc agtactcagt aggattttc tccctaaatc tttttgacta ggtatgtata     2700
taatattaaa ggaaagaact tcttgatgct attttttagct ttggcaatct cttgattctt     2760
ttaaaataag ttctggatat aattgtataa atgtgatagg atgtgacata tctctgtagc     2820
agtcttggtg ccagtgccaa tgcaacactt tcaatcgtat ttcaagttta acctactttt     2880
atccagtcac attttctttc tacccaccat acagtataaa ttgatccggt tgtatttctt     2940
tgtgcctctg tattaacaac tgtcctatcc tattctatgt tgcttactttt ctaacatcat     3000 tctgatttgg agctagttag ttaattgatt aattctgact gcagtcgagg atatgtgtgg     3060
aagatatcca aatgctacag aggtcaatat ctctggtgta cctgccgttc acttgcttgc     3120
```

```
catgaaagca gtttcttctt taaggtaatg attacggttt tgtatttttg ttttttttcc    3180
tcatcctgaa tctttatggt ggtgcttatt attttattat tgtctcagac atctggaggt    3240
tttaactctg gggagaggac aactggcaga taactttttt cacgccctga ctgattgcca    3300
tttattgaag agtttgactg tcaatgattc tacgctggtt aatgttacac aagagatacc    3360
tataagccat gatagactgc gtcatcttca tcttactaaa tgtcgtgtta tacgcatatc    3420
tgttaggttg ctaatgttta tgtatcttaa tgctaactgt atttaattgt ttagtttgtt    3480
tttttttttt tttggtctaa agcatgtttt cttgcagatg tccacaactt gaaacattgt    3540
cgttgaagcg cagcaacatg gcacaggctg ttcttaactg cccccttctt cgggacctgg    3600
atataggctc ttgccacaag ctctcagatg ctgcaattcg ctcagccgct atttcatgcc    3660
cacagttgga atctcttgat atgtctaatt gttcatgtgt tagtgatgag acattacgtg    3720
aaatttctgc aaactgcccg aatctccagc ttctgaatgc atcatactgc ccaaatatat    3780
ctttggaggt ggcataccat ttttagttaa attttgagcg aaagtgacta ttttgccctt    3840
cagacttgtt tttcctgata ttttggttcc tttttctttt gaagtctgta agactgacaa    3900
tgctgaccgt gcttaagctt cacagctgtg agggcatcac atcagcttca atgaccgcaa    3960
tatctagtag ttctggtttg aaggtctgaa ataacctatt tcgactgttt atattttcta    4020
gttgtctggt gctgtgtctg agttagttga aaatggaatg gagacttatt gcaggttttg    4080
gagcttgata attgcagtct tttgacttct gtttctctgg atcttcccca tttacagaat    4140
atcagacttg ttcattgccg caagtatgtc ttctcatctc caagcaactc atagcttcta    4200
tcacatgatt aatttcattt agaaggactt ttgaactggg ccttcacttc ttttttcctt    4260
gagttgaatc tgtttcgcca ttcttgcaga ttctcagact tgagtttaca gagtgttaaa    4320
ttatcatcca taatggtctc taattgtcca tcacttcatc ggatcaacat cacttccaat    4380
ttacttcaag tatgtcgtaa tggatcttaa agtttcttt cttattaatt tcatttcata    4440
agggtataaa cgaacattgg actgtacttt tgtggacttg cagaaattgg tgttgaagaa    4500
acaagagagc ttggccaaat tggttttgca gtgccctagt ctgcaagatg tggacctcac    4560
agactgtgaa tcgctaacga attctatttg tgaggttttt agtgatggtg gtggatgccc    4620
tatgttgaaa tcacttgttc ttgataactg tgaggtaagt agcttggtgt tacccatcag    4680
tatcatcgca ttggcccttg tgatttcata atttggaaat tatttgattg agactttcca    4740
ttgatttcta atgtgaacat gtttcttttg ttcagagtct gactgctgtt cgattctgta    4800
gcagttcttt aggcagtctt tcccttgttg gttgccgggc aatcacttca cttgaacttc    4860
aatgccctaa tctcgaacag gtttctttag atggctgtga tcatcttgag agagcatcat    4920
tttccccggt atgtgaaaac tgacaacttg taaatttttc tcagtcacta tattataaat    4980
attctcctta gcgctaaaga ttgggctttt ttctctcttt tttaaggttg gtctgcggtc    5040
actaaacctg ggaatctgtc ccaaattgaa tgaattaaaa cttgaggccc ctcggatgga    5100
tttacttgag ttaaaaggtt gtggtggatt gtctgaagca gccatcaatt gtcctcgtct    5160
aacatcgttg gatgcttcct tttgtgggtt agtttgttat gattatttgg atgacacctt    5220
ctatttgatg gatactggtt gcttatgtcg ttgagttctt ctttttccct tgcagccaac    5280
tgaaagatga gtgtttgtct gcgactactg cctcatgtcc acagattgag tcgttaatac    5340
tgatgtcatg tccatcggtt ggttcagagg ggctttactc tctgcgatgc cttctgaagt    5400
tggttgtgct cgatttatca tatacctttt tgatgagctt gcagccagtc ttcgagtctt    5460
gtatacaact taaggtacct ttttgataga tattatcatg acccctgtct gatttctgtt    5520
```

```
gtattgatgc cttcttcttt gtgttcttaa tgaaggtatt gaaactacaa gcatgcaagt      5580
atttaactga ctcatcgcta gagcctcttt ataaggaaga cgctcttcca gctcttcaag      5640
agttagactt atcttacggg actctttgtc agtctgccat agaagagctt cttgcttgtt      5700
gcactcactt aactcatgtg agcttaaatg ggtgtgtgaa catgcatgat ctaaattggg      5760
gttgtagcat tggacagctt tcgttgtcca gcatcccaat tcctcttggt caggccactc      5820
ttgatgagat tgaggaacca gttgcacagc caaaccgttt gttacagaac cttaactgtg      5880
taggttgtca gaatattaga aaggttctca ttcctccagc tgctcgttgt tttcatttat      5940
catcattaaa cctatccttg tcttcaaatc tcaaggaagt tgacgtctct tgttacaacc      6000
tatgctttct taatttgagg ttatgccccc ctaccctttt gctccattaa caattttagt      6060
tggttccttt ctttttttttt tttttggcct accctgctaa atccgtgttt ttgtgatcta      6120
gtaattgctg ctctttggaa gttctaaaac ttgactgccc gcggttaacc agtctctttc      6180
ttcaggtaat tttttcttca atgtaagttt tggatgttca tactaatcta ctctgaatag      6240
tccagaatct ggtcttccaa gcaatccgaa actaaccgtt ggggataggg tggacaaaaa      6300
atggggtcaa gacagattac aacgcacaag tccacattat aaggacccag tcaatgactg      6360
gagttgaact cccaacctga dacccccctg tagggctgta ggcctcgggt ctaaggaccc      6420
caattttgtt tgcatccccc tccactttta acctttttttt tttttttttt ttttgggata      6480
ggaattcatc cattgttgga atcatttgat tatagtttat tttttatctt attttttact      6540
gttgtgttgg gtaaacaata ctttggtttc aaacttgaga aaaaaagaaa tggcagctaa      6600
gagatgcata tgaattttat gatatgaggc taactagatc tgtctttttcc tagtcttgca      6660 acattgaaga agaagtggtt gtggctgcgg tatcgagatg tagcatgctc gagacgttgg      6720
atgtccgctt atgtccaaag gtgaggggtg tctctctttt cctctacatt gtttgatagt      6780
tttggctgac ttcataatat ttcttctact ggcagatctc ctctattagc atggtacaac      6840
tgcgtattgc ttgtccaagt ttgaagcgga tcttcagcac tctgtctcca acatga         6896
```

```
<210> SEQ ID NO 8
<211> LENGTH: 121
<212> TYPE: DNA
<213> ORGANISM: artificial
<220> FEATURE:
<223> OTHER INFORMATION: marker mwm23348429 to detect mutant allele
      encoding L528F mutant wap5.1 protein
<220> FEATURE:
<221> NAME/KEY: C/T SNP
<222> LOCATION: (61)..(61)

<400> SEQUENCE: 8
gacttattgc aggttttgga gcttgataat tgcagtcttt tgacttctgt ttctytggat        60
tttccccatt tacagaatat cagacttgty cattgccgca agtatgtctt ctcatctcca       120
a                                                                        121

<210> SEQ ID NO 9
<211> LENGTH: 1033
<212> TYPE: PRT
<213> ORGANISM: Citrullus lanatus

<400> SEQUENCE: 9

Met Thr Ile Trp Cys Cys Leu Cys Phe Thr Val Gly Glu Glu Asp Glu
1               5                   10                  15

Arg Glu Arg Glu Glu Glu Leu Lys Lys Glu Gly Glu Met Lys Pro Met
```

-continued

```
                20              25              30

Met Arg Glu Glu Val Phe Glu Asn Gln Asp Asp Ser Asp Arg Ile Val
            35              40              45

Arg Asn Arg Asp Asp Ser Gln Gly Ser Asn Pro Leu Pro Ile Ala Val
        50              55              60

Asp Asp Ala Pro Asp Arg His Asp Gly Asp Arg Leu Arg Leu Phe Glu
65              70              75              80

Asp Met Val Arg Ala Met His Asp Gly Ala Asp Gly Gly Gly Ala His
                85              90              95

Trp Asp Asp Glu Leu Arg Gly Gly Gly Gly Ala Ile Asn Pro Trp
            100             105             110

Asn Phe Ser Phe Gly Ile Leu His Gln Ser Glu Gly Gly Glu Ser Ser
        115             120             125

Ser Ala Ser Ala Leu Ser Leu Ser Ser Thr Val Glu Thr Ser Asn Glu
        130             135             140

Glu Arg Asp Arg Asp Ala Asn His Lys Arg Ala Lys Val Leu Ser Lys
145             150             155             160

Phe Thr Glu Ser Ser Phe Ala Thr Pro Trp Pro Leu Gly Ala Gly Asn
                165             170             175

Pro Met Arg Asp Tyr Asp Phe Ile His Gly Ser Ser Ser Ile Met Ser
                180             185             190

Arg Asn Glu Phe Leu Tyr His Ala Ser Thr Ser Cys Arg Val Asp Glu
                195             200             205

Asp Leu Glu Ser Ser Phe Gly Arg Asp Asp Gly Ile Asn Asp Asn Asp
        210             215             220

Thr Cys Lys Ser Glu Gly Phe Glu Val Arg Met Asp Leu Thr Asp Asp
225             230             235             240

Leu Leu His Met Val Phe Ser Phe Leu Asp His Ile Asn Leu Cys Arg
                245             250             255

Ala Ala Ile Val Cys Arg Gln Trp Gln Ala Ala Ser Ala His Glu Asp
                260             265             270

Phe Trp Arg Cys Leu Asn Phe Glu Asn Arg Asn Ile Ser Met Glu Gln
                275             280             285

Phe Glu Asp Met Cys Gly Arg Tyr Pro Asn Ala Thr Glu Val Asn Ile
        290             295             300

Ser Gly Val Pro Ala Val His Leu Leu Ala Met Lys Ala Val Ser Ser
305             310             315             320

Leu Arg His Leu Glu Val Leu Thr Leu Gly Arg Gly Gln Leu Ala Asp
                325             330             335

Asn Phe Phe His Ala Leu Thr Asp Cys His Leu Leu Lys Ser Leu Thr
                340             345             350

Val Asn Asp Ser Thr Leu Val Asn Val Thr Gln Glu Ile Pro Ile Ser
                355             360             365

His Asp Arg Leu Arg His Leu His Leu Thr Lys Cys Arg Val Ile Arg
        370             375             380

Ile Ser Val Arg Cys Pro Gln Leu Glu Thr Leu Ser Leu Lys Arg Ser
385             390             395             400

Asn Met Ala Gln Ala Val Leu Asn Cys Pro Leu Leu Arg Asp Leu Asp
                405             410             415

Ile Gly Ser Cys His Lys Leu Ser Asp Ala Ala Ile Arg Ser Ala Ala
                420             425             430

Ile Ser Cys Pro Gln Leu Glu Ser Leu Asp Met Ser Asn Cys Ser Cys
                435             440             445
```

```
Val Ser Asp Glu Thr Leu Arg Glu Ile Ser Ala Asn Cys Pro Asn Leu
    450             455             460

Gln Leu Leu Asn Ala Ser Tyr Cys Pro Asn Ile Ser Leu Glu Ser Val
465             470             475             480

Arg Leu Thr Met Leu Thr Val Leu Lys Leu His Ser Cys Glu Gly Ile
            485             490             495

Thr Ser Ala Ser Met Thr Ala Ile Ser Ser Ser Gly Leu Lys Val
            500             505             510

Leu Glu Leu Asp Asn Cys Ser Leu Leu Thr Ser Val Ser Leu Asp Leu
        515             520             525

Pro His Leu Gln Asn Ile Arg Leu Val His Cys Arg Lys Phe Ser Asp
    530             535             540

Leu Ser Leu Gln Ser Val Lys Leu Ser Ser Ile Met Val Ser Asn Cys
545             550             555             560

Pro Ser Leu His Arg Ile Asn Ile Thr Ser Asn Leu Leu Gln Lys Leu
            565             570             575

Val Leu Lys Lys Gln Glu Ser Leu Ala Lys Leu Val Leu Gln Cys Pro
            580             585             590

Ser Leu Gln Asp Val Asp Leu Thr Asp Cys Glu Ser Leu Thr Asn Ser
        595             600             605

Ile Cys Glu Val Phe Ser Asp Gly Gly Gly Cys Pro Met Leu Lys Ser
    610             615             620

Leu Val Leu Asp Asn Cys Glu Ser Leu Thr Ala Val Arg Phe Cys Ser
625             630             635             640

Ser Ser Leu Gly Ser Leu Ser Leu Val Gly Cys Arg Ala Ile Thr Ser
            645             650             655

Leu Glu Leu Gln Cys Pro Asn Leu Glu Gln Val Ser Leu Asp Gly Cys
            660             665             670

Asp His Leu Glu Arg Ala Ser Phe Ser Pro Val Gly Leu Arg Ser Leu
    675             680             685

Asn Leu Gly Ile Cys Pro Lys Leu Asn Glu Leu Lys Leu Glu Ala Pro
    690             695             700

Arg Met Asp Leu Leu Glu Leu Lys Gly Cys Gly Gly Leu Ser Glu Ala
705             710             715             720

Ala Ile Asn Cys Pro Arg Leu Thr Ser Leu Asp Ala Ser Phe Cys Gly
            725             730             735

Gln Leu Lys Asp Glu Cys Leu Ser Ala Thr Thr Ala Ser Cys Pro Gln
            740             745             750

Ile Glu Ser Leu Ile Leu Met Ser Cys Pro Ser Val Gly Ser Glu Gly
            755             760             765

Leu Tyr Ser Leu Arg Cys Leu Leu Lys Leu Val Val Leu Asp Leu Ser
    770             775             780

Tyr Thr Phe Leu Met Ser Leu Gln Pro Val Phe Glu Ser Cys Ile Gln
785             790             795             800

Leu Lys Val Leu Lys Leu Gln Ala Cys Lys Tyr Leu Thr Asp Ser Ser
            805             810             815

Leu Glu Pro Leu Tyr Lys Glu Asp Ala Leu Pro Ala Leu Gln Glu Leu
            820             825             830

Asp Leu Ser Tyr Gly Thr Leu Cys Gln Ser Ala Ile Glu Glu Leu Leu
        835             840             845

Ala Cys Cys Thr His Leu Thr His Val Ser Leu Asn Gly Cys Val Asn
    850             855             860
```

-continued

```
Met His Asp Leu Asn Trp Gly Cys Ser Ile Gly Gln Leu Ser Leu Ser
865             870             875             880

Ser Ile Pro Ile Pro Leu Gly Gln Ala Thr Leu Asp Glu Ile Glu Glu
            885             890             895

Pro Val Ala Gln Pro Asn Arg Leu Leu Gln Asn Leu Asn Cys Val Gly
            900             905             910

Cys Gln Asn Ile Arg Lys Val Leu Ile Pro Pro Ala Ala Arg Cys Phe
        915             920             925

His Leu Ser Ser Leu Asn Leu Ser Leu Ser Ser Asn Leu Lys Glu Val
        930             935             940

Asp Val Ser Cys Tyr Asn Leu Cys Phe Leu Asn Leu Ser Asn Cys Cys
945             950             955             960

Ser Leu Glu Val Leu Lys Leu Asp Cys Pro Arg Leu Thr Ser Leu Phe
            965             970             975

Leu Gln Ser Cys Asn Ile Glu Glu Glu Val Val Val Ala Ala Val Ser
            980             985             990

Arg Cys Ser Met Leu Glu Thr Leu Asp Val Arg Leu Cys Pro Lys Ile
        995             1000            1005

Ser Ser Ile Ser Met Val Gln Leu Arg Ile Ala Cys Pro Ser Leu
    1010            1015            1020

Lys Arg Ile Phe Ser Thr Leu Ser Pro Thr
    1025            1030
```

```
<210> SEQ ID NO 10
<211> LENGTH: 1033
<212> TYPE: PRT
<213> ORGANISM: Citrullus lanatus

<400> SEQUENCE: 10
```

```
Met Thr Ile Trp Cys Cys Leu Cys Phe Thr Val Gly Glu Glu Asp Glu
1               5               10              15

Arg Glu Arg Glu Glu Glu Leu Lys Lys Glu Gly Glu Met Lys Pro Met
            20              25              30

Met Arg Glu Glu Val Phe Glu Asn Gln Asp Asp Ser Asp Arg Ile Val
        35              40              45

Arg Asn Arg Asp Asp Ser Gln Gly Ser Asn Pro Leu Pro Ile Ala Val
    50              55              60

Asp Asp Ala Pro Asp Arg His Asp Gly Asp Arg Leu Arg Leu Phe Glu
65              70              75              80

Asp Met Val Arg Ala Met His Asp Gly Ala Asp Gly Gly Ala His
            85              90              95

Trp Asp Asp Glu Leu Arg Gly Gly Gly Gly Ala Ile Asn Pro Trp
            100             105             110

Asn Phe Ser Phe Gly Ile Leu His Gln Ser Glu Gly Gly Glu Ser Ser
        115             120             125

Ser Ala Ser Ala Leu Ser Leu Ser Ser Thr Val Glu Thr Ser Asn Glu
    130             135             140

Glu Arg Asp Arg Asp Ala Asn His Lys Arg Ala Lys Val Leu Ser Lys
145             150             155             160

Phe Thr Glu Ser Ser Phe Ala Thr Pro Trp Pro Leu Gly Ala Gly Asn
            165             170             175

Pro Met Arg Asp Tyr Asp Phe Ile His Gly Ser Ser Ser Ile Met Ser
            180             185             190

Arg Asn Glu Phe Leu Tyr His Ala Ser Thr Ser Cys Arg Val Asp Glu
        195             200             205
```

-continued

```
Asp Leu Glu Ser Ser Phe Gly Arg Asp Asp Gly Ile Asn Asp Asn Asp
    210             215             220

Thr Cys Lys Ser Glu Gly Phe Glu Val Arg Met Asp Leu Thr Asp Asp
225             230             235             240

Leu Leu His Met Val Phe Ser Phe Leu Asp His Ile Asn Leu Cys Arg
            245             250             255

Ala Ala Ile Val Cys Arg Gln Trp Gln Ala Ala Ser Ala His Glu Asp
            260             265             270

Phe Trp Arg Cys Leu Asn Phe Glu Asn Arg Asn Ile Ser Met Glu Gln
        275             280             285

Phe Glu Asp Met Cys Gly Arg Tyr Pro Asn Ala Thr Glu Val Asn Ile
    290             295             300

Ser Gly Val Pro Ala Val His Leu Leu Ala Met Lys Ala Val Ser Ser
305             310             315             320

Leu Arg His Leu Glu Val Leu Thr Leu Gly Arg Gly Gln Leu Ala Asp
            325             330             335

Asn Phe Phe His Ala Leu Thr Asp Cys His Leu Leu Lys Ser Leu Thr
            340             345             350

Val Asn Asp Ser Thr Leu Val Asn Val Thr Gln Glu Ile Pro Ile Ser
            355             360             365

His Asp Arg Leu Arg His Leu His Leu Thr Lys Cys Arg Val Ile Arg
    370             375             380

Ile Ser Val Arg Cys Pro Gln Leu Glu Thr Leu Ser Leu Lys Arg Ser
385             390             395             400

Asn Met Ala Gln Ala Val Leu Asn Cys Pro Leu Leu Arg Asp Leu Asp
            405             410             415

Ile Gly Ser Cys His Lys Leu Ser Asp Ala Ala Ile Arg Ser Ala Ala
            420             425             430

Ile Ser Cys Pro Gln Leu Glu Ser Leu Asp Met Ser Asn Cys Ser Cys
        435             440             445

Val Ser Asp Glu Thr Leu Arg Glu Ile Ser Ala Asn Cys Pro Asn Leu
    450             455             460

Gln Leu Leu Asn Ala Ser Tyr Cys Pro Asn Ile Ser Leu Glu Ser Val
465             470             475             480

Arg Leu Thr Met Leu Thr Val Leu Lys Leu His Ser Cys Glu Gly Ile
            485             490             495

Thr Ser Ala Ser Met Thr Ala Ile Ser Ser Ser Gly Leu Lys Val
            500             505             510

Leu Glu Leu Asp Asn Cys Ser Leu Leu Thr Ser Val Ser Leu Asp Phe
        515             520             525

Pro His Leu Gln Asn Ile Arg Leu Val His Cys Arg Lys Phe Ser Asp
    530             535             540

Leu Ser Leu Gln Ser Val Lys Leu Ser Ser Ile Met Val Ser Asn Cys
545             550             555             560

Pro Ser Leu His Arg Ile Asn Ile Thr Ser Asn Leu Leu Gln Lys Leu
            565             570             575

Val Leu Lys Lys Gln Glu Ser Leu Ala Lys Leu Val Leu Gln Cys Pro
            580             585             590

Ser Leu Gln Asp Val Asp Leu Thr Asp Cys Glu Ser Leu Thr Asn Ser
        595             600             605

Ile Cys Glu Val Phe Ser Asp Gly Gly Gly Cys Pro Met Leu Lys Ser
    610             615             620
```

-continued

```
Leu Val Leu Asp Asn Cys Glu Ser Leu Thr Ala Val Arg Phe Cys Ser
625             630                 635                 640

Ser Ser Leu Gly Ser Leu Ser Leu Val Gly Cys Arg Ala Ile Thr Ser
            645                 650                 655

Leu Glu Leu Gln Cys Pro Asn Leu Glu Gln Val Ser Leu Asp Gly Cys
            660                 665                 670

Asp His Leu Glu Arg Ala Ser Phe Ser Pro Val Gly Leu Arg Ser Leu
            675                 680                 685

Asn Leu Gly Ile Cys Pro Lys Leu Asn Glu Leu Lys Leu Glu Ala Pro
            690                 695                 700

Arg Met Asp Leu Leu Glu Leu Lys Gly Cys Gly Gly Leu Ser Glu Ala
705                 710                 715                 720

Ala Ile Asn Cys Pro Arg Leu Thr Ser Leu Asp Ala Ser Phe Cys Gly
                725                 730                 735

Gln Leu Lys Asp Glu Cys Leu Ser Ala Thr Thr Ala Ser Cys Pro Gln
                740                 745                 750

Ile Glu Ser Leu Ile Leu Met Ser Cys Pro Ser Val Gly Ser Glu Gly
                755                 760                 765

Leu Tyr Ser Leu Arg Cys Leu Leu Lys Leu Val Val Leu Asp Leu Ser
        770                 775                 780

Tyr Thr Phe Leu Met Ser Leu Gln Pro Val Phe Glu Ser Cys Ile Gln
785                 790                 795                 800

Leu Lys Val Leu Lys Leu Gln Ala Cys Lys Tyr Leu Thr Asp Ser Ser
                805                 810                 815

Leu Glu Pro Leu Tyr Lys Glu Asp Ala Leu Pro Ala Leu Gln Glu Leu
                820                 825                 830

Asp Leu Ser Tyr Gly Thr Leu Cys Gln Ser Ala Ile Glu Glu Leu Leu
            835                 840                 845

Ala Cys Cys Thr His Leu Thr His Val Ser Leu Asn Gly Cys Val Asn
    850                 855                 860

Met His Asp Leu Asn Trp Gly Cys Ser Ile Gly Gln Leu Ser Leu Ser
865                 870                 875                 880

Ser Ile Pro Ile Pro Leu Gly Gln Ala Thr Leu Asp Glu Ile Glu Glu
                885                 890                 895

Pro Val Ala Gln Pro Asn Arg Leu Leu Gln Asn Leu Asn Cys Val Gly
                900                 905                 910

Cys Gln Asn Ile Arg Lys Val Leu Ile Pro Pro Ala Ala Arg Cys Phe
            915                 920                 925

His Leu Ser Ser Leu Asn Leu Ser Leu Ser Ser Asn Leu Lys Glu Val
    930                 935                 940

Asp Val Ser Cys Tyr Asn Leu Cys Phe Leu Asn Leu Ser Asn Cys Cys
945                 950                 955                 960

Ser Leu Glu Val Leu Lys Leu Asp Cys Pro Arg Leu Thr Ser Leu Phe
                965                 970                 975

Leu Gln Ser Cys Asn Ile Glu Glu Glu Val Val Val Ala Ala Val Ser
            980                 985                 990

Arg Cys Ser Met Leu Glu Thr Leu  Asp Val Arg Leu Cys  Pro Lys Ile
        995                 1000                1005

Ser Ser  Ile Ser Met Val Gln  Leu Arg Ile Ala Cys  Pro Ser Leu
    1010                1015                1020

Lys Arg  Ile Phe Ser Thr Leu  Ser Pro Thr
    1025                1030
```

-continued

```
<210> SEQ ID NO 11
<211> LENGTH: 3102
<212> TYPE: DNA
<213> ORGANISM: Citrullus lanatus

<400> SEQUENCE: 11
atgacgattt ggtgctgctt atgcttcacc gttggagaag aagacgaaag ggaaagggaa      60
gaggaactga agaaggaagg tgaaatgaaa cccatgatgc gtgaggaggt ttttgagaac     120
caggatgact ctgatcgcat tgtgcgaaat cgtgatgatt ctcaagggag taatccactt     180
ccgattgctg tagatgatgc gcctgaccgt catgacggtg atcgacttag actgtttgag     240
gatatggtca gagcaatgca cgatggcgcc gatggtggtg gtgctcattg ggacgatgag     300
ctgcgcggcg gcggcggcgg ggctattaat ccctggaatt tttcttttgg aattctgcat     360
caatctgagg gaggagaaag tagtagcgcc tcggctttgt ccttgtcttc tacggtggag     420
acttctaatg aggaacgcga tcgggatgcc aaccataagc gcgctaaagt tctctccaaa     480
ttcactgaga gctcatttgc aactccatgg cctttgggtg ctggaaatcc tatgagagat     540
tatgatttta ttcacggatc atcttcaatt atgagtagga atgaatttct ataccatgct     600
tctacatcat gcagagttga cgaagatttg gaatctagtt ttggtagaga tgatgggatc     660
aatgataatg acacctgtaa atcagaagga tttgaagtaa gaatggatct tacagatgat     720
ttactgcata tggtgttctc tttcttggat cacatcaatc tttgtcgagc tgctatagtc     780
tgcaggcagt ggcaagctgc tagtgctcat gaagatttct ggaggtgttt gaattttgaa     840
aataggaaca tatccatgga acaattcgag gatatgtgtg gaagatatcc aaatgctaca     900
gaggtcaata tctctggtgt acctgccgtt cacttgcttg ccatgaaagc agtttcttct     960
ttaagacatc tggaggtttt aactctgggg agaggacaac tggcagataa cttttttcac    1020
gccctgactg attgccattt attgaagagt ttgactgtca atgattctac gctggttaat    1080
gttacacaag agatacctat aagccatgat agactgcgtc atcttcatct tactaaatgt    1140
cgtgttatac gcatatctgt tagatgtcca caacttgaaa cattgtcgtt gaagcgcagc    1200
aacatggcac aggctgttct taactgcccc cttcttcggg acctggatat aggctcttgc    1260
cacaagctct cagatgctgc aattcgctca gccgctattt catgcccaca gttggaatct    1320
cttgatatgt ctaattgttc atgtgttagc gatgagacat tacgtgaaat ttctgcaaac    1380
tgcccgaatc tccagcttct gaatgcatca tactgcccaa atatatcttt ggagtctgta    1440
agactgacaa tgctgaccgt gcttaagctt cacagctgtg agggcatcac atcagcttca    1500
atgaccgcaa tatctagtag ttctggtttg aaggttttgg agcttgataa ttgcagtctt    1560
ttgacttctg tttctctgga tcttccccat ttacagaata tcagacttgt tcattgccgc    1620
aaattctcag acttgagttt acagagtgtt aaattatcat ccataatggt ctctaattgt    1680
ccatcacttc atcggatcaa catcacttcc aatttacttc aaaaattggt gttgaagaaa    1740
caagagagct tggccaaatt ggttttgcag tgccctagtc tgcaagatgt ggacctcaca    1800
gactgtgaat cgctaacgaa ttctatttgt gaggttttta gtgatggtgg tggatgccct    1860
atgttgaaat cacttgttct tgataactgt gagagtctga ctgctgttcg attctgtagc    1920
agttctttag gcagtctttc ccttgttggt tgccgggcaa tcacttcact tgaacttcaa    1980
tgccctaatc tcgaacaggt ttctttagat ggctgtgatc atcttgagag agcatcattt    2040
tccccggttg gtctgcggtc actaaacctg ggaatctgtc ccaaattgaa tgaattaaaa    2100
cttgaggccc ctcggatgga tttacttgag ttaaaaggtt gtggtggatt gtctgaagca    2160
```

-continued

```
gccatcaatt gtcctcgtct aacatcgttg gatgcttcct tttgtggcca actgaaagat      2220
gagtgtttgt ctgcgactac tgcctcatgt ccacagattg agtcgttaat actgatgtca      2280
tgtccatcgg ttggttcaga ggggctttac tctctgcgat gccttctgaa gttggttgtg      2340
ctcgatttat catatacctt tttgatgagc ttgcagccag tcttcgagtc ttgtatacaa      2400
cttaaggtat tgaaactaca agcatgcaag tatttaactg actcatcgct agagcctctt      2460
tataaggaag acgctcttcc agctcttcaa gagttagact tatcttacgg gactctttgt      2520
cagtctgcca tagaagagct tcttgcttgt tgcactcact taactcatgt gagcttaaat      2580
gggtgtgtga acatgcatga tctaaattgg ggttgtagca ttggacagct ttcgttgtcc      2640
agcatcccaa ttcctcttgg tcaggccact cttgatgaga ttgaggaacc agttgcacag      2700
ccaaaccgtt tgttacagaa ccttaactgt gtaggttgtc agaatattag aaaggttctc      2760
attcctccag ctgctcgttg tttttcattta tcatcattaa acctatcctt gtcttcaaat      2820
ctcaaggaag ttgacgtctc ttgttacaac ctatgctttc ttaatttgag taattgctgc      2880
tctttggaag ttctaaaact tgactgcccg cggttaacca gtctctttct tcagtcttgc      2940
aacattgaag aagaagtggt tgtggctgcg gtatcgagat gtagcatgct cgagacgttg      3000
gatgtccgct tatgtccaaa gatctcctct attagcatgg tacaactgcg tattgcttgt      3060
ccaagtttga agcggatctt cagcactctg tctccaacat ga                        3102
```

```
<210> SEQ ID NO 12
<211> LENGTH: 3102
<212> TYPE: DNA
<213> ORGANISM: Citrullus lanatus

<400> SEQUENCE: 12
```

```
atgacgattt ggtgctgctt atgcttcacc gttggagaag aagacgaaag ggaaagggaa        60
gaggaactga agaaggaagg tgaaatgaaa cccatgatgc gtgaggaggt ttttgagaac       120
caggatgact ctgatcgcat tgtgcgaaat cgtgatgatt ctcaagggag taatccactt       180
ccgattgctg tagatgatgc gcctgaccgt catgacggtg atcgacttag actgtttgag       240
gatatggtca gagcaatgca cgatggcgcc gatggtggtg gtgctcattg ggacgatgag       300
ctgcgcggcg gcggcggcgg ggctattaat ccctggaatt tttcttttgg aattctgcat       360
caatctgagg gaggagaaag tagtagcgcc tcggctttgt ccttgtcttc tacggtggag       420
acttctaatg aggaacgcga tcgggatgcc aaccataagc gcgctaaagt tctctccaaa       480
ttcactgaga gctcatttgc aactccatgg cctttgggtg ctggaaatcc tatgagagat       540
tatgatttta ttcacggatc atcttcaatt atgagtagga atgaatttct ataccatgct       600
tctacatcat gcagagttga cgaagatttg gaatctagtt ttggtagaga tgatgggatc       660
aatgataatg acacctgtaa atcagaagga tttgaagtaa gaatggatct tacagatgat       720
ttactgcata tggtgttctc tttcttggat cacatcaatc tttgtcgagc tgctatagtc       780
tgcaggcagt ggcaagctgc tagtgctcat gaagatttct ggaggtgttt gaatttttgaa      840 aataggaaca tatccatgga acaattcgag gatatgtgtg gaagatatcc aaatgctaca       900
gaggtcaata tctctggtgt acctgccgtt cacttgcttg ccatgaaagc agtttcttct       960
ttaagacatc tggaggtttt aactctgggg agaggacaac tggcagataa cttttttcac      1020
gccctgactg attgccattt attgaagagt ttgactgtca atgattctac gctggttaat      1080
gttacacaag agatacctat aagccatgat agactgcgtc atcttcatct tactaaaatgt      1140 cgtgttatac gcatatctgt tagatgtcca caacttgaaa cattgtcgtt gaagcgcagc      1200
```

-continued

```
aacatggcac aggctgttct taactgcccc cttcttcggg acctggatat aggctcttgc      1260
cacaagctct cagatgctgc aattcgctca gccgctattt catgcccaca gttggaatct      1320
cttgatatgt ctaattgttc atgtgttagc gatgagacat tacgtgaaat ttctgcaaac      1380
tgcccgaatc tccagcttct gaatgcatca tactgcccaa atatatcttt ggagtctgta      1440
agactgacaa tgctgaccgt gcttaagctt cacagctgtg agggcatcac atcagcttca      1500
atgaccgcaa tatctagtag ttctggtttg aaggttttgg agcttgataa ttgcagtctt      1560
ttgacttctg tttctctgga ttttccccat ttacagaata tcagacttgt tcattgccgc      1620
aaattctcag acttgagttt acagagtgtt aaattatcat ccataatggt ctctaattgt      1680
ccatcacttc atcggatcaa catcacttcc aatttacttc aaaaattggt gttgaagaaa      1740
caagagagct tggccaaatt ggttttgcag tgccctagtc tgcaagatgt ggacctcaca      1800
gactgtgaat cgctaacgaa ttctatttgt gaggttttta gtgatggtgg tggatgccct      1860
atgttgaaat cacttgttct tgataactgt gagagtctga ctgctgttcg attctgtagc      1920
agttctttag gcagtctttc ccttgttggt tgccgggcaa tcacttcact tgaacttcaa      1980
tgccctaatc tcgaacaggt ttctttagat ggctgtgatc atcttgagag agcatcattt      2040
tccccggttg gtctgcggtc actaaacctg ggaatctgtc ccaaattgaa tgaattaaaa      2100
cttgaggccc ctcggatgga tttacttgag ttaaaaggtt gtggtggatt gtctgaagca      2160
gccatcaatt gtcctcgtct aacatcgttg gatgcttcct tttgtggcca actgaaagat      2220
gagtgtttgt ctgcgactac tgcctcatgt ccacagattg agtcgttaat actgatgtca      2280
tgtccatcgg ttggttcaga ggggctttac tctctgcgat gccttctgaa gttggttgtg      2340
ctcgatttat catataccttt tttgatgagc ttgcagccag tcttcgagtc ttgtatacaa      2400
cttaaggtat tgaaactaca agcatgcaag tatttaactg actcatcgct agagcctctt      2460
tataaggaag acgctcttcc agctcttcaa gagttagact tatcttacgg gactctttgt      2520
cagtctgcca tagaagagct tcttgcttgt tgcactcact taactcatgt gagcttaaat      2580
gggtgtgtga acatgcatga tctaaattgg ggttgtagca ttggacagct ttcgttgtcc      2640
agcatcccaa ttcctcttgg tcaggccact cttgatgaga ttgaggaacc agttgcacag      2700
ccaaaccgtt tgttacagaa ccttaactgt gtaggttgtc agaatattag aaaggttctc      2760
attcctccag ctgctcgttg tttttcattta tcatcattaa acctatcctt gtcttcaaat      2820
ctcaaggaag ttgacgtctc ttgttacaac ctatgctttc ttaatttgag taattgctgc      2880
tctttggaag ttctaaaact tgactgcccg cggttaacca gtctctttct tcagtcttgc      2940
aacattgaag aagaagtggt tgtggctgcg gtatcgagat gtagcatgct cgagacgttg      3000
gatgtccgct tatgtccaaa gatctcctct attagcatgg tacaactgcg tattgcttgt      3060
ccaagtttga agcggatctt cagcactctg tctccaacat ga                          3102
```

<210> SEQ ID NO 13
<211> LENGTH: 41
<212> TYPE: PRT
<213> ORGANISM: Citrullus lanatus

<400> SEQUENCE: 13

```
Leu Thr Asp Asp Leu Leu His Met Val Phe Ser Phe Leu Asp His Ile
1               5                   10                  15

Asn Leu Cys Arg Ala Ala Ile Val Cys Arg Gln Trp Gln Ala Ala Ser
            20                  25                  30
```

-continued

```
Ala His Glu Asp Phe Trp Arg Cys Leu
    35                  40

<210> SEQ ID NO 14
<211> LENGTH: 6890
<212> TYPE: DNA
<213> ORGANISM: Citrullus lanatus

<400> SEQUENCE: 14
atgacgattt ggtgctgctt atgcttcacc gttggagaag aagacgaaag ggaaagggaa      60
gaggaactga agaaggaagg tgaaatgaaa cccatgatgc gtgaggaggt ttttgagaac     120
caggatgact ctgatcgcat tgtgcgaaat cgtgatgatt ctcaagggag taatccactt     180
ccgattgctg tagatgatgc gcctgaccgt catgacggtg atcgacttag actgtttgag     240
gatatggtca gagcaatgca cgatggcgcc gatggtggtg gtgctcattg ggacgatgag     300
ctgcgcggcg gcggcggcgg ggctattaat ccctggaatt tttcttttgg aattctgcat     360
caatctgagg gaggagaaag tagtagcgcc tcggctttgt ccttgtcttc tacggtggag     420
acttctaatg aggaacgcga tcgggatgcc aaccataagc gcgctaaagt tctctccaaa     480
ttcacgtgag tcacttgtag actgcttctg gatatgaatt atgctaaggt ttcatgggtt     540
tgccattttt cttggttttc ttttcccct tttccgaaag gggtgttggt tttttttttt     600
tttttttttg ttccttctta aatgttctct ctttgtggga tttaggacta gatattgtgg     660
tggtttttgg atggagatcg ttagcattta ttgaggttat catttacgaa tatgcagggt     720
tctttgtaat ttagctatca atgcaggctg tttgttgtta tttttgtgcc ggcatctctg     780
aataatttgc tgttttgcac tgcaagatag ctatggaaaa ttacgtattt tatgatctaa     840
acgtgctccg cttctttagc tctcgggctg tatcagcgtt tggaaagtag ttgttctata     900
gattttcacg agcaccttct attcttgaat acttgaagtg gtgtctaata taaagcaata     960 tgttttgca tcgaccttat cccgtccatc tttattgtat gtattagact gttggcaggc    1020
tctttatcat tgtattttaa atattttttc ccgatttcta aattagaaat gtgtttctta    1080
atcaatagtg gcatgttgct tgggcttttc tagaagagat atcatacggt gtgccaagat    1140
gatatctcaa agtcttcttc agttgcgagt cttctgagtg agttgtcacc atggaaaagt    1200
ttccttttct tcatggaata gaaaatcatt tatatttgag aaattcaata tatggttttc    1260
tttctctgag aagagtttga aaatgaaaag tatagatatg aatgtttatt gttttttgatt    1320 gtcttattaa ttgttttttt gaagcaaacc ttcatgtaca acgatattta gggtgtttga    1380
atgcacatag gttctcctat tacatgattt atttatgtac tgaaaattaa aggtgtatta    1440
aatttgagtc ataatttttg taaaaactat tctttctaaa ttgttttctg gatatgccca    1500
aacaagtcct tatattttca agcactgttg accttggtag tatagttatc acactcattt    1560
gcaaacctac ttgtgatact atactttcat tactagttaa aaaaatgtct tcgttaaggt    1620
ttatcatgga gggatgagta tatagctgtt gtcttactgc taaatatgat cttatgttgg    1680
aaactctgcc cttcacatgg tggttgatga tgtatcatgt gatctttagt ttaaaaaaga    1740
gtaaactctg agttaactaa atgtaagtat gtgcagtaat actcattcca gataattcac    1800
attctctcaa ccgtttagat cttgcaaatt agcaccatca agtttcctat aatttacaag    1860
ttagactaac tgataagtgt aaagttagaa atgatgctcg ttattcactt ttaacaattg    1920
tttcttattt tcttttcttt tcaatcttcc ctagtgagag ctcatttgca actccatggc    1980
ctttgggtgc tggaaatcct atgagagatt atgatttat tcacggatca tcttcaatta    2040
```

-continued

```
tgagtaggaa tgaatttcta taccatgctt ctacatcatg cagagttgac gaagatttgg    2100
aatctagttt tggtagagat gatgggatca atgataatga cacctgtaaa tcagaaggat    2160
ttgaagtaag aatggatctt acagatgatt tactgcatat ggtatgcatc tccagagatt    2220
tattattgtt ttcttgctta ccgtcttatt tcttggattt cttattcaca tgaagttaaa    2280
ttaattgata tcaggtgttc tctttcttgg atcacatcaa tctttgtcga gctgctatag    2340
tctgcaggca gtggcaagct gctagtgctc atgaagattt ctggaggtgt ttgaattttg    2400
aaaataggaa catatccatg gaacaatgta ggtgttgttc tgcttcttcc tttcattttc    2460
tagagtagtt gagacaagaa tgaggtgatt ttaaaaatgt tggttgcctc ttggaaatag    2520
aggtgatata ttatgatgta acttcaaaac atgtaggatg cagtatttga gtctggaatg    2580
tctttagcac tcatgaaatg ttgttaaaag cctaggactg cgacatattt ggggcttgtt    2640
ttcagtactc agtaggattt ttctccctaa atctttttga ctaggtatgt atataatatt    2700
aaaggaaaga acttcttgat gctattttta gctttggcaa tctcttgatt cttttaaaat    2760
aagttctgga tataattgta taaatgtgat aggatgtgac atatctctgt agcagtcttg    2820
gtgccagtgc caatgcaaca ctttcaatcg tatttcaagt ttaacctact tttatccagt    2880
cacattttct ttctacccac catacagtat aaattgatcc ggttgtattt ctttgtgcct    2940
ctgtattaac aactgtccta tcctattcta tgttgcttac tttctaacat cattctgatt    3000
tggagctagt tagttaattg attaattctg actgcagtcg aggatatgtg tggaagatat    3060
ccaaatgcta cagaggtcaa tatctctggt gtacctgccg ttcacttgct tgccatgaaa    3120
gcagtttctt ctttaaggta atgattacgg ttttgtattt ttgttttttt tcctcatcct    3180
gaatctttat ggtggtgctt attatttat tattgtctca gacatctgga ggttttaact     3240
ctggggagag gacaactggc agataacttt tttcacgccc tgactgattg ccatttattg    3300
aagagtttga ctgtcaatga ttctacgctg gttaatgtta cacaagagat acctataagc    3360
catgatagac tgcgtcatct tcatcttact aaatgtcgtg ttatacgcat atctgttagg    3420
ttgctaatgt ttatgtatct taatgctaac tgtatttaat tgtttagttt gttttttttt    3480 ttttttgg tctaaagcat gttttcttgc agatgtccac aacttgaaac attgtcgttg      3540
aagcgcagca acatggcaca ggctgttctt aactgcccc ttcttcggga cctggatata     3600
ggctcttgcc acaagctctc agatgctgca attcgctcag ccgctatttc atgcccacag    3660
ttggaatctc ttgatatgtc taattgttca tgtgttagcg atgagacatt acgtgaaatt    3720
tctgcaaact gcccgaatct ccagcttctg aatgcatcat actgcccaaa tatatctttg    3780
gaggtggcat accattttta gttaaatttt gagcgaaagt gactattttg cccttcagac    3840
ttgtttttcc tgatattttg gttccttttt cttttgaagt ctgtaagact gacaatgctg    3900
accgtgctta agcttcacag ctgtgagggc atcacatcag cttcaatgac cgcaatatct    3960
agtagttctg gtttgaaggt ctgaaataac ctatttcgac tgtttatatt ttctagttgt    4020
ctggtgctgt gtctgagtta gttgaaaatg gaatggagac ttattgcagg ttttggagct    4080
tgataattgc agtcttttga cttctgtttc tctggatctt ccccatttac agaatatcag    4140
acttgttcat tgccgcaagt atgtcttctc atctccaagc aactcatagc ttctatcaca    4200
tgattaattt catttagaag gacttttgaa ctgggccttc acttcttttt tccttgagtt    4260
gaatctgttt cgccattctt gcagattctc agacttgagt ttacagagtg ttaaattatc    4320
atccataatg gtctctaatt gtccatcact tcatcggatc aacatcactt ccaatttact    4380
tcaagtatgt cgtaatggat cttaaagttt tctttcttat taatttcatt tcataagggt    4440
```

-continued

```
ataaacgaac attggactgt acttttgtgg acttgcagaa attggtgttg aagaaacaag    4500
agagcttggc caaattggtt ttgcagtgcc ctagtctgca agatgtggac ctcacagact    4560
gtgaatcgct aacgaattct atttgtgagg tttttagtga tggtggtgga tgccctatgt    4620
tgaaatcact tgttcttgat aactgtgagg taagtagctt ggtgttaccc atcagtatca    4680
tcgcattggc ccttgtgatt tcataatttg gaaattattt gattgagact ttccattgat    4740
ttctaatgtg aacatgtttc ttttgttcag agtctgactg ctgttcgatt ctgtagcagt    4800
tctttaggca gtctttccct tgttggttgc cgggcaatca cttcacttga acttcaatgc    4860
cctaatctcg aacaggtttc tttagatggc tgtgatcatc ttgagagagc atcattttcc    4920
ccggtatgtg aaaactgaca acttgtaaat ttttctcagt cactatatta taaatattct    4980
ccttagcgct aaagattggg cttttttctc tcttttttaa ggttggtctg cggtcactaa    5040
acctgggaat ctgtcccaaa ttgaatgaat taaaacttga ggcccctcgg atggatttac    5100
ttgagttaaa aggttgtggt ggattgtctg aagcagccat caattgtcct cgtctaacat    5160
cgttggatgc ttccttttgt gggttagttt gttatgatta tttggatgac accttctatt    5220
tgatggatac tggttgctta tgtcgttgag ttcttctttt tcccttgcag ccaactgaaa    5280
gatgagtgtt tgtctgcgac tactgcctca tgtccacaga ttgagtcgtt aatactgatg    5340
tcatgtccat cggttggttc agaggggctt tactctctgc gatgccttct gaagttggtt    5400
gtgctcgatt tatcatatac ctttttgatg agcttgcagc cagtcttcga gtcttgtata    5460
caacttaagg tacctttttg atagatatta tcatgacccc tgtctgattt ctgttgtatt    5520
gatgccttct tctttgtgtt cttaatgaag gtattgaaac tacaagcatg caagtattta    5580
actgactcat cgctagagcc tctttataag gaagacgctc ttccagctct tcaagagtta    5640
gacttatctt acgggactct ttgtcagtct gccatagaag agcttcttgc ttgttgcact    5700
cacttaactc atgtgagctt aaatgggtgt gtgaacatgc atgatctaaa ttggggttgt    5760
agcattggac agctttcgtt gtccagcatc ccaattcctc ttggtcaggc cactcttgat    5820
gagattgagg aaccagttgc acagccaaac cgtttgttac agaaccttaa ctgtgtaggt    5880
tgtcagaata ttagaaaggt tctcattcct ccagctgctc gttgttttca tttatcatca    5940
ttaaacctat ccttgtcttc aaatctcaag gaagttgacg tctcttgtta caacctatgc    6000
tttcttaatt tgaggttatg cccccctacc cttttgctcc attaacaatt ttagttggtt    6060
cctttctttt tttttttttt ggcctaccct gctaaatccg tgtttttgtg atctagtaat    6120
tgctgctctt tggaagttct aaaacttgac tgcccgcggt taaccagtct ctttcttcag    6180
gtaatttttt cttcaatgta agtttttggat gttcatacta atctactctg aatagtccag    6240
aatctggtct tccaagcaat ccgaaactaa ccgttgggga tagggtggac aaaaaatggg    6300
gtcaagacag attacaacgc acaagtccac attataagga cccagtcaat gactggagtt    6360
gaactcccaa cctgagaccc ccctgtaggg ctgtaggcct cgggtctaag gaccccaatt    6420
ttgtttgcat cccccctccac tttttaacctt tttttttttt ttttttttgg gataggaatt    6480
catccattgt tggaatcatt tgattatagt ttatttttta tcttattttt tactgttgtg    6540
ttgggtaaac aatactttgg tttcaaactt gagaaaaaaa gaaatggcag ctaagagatg    6600
catatgaatt ttatgatatg aggctaacta gatctgtctt ttcctagtct tgcaacattg    6660
aagaagaagt ggttgtggct gcggtatcga gatgtagcat gctcgagacg ttggatgtcc    6720
gcttatgtcc aaaggtgagg ggtgtctctc ttttcctcta cattgtttga tagttttggc    6780
```

-continued

```
tgacttcata atatttcttc tactggcaga tctcctctat tagcatggta caactgcgta    6840
ttgcttgtcc aagtttgaag cggatcttca gcactctgtc tccaacatga               6890
```